US009289368B2

(12) United States Patent
Yamazaki et al.

(10) Patent No.: US 9,289,368 B2
(45) Date of Patent: Mar. 22, 2016

(54) HAIR COSMETIC

(75) Inventors: Naoyuki Yamazaki, Wakayama (JP); Yasuhiro Doi, Wakayama (JP); Hiroyuki Terazaki, Wakayama (JP)

(73) Assignee: KAO CORPORATION, Tokyo (JP)

( * ) Notice: Subject to any disclaimer, the term of this patent is extended or adjusted under 35 U.S.C. 154(b) by 158 days.

(21) Appl. No.: 13/977,472

(22) PCT Filed: Dec. 27, 2011

(86) PCT No.: PCT/JP2011/080346
§ 371 (c)(1),
(2), (4) Date: Jun. 28, 2013

(87) PCT Pub. No.: WO2012/091073
PCT Pub. Date: Jul. 5, 2012

(65) Prior Publication Data
US 2013/0295033 A1 Nov. 7, 2013

(30) Foreign Application Priority Data

Dec. 28, 2010 (JP) .................................. 2010-294131
Dec. 28, 2010 (JP) .................................. 2010-294134
May 2, 2011 (JP) .................................. 2011-103313
May 2, 2011 (JP) .................................. 2011-103316

(51) Int. Cl.
| *A61K 8/73* | (2006.01) |
| *A61K 8/42* | (2006.01) |
| *A61K 8/46* | (2006.01) |
| *A61Q 5/02* | (2006.01) |
| *A61Q 5/12* | (2006.01) |
| *A61Q 19/10* | (2006.01) |
| *A61K 8/92* | (2006.01) |
| *A61K 8/39* | (2006.01) |
| *A61Q 5/00* | (2006.01) |
| *A61K 8/33* | (2006.01) |
| *C08B 11/193* | (2006.01) |
| *C08L 1/26* | (2006.01) |
| *C08L 1/28* | (2006.01) |
| *C08B 1/06* | (2006.01) |
| *C08B 1/08* | (2006.01) |
| *C08B 11/08* | (2006.01) |
| *C08B 11/145* | (2006.01) |
| *C08B 11/20* | (2006.01) |
| *C08L 5/00* | (2006.01) |

(52) U.S. Cl.
CPC . *A61K 8/731* (2013.01); *A61K 8/33* (2013.01); *A61K 8/39* (2013.01); *A61K 8/42* (2013.01); *A61K 8/463* (2013.01); *A61K 8/922* (2013.01); *A61Q 5/00* (2013.01); *A61Q 5/02* (2013.01); *A61Q 5/12* (2013.01); *A61Q 19/10* (2013.01); *C08B 1/06* (2013.01); *C08B 1/08* (2013.01); *C08B 11/08* (2013.01); *C08B 11/145* (2013.01); *C08B 11/193* (2013.01); *C08B 11/20* (2013.01); *C08L 1/26* (2013.01); *C08L 1/284* (2013.01); *C08L 1/288* (2013.01); *C08L 5/00* (2013.01)

(58) Field of Classification Search
None
See application file for complete search history.

(56) References Cited

U.S. PATENT DOCUMENTS

| 3,472,840 | A | 10/1969 | Stone et al. | |
| 3,816,616 | A | 6/1974 | Anguillo et al. | |
| 5,254,333 | A * | 10/1993 | Kajino et al. | 424/70.11 |
| 7,297,717 | B2 * | 11/2007 | Iwai et al. | 424/70.23 |
| 8,632,761 | B2 | 1/2014 | Doi et al. | |
| 2005/0227902 | A1 | 10/2005 | Erazo-Majewicz et al. | |
| 2006/0073110 | A1 | 4/2006 | Modi | |
| 2010/0274001 | A1 | 10/2010 | Okutsu et al. | |
| 2012/0015894 | A1 | 1/2012 | Terada | |
| 2012/0214985 | A1 | 8/2012 | Takai et al. | |
| 2012/0230934 | A1 * | 9/2012 | Doi et al. | 424/70.13 |

FOREIGN PATENT DOCUMENTS

| EP | 0149249 A2 | 7/1985 |
| EP | 2500012 A1 | 9/2012 |
| JP | 45-20318 | 7/1970 |
| JP | 54-87787 A | 7/1979 |
| JP | 59-42681 | 10/1984 |
| JP | 4-230614 A | 8/1992 |
| JP | 2000-143462 A | 5/2000 |
| JP | 2000-327541 A | 11/2000 |
| JP | 2001-513538 A | 9/2001 |
| JP | 2001-513539 A | 9/2001 |
| JP | 2005-306843 A | 11/2005 |

(Continued)

OTHER PUBLICATIONS

The Communication and extended Search Report, dated Nov. 6, 2014, issued in the corresponding European Patent Application No. 11854139.0.

(Continued)

*Primary Examiner* — Brian Gulledge
(74) *Attorney, Agent, or Firm* — Birch, Stewart, Kolasch & Birch, LLP.

(57) ABSTRACT

The present invention relates to a hair cosmetic capable of giving good finger combability and manageability with no oily feeling to the hair treated therewith and dried, and to a method for producing the hair cosmetic. The hair cosmetic contains a cationized hydroxypropyl cellulose (A), an oil (B) of which the amount of dissolution in 100 g of water at 20° C. is from 0 to 1 g, and a surfactant (C), wherein the cationized hydroxypropyl cellulose (A) has an anhydroglucose-derived main chain and has a degree of substitution with cationized ethyleneoxy group of from 0.01 to 2.9 and a degree of substitution with propyleneoxy group of from 0.1 to 4.0, and the production method is for producing the hair cosmetic.

19 Claims, No Drawings

(56) References Cited

FOREIGN PATENT DOCUMENTS

| | | | |
|---|---|---|---|
| JP | 2006-151992 A | 6/2006 | |
| JP | 2008-514604 A | 5/2008 | |
| JP | 2009-143997 A | 7/2009 | |
| JP | 2009-263291 A | 11/2009 | |
| WO | WO 99/09947 A1 | 3/1999 | |
| WO | WO 99/09948 A1 | 3/1999 | |
| WO | WO 2010/035893 A2 | 4/2010 | |
| WO | WO 2010/113446 A1 | 10/2010 | |
| WO | WO 2011/019876 A2 | 2/2011 | |
| WO | WO 2011/052733 A1 | 5/2011 | |
| WO | WO 2011/059063 * | 5/2011 | ............... A61K 8/73 |
| WO | WO 2011/059063 A1 | 5/2011 | |

OTHER PUBLICATIONS

English translation of JP-59-42681, published Oct. 17, 1984.
Extended European Search Report, issued Nov. 5, 2014, for European Application No. 11852470.1.
International Search Report and Written Opinion of the International Searching Authority, together with English translation of the International Search Report, dated Apr. 17, 2012, issued in International Application No. PCT/JP2011/080346.
International Search Report and Written Opinion of the International Searching Authority, together with English translation of the International Search Report, dated Apr. 17, 2012, issued in PCT/JP/2011/080345.
International Search Report issued Jan. 11, 2011, in International Application No. PCT/JP2010/70211.
US Office Action, dated Sep. 24, 2014, for U.S. Appl. No. 13/976,716.
Matsuzaki, F., "Progress of the recent emulsion technology application as the emulsifier of the polyelectrolyte complex," Fragrance Journal, vol. 26, No. 8, Aug. 15, 1998, (14 pages), including a full English machine translation of pp. 42-46 and p. 135.
Sato et al., "Shampoo," Perfumery-and-cosmetics science, Mar. 20, 1997, (23 pages), including a full English machine translation of pp. 126-131.

* cited by examiner

HAIR COSMETIC

FIELD OF THE INVENTION

The present invention relates to a hair cosmetic containing a cationized hydroxypropyl cellulose, an oil and a surfactant, and to a method for producing it.

BACKGROUND OF THE INVENTION

Hair is damaged by chemical treatment for hair coloring, or by physical treatment in hair washing or by heat in drying with a drier. It is known that, when damaged, hair involves negative elements from an aesthetic viewpoint of becoming moistless, unmanageable and unshiny. Consequently, a conditioning agent is widely used for regenerating hair to regain a silky smooth feeling before treatment thereof.

A hair conditioning agent contains an oil such as silicone, ester oil, hydrocarbon oil or the like for preventing hair from becoming moistless and for making hair have improved finger combability and manageability. However, increasing the amount of oil in the agent is defective in that, though the hair could be prevented from becoming moistless but would have an oily feeling and would rather have a bad feeling.

Patent Reference 1 discloses a hair cosmetic containing a specific modified silicone polymer, a cationized polymer and a silicone oil for the purpose of improving hair-dressing and conditioning capability.

Patent Reference 2 discloses a natural polymer-based cosmetic capable of providing a good feeling in use, which contains a dispersion of low-substitution hydroxypropyl cellulose particles uniformly dispersed in a swollen state therein.

Patent Reference 3 discloses a two-layer separated hair cosmetic with which the hair finished is not clammy and can be managed to be silky and smooth, and the hair cosmetic contains a high-polymerization silicone, a water-soluble thickener and water.

Patent Reference 4 discloses a method for producing a cation-modified cellulose derivative such as a cationized hydroxypropyl cellulose or the like, saying that the derivative can be used as an additive to hair cosmetics, etc.

Patent Reference 5 discloses a hair spray composition containing a cationized hydroxypropyl cellulose and an alcohol solvent.

Further, there have been proposed a cosmetic containing at least one selected from a dialkyl ether, an ester oil, a hydroxycarboxylate and the like (see Patent Reference 6), a cosmetic containing a specific dialkyl carbonate and an emulsifier (see Patent Reference 7), and a cosmetic composition containing an ester of an alkoxylated aromatic alcohol and an aliphatic carboxylic acid, and a functional component (see Patent Reference 8).

CITATION LIST

Patent References

Patent Reference 1: JP-A 5-148123
Patent Reference 2: JP-A 2006-151992
Patent Reference 3: JP-A 2009-161508
Patent Reference 4: JP-A 53-90368
Patent Reference 5: JP-A 60-170601
Patent Reference 6: JP-T 2000-512284
Patent Reference 7: JP-T 2000-512285
Patent Reference 8: JP-T 2005-506347

SUMMARY OF THE INVENTION

The present invention relates to the following (1) and (2):

(1) A hair cosmetic containing a cationized hydroxypropyl cellulose (A), an oil (B) of which the amount of dissolution in 100 g of water at 20° C. is from 0 to 1 g, and a surfactant (C), wherein the cationized hydroxypropyl cellulose (A) has an anhydroglucose-derived main chain represented by a specific general formula, and has a degree of substitution with cationized ethyleneoxy group of from 0.01 to 2.9 and a degree of substitution with propyleneoxy group of from 0.1 to 4.0.

(2) A method for producing a hair cosmetic containing a cationized hydroxypropyl cellulose (A), an oil (B) of which the amount of dissolution in 100 g of water at 20° C. is from 0 to 1 g, and a surfactant (C), in which the cationized hydroxypropyl cellulose (A) has an anhydroglucose-derived main chain represented by a specific general formula, and has a degree of substitution with cationized ethyleneoxy group of from 0.01 to 2.9 and a degree of substitution with propyleneoxy group of from 0.1 to 4.0, and which includes specific steps.

DETAILED DESCRIPTION OF THE INVENTION

In conventional hair cosmetics, the oil is limited to a specific modified silicone and therefore has a problem in that the latitude in its incorporation is limited, and in addition, in taking out in use thereof, the hair cosmetic must be fully stirred to once keep an emulsified condition, or that is, the type of usage thereof is not simple. Further, conventional hair cosmetics are not on a satisfactory level in point of the feeling in use thereof in that they could not provide good finger combability and manageability of hair after drying with no oily feeling.

The present invention relates to a hair cosmetic capable of providing good finger combability and manageability of hair after treated and dried with no oily feeling, and to a method for producing the hair cosmetic.

Specifically, the present invention relates to the following (1) and (2):

(1) A hair cosmetic containing a cationized hydroxypropyl cellulose (A), an oil (B) of which the amount of dissolution in 100 g of water at 20° C. is from 0 to 1 g, and a surfactant (C), wherein the cationized hydroxypropyl cellulose (A) has an anhydroglucose-derived main chain represented by the following general formula (1), and has a degree of substitution with cationized ethyleneoxy group of from 0.01 to 2.9 and a degree of substitution with propyleneoxy group of from 0.1 to 4.0.

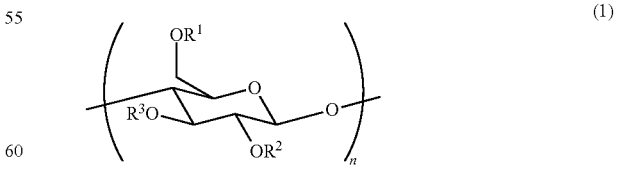

(1)

(In the formula, $R^1$, $R^2$ and $R^3$ each independently represent a substituent having a cationized ethyleneoxy group and a propyleneoxy group represented by the following general formula (2); n indicates a mean degree of polymerization of anhydroglucose and is a number of from 20 to 5000).

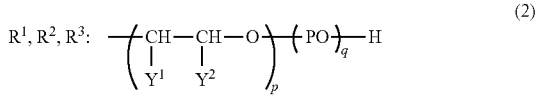

(In the formula, one of $Y^1$ and $Y^2$ is a hydrogen atom and the other is a cationic group represented by the following general formula (3); PO represents a propyleneoxy group. p indicates the number of cationized ethyleneoxy groups ($(-CH(Y^1)-CH(Y^2)-O-)$) in the general formula (2) and q indicates the number of propyleneoxy groups (—PO—) therein, each representing 0 or a positive integer. In case where both of p and q are not 0, the addition sequence of the cationized ethyleneoxy group and the propyleneoxy group is not defined, and in case where p and/or q are/is 2 or more, a binding form may be any of like a block co-polymer or like a random co-polymer).

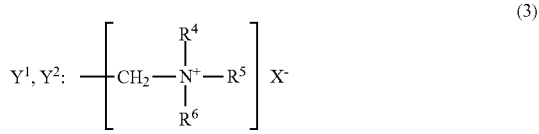

(In the formula, $R^4$, $R^5$ and $R^6$ each independently represent a linear or branched alkyl group having from 1 to 3 carbon atoms, and $X^-$ represents an anionic group).

(2) A method for producing a hair cosmetic containing a cationized hydroxypropyl cellulose (A), an oil (B) of which the amount of dissolution in 100 g of water at 20° C. is from 0 to 1 g, and a surfactant (C), in which the cationized hydroxypropyl cellulose (A) has an anhydroglucose-derived main chain represented by the above-mentioned general formula (1), and has a degree of substitution with cationized ethyleneoxy group of from 0.01 to 2.9 and a degree of substitution with propyleneoxy group of from 0.1 to 4.0; the method including the following steps (a-1) to (a-3), the following steps (b-1) to (b-4), or the following steps (c-1) to (c-4):

Step (a-1): a step of adding a cationizing agent to pulp and processing it with a grinder, Step (a-2): a step of adding a base to the grinder-processed product obtained in the step (a-1), and while processing it with a grinder, reacting pulp and the cationizing agent to give a cationized cellulose, Step (a-3): a step of reacting the cationized cellulose obtained in the step (a-2) with propylene oxide to give the cationized hydroxypropyl cellulose (A), Step (b-1): a step of processing pulp with a grinder, Step (b-2): a step of adding a base to the grinder-processed product obtained in the step (b-1) to give an alkali cellulose, Step (b-3): a step of reacting the alkali cellulose obtained in the step (b-2) and propylene oxide to give a hydroxypropyl cellulose, Step (b-4): a step of reacting the hydroxypropyl cellulose obtained in the step (b-3) with a cationizing agent to give the cationized hydroxypropyl cellulose (A), Step (c-1): a step of processing a mixture of a cellulose-containing raw material and a base compound in an amount of from 0.6 to 1.5 molar times per mol of the anhydroglucose unit that constitutes the cellulose in the cellulose-containing raw material, with a grinder under the condition where the water content in the cellulose-containing raw material is at most 10% by weight relative to the cellulose therein, thereby giving a ground cellulose/base mixture in which the mean particle size of the cellulose is from 10 to 150 μm, Step (c-2): a step of adding water to the ground cellulose/base mixture obtained in the step (c-1) to thereby control the water content in the ground cellulose/base mixture to be from 30 to 100% by mass relative to the cellulose in the cellulose-containing raw material used in the step (c-1), thereby giving an alkali cellulose, Step (c-3): a step of reacting the alkali cellulose obtained in the step (c-2) with propylene oxide to give a hydroxypropyl cellulose, Step (c-4): a step of reacting the hydroxypropyl cellulose obtained in the step (c-3) with a cationizing agent to give the cationized hydroxypropyl cellulose (A).

According to the present invention, there can be provided a hair cosmetic capable of imparting good finger combability and manageability to hair after treated and dried with no oily feeling thereto, and a method for producing the hair cosmetic.

[Hair Cosmetic]

The hair cosmetic of the present invention contains a specific cationized hydroxypropyl cellulose (A), an oil (B) of which the amount of dissolution in 100 g of water at 20° C. is from 0 to 1 g, and a surfactant (C).

<Cationized Hydroxypropyl Cellulose (A)>

The hair cosmetic of the present invention contains, as the component (A), a cationized hydroxypropyl cellulose (hereinafter this may be referred to as "C—HPC") having an anhydroglucose-derived main chain represented by the following general formula (1), and having a degree of substitution with cationized ethyleneoxy group of from 0.01 to 2.9 and a degree of substitution with propyleneoxy group of from 0.1 to 4.0.

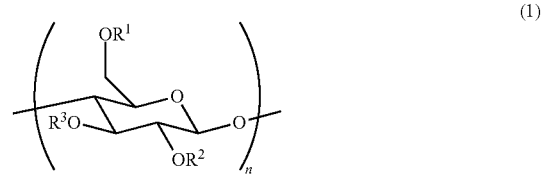

(In the formula, $R^1$, $R^2$ and $R^3$ each independently represent a substituent having a cationized ethyleneoxy group and a propyleneoxy group represented by the following general formula (2); n indicates a mean degree of polymerization of anhydroglucose and is a number of from 50 to 5000).

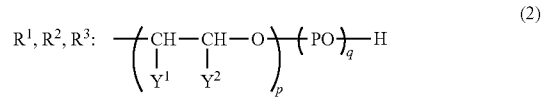

(In the formula, one of $Y^1$ and $Y^2$ is a hydrogen atom and the other is a cationic group represented by the following general formula (3); PO represents a propyleneoxy group. p indicates the number of cationized ethyleneoxy groups ($(-CH(Y^1)-CH(Y^2)-O-)$) in the general formula (2) and q indicates the number of propyleneoxy groups (—PO—) therein, each representing 0 or a positive integer. In case where both of p and q are not 0, the addition sequence of the cationized ethyleneoxy group and the propyleneoxy group is not defined, and in case where p and/or q are/is 2 or more, a binding form may be any of like a block co-polymer or like a random co-polymer).

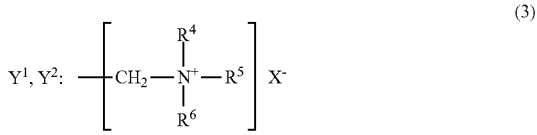

(3)

(In the formula, $R^4$, $R^5$ and $R^6$ each independently represent a linear or branched alkyl group having from 1 to 3 carbon atoms, and $X^-$ represents an anionic group).

(Anhydroglucose-Derived Main Chain Represented by General Formula (1))

In the general formula (1), $R^1$, $R^2$ and $R^3$ each independently represent a substituent represented by the general formula (2), and $R^1$, $R^2$ and $R^3$ may be the same or different. n $R^1$'s, n $R^2$'s and n $R^3$'s each may be the same or different.

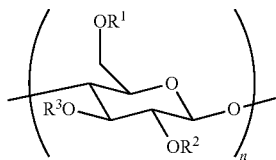

(1)

From the viewpoint of preventing the hair treated with the hair cosmetic of the present invention and dried from having an oily feeling and of imparting good finger combability and manageability to the hair, the mean degree of polymerization n in the general formula (1) is at least 50, preferably at least 100, more preferably at least 200, even more preferably at least 300. From the viewpoint of preventing the hair treated with the hair cosmetic of the present invention and dried from having an oily feeling and of imparting good finger combability and manageability to the hair, and from the viewpoint of easiness in production, the mean degree of polymerization n is at most 5000, preferably at most 3000, more preferably at most 2000, even more preferably at most 1500. Summing up these viewpoints, the mean degree of polymerization n is from 50 to 5000, preferably from 100 to 3000, more preferably from 200 to 2000, even more preferably from 300 to 1500.

In the present invention, the mean degree of polymerization is a viscosity-average degree of polymerization to be determined according to a copper-ammonia process, and is concretely calculated according to the method described in the section of Examples.

(Substituent Represented by General Formula (2))

The substituent represented by the general formula (2) has, as shown in the following formula (2), a cationized ethyleneoxy group and a propyleneoxy group.

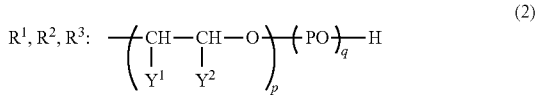

(2)

In the general formula (2), one of $Y^1$ and $Y^2$ is a hydrogen atom and the other is a cationic group represented by the following general formula (3), and PO represents a propyleneoxy group.

p indicates the number of cationized ethyleneoxy groups (($-CH(Y^1)-CH(Y^2)-O-$) in the general formula (2), and is 0 or a positive integer. From the viewpoint of easiness in production, p is preferably an integer of from 0 to 3, more preferably an integer of from 0 to 2, even more preferably 0 or 1.

q indicates the number of propyleneoxy groups ($-PO-$) in the general formula (2), and is 0 or a positive integer. From the viewpoint of easiness in production, q is preferably an integer of from 0 to 4, more preferably an integer of from 0 to 2, even more preferably 0 or 1.

In case where C—HPC has multiple substituents each represented by the general formula (2) in the molecule thereof, the values of p and q may differ between the substituents.

The total of p and q is preferably an integer of from 1 to 5 from the viewpoint of easiness in production, more preferably an integer of from 1 to 4, even more preferably an integer of from 1 to 3, further more preferably 1 or 2.

In case where both of p and q are not 0, the addition sequence of the cationized ethyleneoxy group and the propyleneoxy group is not defined, but from the viewpoint of easiness in production, the addition sequence is preferably as in the general formula (2).

In case where both p and q are not 0 and where p and/or q are/is 2 or more, a binding form may be any of like a block co-polymer or like a random co-polymer, but from the viewpoint of easiness in production, preferred is the binding form like a block co-polymer.

In at least one of n $R^1$'s, n $R^2$'s and n $R^3$'s, p in the general formula (2) is not 0, and in at least one of these, q in the general formula (2) is not 0.

(Cationic Group Represented by General Formula (3))

The cationic group represented by the general formula (3) has the structure shown below.

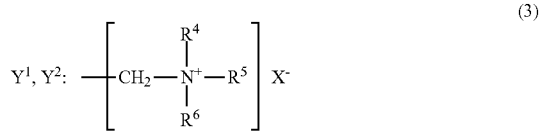

(3)

In the general formula (3), $R^4$, $R^5$ and $R^6$ each independently represent a linear or branched alkyl group having from 1 to 3 carbon atoms, and examples thereof include a methyl group, an ethyl group, an n-propyl group and an isopropyl group. Of those, preferred is a methyl group or an ethyl group from the viewpoint of the solubility of C—HPC in water, and more preferred is a methyl group.

In the general formula (3), $X^-$ represents an anionic group which is a counter ion to the ammonium group. Not specifically defined, $X^-$ may be any anionic group. Specific examples of the group include an alkylsulfate ion, a sulfate ion, a phosphate ion, an alkylcarbonate ion, a halide ion, etc. Of those, preferred is a halide ion from the viewpoint of easiness in production. The halide ion includes a fluoride ion, a chloride ion, a bromide ion and an iodide ion. From the viewpoint of the solubility in water and the chemical stability of C—HPC, preferred is a chloride ion or a bromide ion, and more preferred is a chloride ion.

In C—HPC represented by the general formula (1), the degree of substitution with cationized ethyleneoxy group is at most 2.9, preferably at most 2.5, more preferably at most 2.0, even more preferably at most 1.5, further preferably at most 1.2, from the viewpoint of imparting good finger combability and manageability to the hair treated with the hair cosmetic of the present invention and dried and from the viewpoint of easiness in production. Also preferably, the degree is at least 0.01, preferably at least 0.1, more preferably at least 0.2, even more preferably at least 0.3, further more preferably at least 0.8, from the viewpoint of preventing the hair treated with the hair cosmetic of the present invention and dried from having an oily feeling and of imparting good finger combability and manageability to the hair. Summing up these viewpoints, the degree of substitution with cationized ethyleneoxy group is from 0.01 to 2.9, preferably from 0.1 to 2.5, more preferably from 0.2 to 2.0, even more preferably from 0.3 to 1.5, furthermore preferably from 0.8 to 1.2.

In the present invention, the degree of substitution with cationized ethyleneoxy group means the mean molar number of the cationized ethyleneoxy groups existing in the molecule of C—HPC per mol of the anhydroglucose unit (hereinafter this may be referred to as "AGU") that constitutes the cellulose main chain. The degree of substitution with cationized ethyleneoxy group may be determined according to the method described in the section of Examples given below.

From the viewpoint of preventing the hair treated with the hair cosmetic of the present invention and dried from having an oily feeling and of imparting good finger combability and manageability to the hair, and from the viewpoint of easiness in production, the degree of substitution with propyleneoxy group is at most 4.0, preferably at most 3.0, more preferably at most 2.9, even more preferably at most 2.8, further more preferably at most 2.0. Also from the viewpoint of preventing the hair treated with the hair cosmetic of the present invention and dried from having an oily feeling and of imparting good finger combability and manageability to the hair, the degree is at least 0.1, preferably at least 0.2, more preferably at least 0.3, even more preferably at least 0.6, further preferably at least 1.0. Summing up these viewpoints, the degree of substitution with propyleneoxy group is from 0.1 to 4, preferably from 0.2 to 3.0, more preferably from 0.3 to 2.8, even more preferably from 0.6 to 2.5, furthermore preferably from 1.0 to 2.0.

In the present invention, the degree of substitution with propyleneoxy group means the mean molar number of the propyleneoxy groups existing in the molecule of C—HPC per mol of AGU that constitutes the cellulose main chain. The degree of substitution with propyleneoxy group may be determined according to the method described in the section of Examples given below.

From the viewpoint of easiness in production, the sum of the degree of substitution with cationized ethyleneoxy group and the degree of substitution with propyleneoxy group is preferably at most 3.2, more preferably at most 3.0, even more preferably at most 2.5; and from the viewpoint of improving the finger combability and the manageability of the hair treated with the hair cosmetic of the present invention and dried, the sum is preferably at least 0.9, more preferably at least 1.2, even more preferably at least 1.5. Summing up these viewpoints, the sum of the degree of substitution with cationized ethyleneoxy group and the degree of substitution with propyleneoxy group is preferably from 0.9 to 3.2, more preferably from 1.2 to 3.0, even more preferably from 1.5 to 2.5.

The viscosity of an aqueous 2 mass % solution of C—HPC at 30° C. (hereinafter this may be simply referred to as "2% viscosity") is preferably from 2 to 30000 mPa·s, more preferably from 3 to 25000 mPa·s, even more preferably from 4 to 20000 mPa·s, further more preferably from 5 to 15000 mPa·s, from the viewpoint of the easiness in incorporating the component in the skin cleanser composition and from the viewpoint of the storage stability of the composition. The 2% viscosity is a value to be determined according to the method described in the section of Examples.

From the viewpoint of preventing the hair treated with the hair cosmetic of the present invention and dried from having an oily feeling and of imparting good finger combability and manageability to the hair, the content of C—HPC in the hair cosmetic is preferably at least 0.0001% by mass, more preferably at least 0.001% by mass, even more preferably at least 0.01% by mass, further more preferably at least 0.05% by mass, still more preferably at least 0.07% by mass. Also from the viewpoint of preventing the hair treated with the hair cosmetic of the present invention and dried from having an oily feeling and of imparting good finger combability and manageability to the hair, the content is preferably at most 10% by mass, more preferably at most 5% by mass, even more preferably at most 2% by mass, furthermore preferably at most 1% by mass, still more preferably at most 0.7% by mass. Summing up these viewpoints, the C—HPC content is preferably from 0.0005 to 10% by mass, more preferably from 0.001 to 10% by mass, even more preferably from 0.005 to 5% by mass, further more preferably from 0.01 to 2% by mass, still more preferably from 0.05 to 1% by mass, especially more preferably from 0.07 to 0.7% by mass.

[Production of Cationized Hydroxypropyl Cellulose (C—HPC)]

C—HPC in the present invention can be obtained, for example, according to the following production methods (1) to (3):

(1) A method where cellulose is mixed with a large amount of water and a large excess of an alkali metal hydroxide in slurry and reacted with a cationizing agent and propylene oxide.

(2) A method where dimethylacetamide containing lithium chloride is used as a solvent and cellulose is dissolved therein along with an amine or an alcoholate catalyst added thereto, and reacted with a cationizing agent and propylene oxide.

(3) A method where any excessive water or solvent as in the above (1) or (2) is not used but powdery, pellet-like or chip-like cellulose is reacted with a cationizing agent and propylene oxide in the presence of a base.

In the above-mentioned production methods (1) to (3), any of the reaction with a cationizing agent and the reaction with propylene oxide may be carried out first or the two may be carried out simultaneously.

Of these production methods, preferred is the production method (3) from the viewpoint of easiness in production. Specific examples of the production method for C—HPC according to the method (3) include (3-1) a method of cationizing and hydroxypropylating a cellulose-containing raw material, (3-2) a method of processing a cellulose-containing raw material to give an alkali cellulose and then hydroxypropylating and cationizing the resulting alkali cellulose.

The production method (3) is described concretely hereinunder.

[(3-1) Method of Cationizing and Hydroxypropylating Cellulose-Containing Raw Material]

<Cellulose-Containing Raw Material>

As the cellulose-containing raw material for producing C—HPC, preferably used here is (i) a cellulose-containing raw material having a lowered degree of crystallinity, for example, a low-crystalline powdery cellulose, or (ii) a cellulose-containing raw material having a high degree of crystallinity, for example, pulp.

<(3-1-i) Production of C—HPC Using Cellulose-Containing Raw Material Having Lowered Crystallinity>

(Production of Cellulose-Containing Raw Material Having Lowered Crystallinity)

A cellulose-containing raw material having a lowered crystallinity, for example, a low-crystalline powdery cellulose can be prepared from a sheet-like or a roll-like pulp having a high cellulose purity that is obtained as a general-purpose raw material. The preparing method for low-crystalline powdery cellulose is not specifically defined. For example, there are mentioned the methods described in JP-A 62-236801, 2003-64184, 2004-331918, etc. Of those, more preferred is using a low-crystalline or amorphous powdery cellulose obtained through mechanochemical treatment (hereinafter this may be generically referred to as "low-crystalline powdery cellulose") from the viewpoint of improving the productivity of the cellulose-containing raw material having a lowered crystallinity, for example, the low-crystalline powdery cellulose.

Here the "low crystallinity" of the low-crystalline powdery cellulose means that the cellulose has a large amorphous proportion in the crystal structure thereof. Concretely, from the viewpoint of increasing the reactivity of the material with a cationizing agent and propylene oxide, the degree of crystallinity thereof to be calculated by the math formula (1) mentioned below is preferably at most 30%, more preferably at most 20%, even more preferably at most 10%, and still more preferred is use of a completely amorphous cellulose of which the degree of crystallinity is nearly 0%.

$$\text{Degree of Crystallinity (\%)} = [(I_{22.6} - I_{18.5})/I_{22.6}] \times 100 \quad (1)$$

(In the formula, $I_{22.6}$ means the diffraction intensity at the lattice plane (002 plane) in X-ray diffractiometry (diffraction angle $2\theta=22.6°$, and $I_{18.5}$ means the diffraction intensity at the amorphous moiety (diffraction angle $2\theta=18.5°$).

As the production method for low-crystalline powdery cellulose through mechanochemical treatment, for example, there is mentioned a method of processing a chip-like pulp obtained by roughly grinding a sheet-like pulp, using a grinder. Before the treatment with a grinder, the chip-like pulp may be processed through an extruder.

The extruder to be used in the method may be a single-screw or double-screw extruder, but preferred is a double-screw extruder. From the viewpoint of imparting strong compression shear force, preferred is an extruder equipped with a so-called kneading disc part in any part of the screw.

The processing method with an extruder is not specifically defined. Preferred is a method where a chip-like pulp is put into an extruder and continuously processed therein.

The grinder includes a roll mill such as a high-pressure compression roll mill, a roll-rotating mill, etc.; a vertical roller mill such as a ring roller mill, a roller-less mill, a boll-less mill, etc.; a chamber vibration-mediated mill such as a rotary ball mill, a vibratory ball mill, a vibratory rod mill, a vibratory tube mill, a planetary ball mill, a centrifugal fluidization mill, etc.; a medium stirring mill such as a column grinder, a stirring column mill, a ventilation column mill, an annular mill, etc.; a consolidation shear mill such as a high-speed centrifugal roller mill, an angmill, etc.; a mortar, a stone mill, etc. Of those, preferred is a chamber vibration-mediated mill or a medium stirring mill from the viewpoint of efficiently lowering the degree of crystallinity of cellulose and from the viewpoint of productivity, and more preferred is a chamber vibration-mediated. Even more preferred is a vibration mill such as a vibratory ball mill, a vibratory rod mill, a vibratory tube mill or the like, and still more preferred is a vibratory ball mill or a vibratory rod mill.

The treatment method may be any of a batch process or a continuous process.

The preferred range of the filling rate with media such as balls, rods or the like may vary depending on the type of the grinder, but is preferably within a range of from 10 to 97%, more preferably from 15 to 95%. When the filling rate falls within the range, then the contact frequency between the pulp and the media may increase and the grinding efficiency can be thereby increased without interfering with the movement of media. Here the filling rate means the apparent volume of the media relative to the volume of the stirring area of the grinder.

In the case of a ball mill, the material of the balls to be used as the media is not specifically defined. For example, there may be mentioned iron, stainless, alumina, zirconia, etc. The outer diameter of the ball is preferably from 0.1 to 100 mm, more preferably from 1 to 50 mm from the viewpoint of efficiently lowering the degree of crystallinity of cellulose.

Also from the viewpoint of efficiently lowering the degree of crystallinity of cellulose, the treatment time in a grinder is preferably from 5 minutes to 72 hours, more preferably from 10 minutes to 30 hours. In treatment in a grinder, the temperature is preferably not higher than 250° C., more preferably from 5 to 200° C. from the viewpoint of minimizing the denaturation and degradation owing to heat generation.

Rods for use as the medium in the grinder are rod-shaped media, of which the cross section may be any of polygon such as tetragon, hexagon or the like, as well as circle, oval, etc.

The outer diameter of the rod is preferably from 0.5 to 200 mm, more preferably from 1 to 100 mm, even more preferably from 5 to 50 mm. The length of the rod is not specifically defined so far as it is shorter than the length of the chamber of the grinder. When the rod size falls within the above range, then a desired grinding force can be applied to cellulose by which the degree of crystallinity of the ground cellulose can be efficiently lowered.

Not specifically defined, the treatment time and the treatment temperature in the rods-filled vibration mill may be the same as the treatment time and the treatment temperature in the above-mentioned ball mill.

According to the above-mentioned methods, it is possible to control the molecular weight of cellulose, and a low-crystalline powdery cellulose having a high degree of polymerization and hardly available in general can be readily prepared. The mean degree of polymerization of the low-crystalline powdery cellulose for use herein is preferably from 50 to 5000, more preferably from 100 to 3000, even more preferably from 200 to 2000, further more preferably from 350 to 1500.

The mean particle size of the low-crystalline powdery cellulose is not specifically defined so far as the cellulose can maintain a good flowable state as powder. Preferably, the mean particle size is at most 300 μm, more preferably at most 150 μm, even more preferably at most 50 μm. From the viewpoint of improving the handleability of the powdery cellulose, the mean particle size thereof is preferably at least 20 μm, more preferably at least 25 μm. If desired, for evading mixing with a minor amount of coarse particles owing to aggregation, preferably used in the reaction are undersize particles having passed through a sieve having a sieve opening of from 300 to 1000 μm or so.

(Cationization of Cellulose-Containing Raw Material Having Lowered Crystallinity)

Produced in the manner as above, the cellulose-containing raw material having a lowered degree of crystallinity, for example, the low-crystalline powdery cellulose is reacted with a glycidyltrialkylammonium salt in the presence of a base for cationization to give a cationized cellulose.

The glycidyltrialkylammonium salt to be used as the cationizing agent includes glycidyltrimethylammonium chloride, glycidyltriethylammonium chloride, glycidyltrimethylammonium bromide, glycidyltriethylammonium bromide, etc. From the viewpoint of availability, preferred is glycidyltrimethylammonium chloride.

The amount of the glycidyltrialkylammonium salt to be added is preferably from 0.01 to 8.5 molar times per mol of AGU in cellulose, more preferably from 0.1 to 7 molar times, even more preferably from 0.2 to 5.5 molar times, still more preferably from 0.5 to 4.5 molar times, from the viewpoint of improving the finger combability and the manageability of the hair treated with the hair cosmetic of the present invention and dried.

The base to be present in the system during cationization includes lithium hydroxide, sodium hydroxide, potassium hydroxide, calcium hydroxide, barium hydroxide, etc. From the viewpoint of availability, general versatility and economic potential, more preferred are sodium hydroxide and barium hydroxide.

The amount of the base to be added may vary depending on the type of cellulose, but from the viewpoint of efficiently reacting cellulose and the cationizing agent, the amount is, in general, preferably from 0.05 to 1.0 molar times relative to mol of AGU in cellulose, more preferably from 0.06 to 1.0 molar times, even more preferably from 0.07 to 0.7 molar times, still more preferably from 0.1 to 0.3 molar times.

The water content in the reaction system is preferably at most 100% by mass relative to the cellulose used as the raw material. When the water content relative to the cellulose falls within the range, then the cellulose would not aggregate excessively and therefore can be reacted as a flowable powdery state. From this viewpoint, the water content is preferably at most 80% by mass, more preferably from 5 to 50% by mass.

The reaction temperature is generally from 10 to 85° C., but preferably from 15 to 80° C.

(Hydroxypropylation of Cationized Cellulose)

Produced in the manner as above, the cationized cellulose is reacted with propylene oxide for hydroxypropylation to give C—HPC.

Here the amount of propylene oxide to be used is preferably from 0.01 to 8.5 molar times per mol of AGU in the cellulose molecule, more preferably from 0.1 to 5.0 molar times, even more preferably from 1.0 to 3.0 molar times, from the viewpoint of improving the finger combability and the manageability of the hair treated with the hair cosmetic of the present invention and dried and preventing the hair from having an oily feeling.

As the catalyst for the hydroxypropylation, usable is a base or an acid. The base catalyst includes alkali metal hydroxides such as sodium hydroxide, potassium hydroxide, lithium hydroxide, etc.; alkaline earth metal hydroxides such as magnesium hydroxide, calcium hydroxide, etc.; tertiary amines such as trimethylamine, triethylamine, triethylenediamine, etc. The acid catalyst includes Lewis acid catalysts such as lanthanide triflates, etc.

Of those, preferred is a base catalyst from the viewpoint of preventing the degree of polymerization of cellulose in the cellulose-containing staring material from lowering, and more preferred is an alkali metal hydroxide. Even more preferred is sodium hydroxide or potassium hydroxide. One or more different types of these catalysts may be used here either singly or as combined.

Not specifically defined, the amount of the catalyst to be used is, in general, preferably from 0.05 to 1.0 molar times per mol of AGU in the cellulose molecule, more preferably from 0.07 to 0.7 molar times, even more preferably from 0.1 to 0.3 molar times. In case where the cationization step is carried out first, the base used in the cationization step may be used as such as the catalyst in the hydroxypropylation, and addition of any additional catalyst may be omitted in the hydroxypropylation step.

The method of adding propylene oxide is not specifically defined. For example, there are mentioned (a) a method of adding a catalyst to the cationized cellulose and then dropwise adding propylene oxide thereto, and (b) a method adding propylene oxide to the cationized cellulose all at a time and thereafter gradually adding thereto a catalyst to lead the reaction. More preferred is the method (a).

The water content in the reaction system is preferably at most 100% by mass relative to the cellulose used as the raw material. When the water content relative to the cellulose falls within the range, then the cationized cellulose would not aggregate excessively and therefore can be reacted as a flowable powdery state. From this viewpoint, the water content is preferably at most 80% by mass, more preferably from to 50% by mass.

In the present invention, preferably, the cationized cellulose, the catalyst and the propylene oxide are reacted in a flowable powdery state. If desired, the cationized cellulose powder and the catalyst may be previously uniformly mixed and dispersed in a mixing apparatus such as a mixer or the like or by the use of a shaking machine, a mixing mill or the like, and thereafter propylene oxide may be added thereto and reacted.

Preferably, the reaction temperature in hydroxypropylation is from 0 to 150° C.; however, from the viewpoint of preventing polymerization of propylene oxide and preventing any rapid reaction, the temperature is more preferably from 10 to 100° C., even more preferably from 20 to 80° C. The reaction may be carried out under normal pressure.

From the viewpoint of evading the reduction in the molecular weight owing to cleavage of the cellulose chains during the reaction, it is desirable to carry out the reaction in an inert gas atmosphere such as nitrogen, etc.

After the reaction, the unreacted propylene oxide is removed, and thereafter if desired, the system is neutralized, then purified and dried to give C—HPC for use in the present invention.

The neutralization may be carried out under normal pressure. For example, in case where a base catalyst is used, a liquid acid such as acetic acid or the like, or a mixed solution of an acid and an inert organic solvent, or an aqueous acid solution may be added to the system for neutralization. The type of the acid is not specifically defined, and the acid may be suitably selected in consideration of corrosion of apparatus, etc. The purification may be carried out by the use of a solvent such as water-containing isopropanol, water-containing acetone solvent or the like and/or by washing with water, or through a dialytic membrane.

Regarding the sequence of the cationization and the hydroxypropylation in the above-mentioned <(3-1-i) Production of C—HPC using cellulose-containing raw material having lowered crystallinity>, the cellulose in the cellulose-containing raw material may be first hydroxypropylated and then cationized, or may be hydroxypropylated and cationized at one time.

From the viewpoint of controlling the degree of substitution with cationized ethyleneoxy group and propyleneoxy group, preferably, the cellulose-containing raw material (starting cellulose) is first cationized and then hydroxypropylated.

For the purpose of increasing the degree of substitution with cationized ethyleneoxy group, the cationized and hydroxypropylated system may be further again cationized.

In the cationization step and the hydroxypropylation step in the above-mentioned <(3-1-i) Production of C—HPC using cellulose-containing raw material having lowered crystallinity>, the cellulose skeleton to be the main chain is not substantially cleaved, and therefore the mean degree of polymerization of the C—HPC to be obtained could be approximated by the mean degree of polymerization of the cellulose raw material having a lowered crystallinity, for example, powdery cellulose treated for lowering the crystallinity thereof.

<(3-1-ii) Production of C—HPC Using Cellulose-Containing Raw Material Having High Crystallinity>

(Cationization of Cellulose-Containing Raw Material Having High Crystallinity)

In case where a cellulose-containing raw material having a high crystallinity, for example, pulp (hereinafter the cellulose-containing raw material is typically pulp) is used as the cellulose-containing raw material, not using the above-mentioned cellulose-containing raw material having lowered crystallinity, for example, the low-crystalline powdery cellulose, preferably, the cellulose-containing raw material is processed for crystallinity reduction in cationization for the purpose of improving the reactivity of the material.

Concretely, a cationizing agent is added to the cellulose-containing raw material and treated in a grinder for crystallinity reduction, and thereafter a base is added thereto and treated in a grinder for crystallinity reduction while the cellulose-containing raw material is reacted with a cationizing agent thereby giving a cationized cellulose; or a base is added to the cellulose-containing raw material and treated in a grinder for crystallinity reduction, and thereafter a cationizing agent is added thereto and treated in a grinder for crystallinity reduction along with reaction of the cellulose-containing raw material and the cationizing agent thereby giving a cationized cellulose. From the viewpoint of obtaining C—HPC having a high degree of substitution with cationized ethyleneoxy group, preferably, a cationizing agent is added to the cellulose-containing raw material and treated in a grinder, and thereafter a base is added thereto and treated in a grinder, and further a cationizing agent is added thereto and treated in a grinder. Addition of the cationizing agent after addition of the base may be carried out in multiple stages.

From the viewpoint of the solubility in water of the C—HPC obtained through the cationization, in cationization of cellulose, preferably, a cationizing agent is first added to the cellulose-containing raw material and treated in a grinder for crystallinity reduction, and thereafter a base is added thereto and treated in a grinder for crystallinity reduction along with reaction of the cellulose-containing raw material and the cationizing agent.

The cellulose-containing raw material having a high crystallinity includes various types of wood chips; pulps such as wood pulp produced from wood, cotton linter pulp obtained from fibers around cotton seeds, etc.; papers such as newspaper, cardboard, magazine, high-quality paper, etc.; plant stems and leaves such as rice straws, corn stems, etc.; plant shells such as rice husks, palm shells, coconut husks, etc. From the viewpoint of high cellulose purity and productivity of C—HPC, preferred is wood pulp.

The shape of the pulp to be used as the cellulose-containing raw material is not specifically defined so far as not interfering with the introduction thereof into a production apparatus, but from the viewpoint of handleability thereof, preferred is use of sheet-like pulp, or pellet-like or chip-like pulp produced by cutting or roughly grinding sheet-like pulp, or powdery cellulose obtained by finely pulverizing pulp.

The degree of crystallinity of the pulp for use as the cellulose-containing raw material is not defined. However, in general, the treatment of cellulose for crystallinity reduction is accompanied by molecular weight reduction owing to cleavage of cellulose chains, and therefore the cellulose in the cellulose-containing raw material having a low crystallinity has a low molecular weight. Consequently, from the viewpoint of obtaining C—HPC having a high molecular weight, preferred is used of cellulose having a high crystallinity. On the contrary, cellulose having an extremely high crystallinity of more than 95%, as calculated according to the above-mentioned math formula (1), is hardly available. Accordingly, from the viewpoint of the degree of polymerization and the availability, the degree of crystallinity calculated according to the above-mentioned math formula (1) of the cellulose in the cellulose-containing raw material is preferably from 10 to 95%, more preferably from 30 to 90%, even more preferably from 60 to 80%.

The mean degree of polymerization of the cellulose in the cellulose-containing raw material is not defined; however, from the viewpoint of obtaining C—HPC having a high molecular weight, preferred is used of a cellulose having a larger degree of polymerization. From this viewpoint, the mean degree of polymerization of the cellulose in the cellulose-containing raw material is preferably from 50 to 5000, more preferably from 100 to 2000.

Preferred embodiments of the type and the amount of the cationizing agent, the type of the base, the type of the grinder, and the method and the condition for crystallinity reduction are the same as those described in the section of the above-mentioned <(3-1-i) Production of C—HPC using cellulose-containing raw material having lowered crystallinity>, except the treatment time with grinder for crystallinity reduction and the amount of the base.

The treatment time with grinder for crystallinity reduction is preferably from 1 minute to 5 hours, more preferably from 2 minutes to 3 hours, even more preferably from 5 minutes to 2 hours, from the viewpoint of efficiently lowering the degree of crystallinity of the treated cellulose while preventing the degree of polymerization thereof from lowering.

The amount of the base is preferably from 0.05 to 1.5 molar times per mol of AGU in the cellulose in the cellulose-containing raw material, more preferably from 0.07 to 1.0 molar times, even more preferably from 0.1 to 0.6 molar times, from the viewpoint of efficiently reacting the cellulose with the cationizing agent.

The cationization may go on after addition of the cationizing agent and the base for crystallinity reduction, however, when the reaction is insufficient, it is desirable that the system is ripened at from 10 to 100° C., more preferably from 30 to 80° C. for promoting the reaction.

Even though the cationization is insufficient, a glycidyltrialkylammonium salt may be added to the system to ripen it, whereby a cationized cellulose having a high degree of substitution with cationized ethyleneoxy group can be obtained.

The amount of water in ripening and other preferred embodiments are the same as those for the above-mentioned cationization of low-crystalline powdery cellulose, except the point that a cellulose-containing raw material having a high degree of crystallinity is used in place of the low-crystalline powdery cellulose as the raw material.

From the viewpoint of evading the reduction in the molecular weight owing to cleavage of cellulose chains during reaction, the reaction is preferably carried out in an inert gas atmosphere such as nitrogen, etc.

(Hydroxypropylation of Cationized Cellulose)

The amount of propylene oxide to be used for hydroxypropylation of cationized cellulose in <(3-1-ii) Production of C—HPC using cellulose-containing raw material having high crystallinity: Method (a)>, as well as the catalyst, the reaction condition, the treatment after the reaction and other preferred embodiments are the same as those described for the hydroxypropylation in the above-mentioned <(3-1-i) Production of C—HPC using cellulose-containing raw material having lowered crystallinity>.

Regarding the sequence of cationization and hydroxypropylation in the above-mentioned <(3-1-ii) Production of C—HPC using cellulose-containing raw material having high crystallinity: Method (a)>, the hydroxypropylation of the cellulose-containing raw material may be carried out first and then the cationization may be carried out, or the two may be carried out simultaneously. From the viewpoint of controlling the degree of substitution with cationized ethyleneoxy group and propyleneoxy group, preferably, the cellulose-containing raw material is first cationized and then hydroxypropylated.

From the viewpoint of increasing the degree of substitution with cationized ethyleneoxy group, the cationized and hydroxypropylated system may be further again cationized.

[(3-2) Method of Processing Cellulose-Containing Raw Material to Give Alkali Cellulose and then Cationizing and Hydropropylating the Resulting Alkali Cellulose]
<Cellulose-Containing Raw Material>

As the cellulose-containing raw material for producing C—HPC, preferably used here is (i) a cellulose-containing raw material having a lowered degree of crystallinity or (ii) a cellulose-containing raw material having a high degree of crystallinity, like in [(3-1) Method of cationizing and hydroxypropylating cellulose-containing raw material].

<(3-2-i) Production of C—HPC Using Cellulose-Containing Raw Material Having Lowered Crystallinity: Method (b)>
(Production of Cellulose-Containing Raw Material Having Lowered Crystallinity)

The cellulose-containing raw material having a lowered crystallinity is the same as that described in <(3-1-i) Production of C—HPC using cellulose-containing raw material having lowered crystallinity>.

From the viewpoint of improving the productivity of the cellulose-containing raw material having a lowered crystallinity, preferred is one to be produced by grinding a high-crystalline cellulose-containing raw material, for example, wood pulp.

The degree of crystallinity of the cellulose-containing raw material having a lowered crystallinity is preferably from 10 to 50%, more preferably from 10 to 40%, even more preferably from 10 to 30%, from the viewpoint of increasing the reactivity between the alkali cellulose to be mentioned below and the cationizing agent and propylene oxide and from the viewpoint of increasing the degree of polymerization of the cellulose-containing raw material.

(Treatment of Cellulose-Containing Raw Material Having Lowered Crystallinity to Give Alkali Cellulose)

The cellulose-containing raw material having a lowered crystallinity is mixed with a base and water to give an alkali cellulose.

The base includes alkali metal hydroxides such as sodium hydroxide, potassium hydroxide, lithium hydroxide, etc.; alkaline earth metal hydroxides such as magnesium hydroxide, calcium hydroxide, etc.; tertiary amines such as trimethylamine, triethylamine, triethylenediamine, etc. Of those, preferred is an alkali metal hydroxide or an alkaline earth metal hydroxide. Even more preferred is an alkali metal hydroxide; and still more preferred is sodium hydroxide or potassium hydroxide. One or more different types of these bases may be used here either singly or as combined.

The amount of the base is preferably from 0.6 to 1.5 mols per mol of AGU that constitutes the cellulose in the cellulose-containing raw material, more preferably from 0.7 to 1.3 mols, even more preferably from 0.8 to 1.2 mols, from the viewpoint of increasing the yield of the alkali cellulose and from the viewpoint of improving the reactivity of the alkali cellulose and the cationizing agent and propylene oxide to be mentioned below.

The amount of water to be added is preferably from 20 to 100% by mass of the cellulose in the cellulose-containing raw material, more preferably from 25 to 70% by mass, even more preferably from 30 to 60% by mass, from the viewpoint of increasing the yield of the alkali cellulose and from the viewpoint of improving the reactivity of the alkali cellulose and the cationizing agent and propylene oxide to be mentioned below.

The method of mixing the cellulose-containing raw material having lowered crystallinity with a base and water is not specifically defined, but from the viewpoint of increasing the productivity, it is desirable to add a base and water to the cellulose-containing raw material having lowered crystallinity. Regarding the addition mode, all the components may be added at a time to the reactor, or divided portions thereof may be added thereto intermittently. As the case may be, a base and water may be previously mixed, and the resulting mixture may be sprayed onto the cellulose-containing raw material.

Not specifically defined, the mixing apparatus may be any one where a base can be dispersed in the cellulose-containing raw material. For example, there are mentioned various mixing machines such as a ribbon-type mixer, a paddle-type mixer, a conical planetary screw-type mixer, a kneader, etc. Of those, more preferred is a horizontal screw-type paddle mixer, concretely a Ledige mixer that is a horizontal screw-type paddle mixer having chopper paddles.

After the cellulose-containing raw material having lowered crystallinity has been mixed with a base and water, the resulting mixture is preferably ripened from the viewpoint of increasing the speed of producing the alkali cellulose. The ripening temperature is preferably from 35 to 90° C., more preferably from 38 to 80° C., even more preferably from 40 to 70° C. The ripening time is preferably from 0.1 to 24 hours, more preferably from 0.5 to 12 hours, even more preferably from 1 to 6 hours.

The change from the cellulose-containing raw material to alkali cellulose can be confirmed through X-ray crystal diffractiometry.

(Hydroxypropylation of Alkali Cellulose)

Preferred embodiments of the amount of propylene oxide, the type of catalyst, the amount of catalyst and the reaction condition in hydroxypropylation of alkali cellulose are the same as those described in (hydroxypropylation) in the above-mentioned <(3-1-i) Production of C—HPC using cellulose-containing raw material having lowered crystallinity>.

(Cationization of Hydroxypropyl Cellulose)

Preferred embodiments of the type of the cationizing agent, the amount of the cationizing agent, the type of the catalyst, the amount of the catalyst and the reaction condition in cationization of hydroxypropyl cellulose are the same as those described in (cationization) in the above-mentioned <(3-1-i) Production of C—HPC using cellulose-containing raw material having lowered crystallinity>.

<(3-2-ii) Production of C—HPC Using Cellulose-Containing Raw material having high crystallinity: Method (c)>
(Treatment of Cellulose-Containing Raw Material to Give Alkali Cellulose)

The cellulose-containing raw material is treated in a grinder along with a base and substantially with no water thereinto give a ground cellulose/base mixture, which is then mixed with water to give an alkali cellulose.

Preferred embodiments of the type, the shape, the degree of crystallinity and the mean degree of polymerization of the cellulose-containing raw material are the same as those in the section of (cationization of high-crystalline cellulose-containing raw material) in the above-mentioned Method (a).

Preferred embodiments of the type of the base compound, and the amount of the base are the same as those in the section of (treatment into alkali cellulose) in the above-mentioned Method (b).

From the viewpoint of reducing the water content during grinding, preferably, the base is mixed with the cellulose material in the absence of water therein.

Preferably, the treatment in the grinder is carried out substantially in the absence of water therein. Specifically, from the viewpoint of improving the grinding efficiency and the productivity such as the easiness in water removal, the water content in the system is preferably at most 10% by mass relative to the cellulose-containing raw material, more preferably from 0.01 to 8% by mass, even more preferably from 0.1 to 6% by mass, furthermore preferably from 1 to 5% by mass.

Preferred embodiments of the type of the grinder and the grinding condition are the same as those described in the section of (production of cellulose-containing raw material having lowered crystallinity) in the above-mentioned <(3-1-i) Production of C—HPC using cellulose-containing raw material having lowered crystallinity>.

From the viewpoint of increasing the speed in producing alkali cellulose, from the viewpoint of increasing the yield of alkali cellulose, and from the viewpoint of preventing the mean degree of polymerization of cellulose from lowering, preferably, the cellulose/base mixture is ground so that the mean particle size of the cellulose in the ground cellulose/base mixture could be from 10 to 150 μm, more preferably from 20 to 130 μm, even more preferably from 40 to 100 μm, still more preferably from 50 to 80 μm. The mean particle size of the ground cellulose/base mixture may be determined according to the method described in the section of Examples.

From the viewpoint of increasing the yield of alkali cellulose, and from the viewpoint of enhancing the reactivity between alkali cellulose and the cationizing agent and propylene oxide to be mentioned below, preferably, water is mixed with the ground cellulose/base mixture in such a manner that the water content in the ground cellulose/base mixture could be from 30 to 100% by mass relative to the cellulose in the cellulose-containing raw material, more preferably from 35 to 70% by mass, even more preferably from 40 to 60% by mass.

(Hydroxypropylation of Alkali Cellulose)

Preferred embodiments of the amount of propylene oxide, the type of the catalyst, the amount of the catalyst and the reaction condition in hydroxypropylation of alkali cellulose are the same as those described in the section of (hydroxypropylation) in the above-mentioned <(3-1-i) Production of C—HPC using cellulose-containing raw material having lowered crystallinity>.

(Cationization of Hydroxypropyl Cellulose)

Preferred embodiments of the type of the cationizing agent, the amount of the cationizing agent, the type of the catalyst, the amount of the catalyst and the reaction condition in hydroxypropylation of alkali cellulose are the same as those described in the section of (cationization) in the above-mentioned <(3-1-i) Production of C—HPC using cellulose-containing raw material having lowered crystallinity>.

The reaction sequence of the hydroxypropylation and the cationization in the above-mentioned methods (b) and (c) may be transposed, but from the viewpoint of increasing the degree of substitution with cationized ethyleneoxy group, the reaction order is the hydroxypropylation first followed by the cationization.

The production method for C—HPC for use in the present invention is preferably the method (method (a) mentioned below) of <(3-1-ii) Production of C—HPC using cellulose-containing raw material having high crystallinity> in the above-mentioned method (3-1), or the method (method (b) or (c) mentioned below) described in (3-2), from the viewpoint of improving the finger combability and the manageability of the hair treated with the hair cosmetic of the present invention and dried.

Concretely, C—HPC is preferably one obtained according to the method including the following steps (a-1) to (a-3), or the method including the following step (a-4) and (a-5), or the method including the following steps (b-1) to (b-4), or the method including the following steps (c-1) to (c-4), from the viewpoint of improving the finger combability and the manageability of the hair treated with the hair cosmetic of the present invention and dried, and is more preferably one obtained according to the method (a) mentioned below and including the steps (a-1) to (a-3), or one obtained according to the method (b) mentioned below and including the steps (b-1) to (b-4), or one obtained according to the method (c) mentioned below and including the steps (c-1) to (c-4).

Method (a):

Step (a-1): a step of adding a cationizing agent to a cellulose-containing raw material and processing it with a grinder.

Step (a-2): a step of adding a base to the grinder-processed product obtained in the step (a-1), and while processing it with a grinder, reacting the cellulose-containing raw material and the cationizing agent to give a cationized cellulose.

Step (a-3): a step of reacting the cationized cellulose obtained in the step (a-2) with propylene oxide to give a cationized hydroxypropyl cellulose (A).

Step (a-4): a step of adding a base to a cellulose-containing raw material and processing it with a grinder for crystallinity reduction, and thereafter while a cationizing agent is added thereto and processing it with a grinder for crystallinity reduction, reacting the cellulose-containing raw material and the cationizing agent to give a cationized cellulose.

Step (a-5): a step of reacting the cationized cellulose obtained in the step (a-4) with propylene oxide to give a cationized hydroxypropyl cellulose.

Method (b):

Step (b-1): a step of processing a cellulose-containing raw material with a grinder to give a cellulose-containing raw material that contains a cellulose having a degree of crystallinity of from 10 to 50%.

Step (b-2): a step of adding to the cellulose-containing raw material obtained in the step (b-1), a base in an amount of from 0.6 to 1.5 molar times per mol of AGU that constitutes the cellulose in the cellulose-containing raw material, and water in an amount of from 20 to 100% by mass relative to the cellulose in the cellulose-containing raw material, thereby giving an alkali cellulose.

Step (b-3): a step of reacting the alkali cellulose obtained in the step (b-2) and propylene oxide to give a hydroxypropyl cellulose.

Step (b-4): a step of reacting the hydroxypropyl cellulose obtained in the step (b-3) with a cationizing agent to give the cationized hydroxypropyl cellulose (A).

Method (c):

Step (c-1): a step of processing a mixture of a cellulose-containing raw material and a base in an amount of from 0.6 to 1.5 molar times per mol of AGU that constitutes the cellulose in the cellulose-containing raw material, with a grinder under the condition where the water content in the cellulose-containing raw material is at most 10% by weight relative to the cellulose therein, thereby giving a ground cellulose/base mixture in which the mean particle size of the cellulose is from 10 to 150 μm.

Step (c-2): a step of adding water to the ground cellulose/base mixture obtained in the step (c-1) to thereby control the water content in the ground cellulose/base mixture to be from 30 to 100% by mass relative to the cellulose in the cellulose-containing raw material used in the step (c-1), thereby giving an alkali cellulose.

Step (c-3): a step of reacting the alkali cellulose obtained in the step (c-2) with propylene oxide to give a hydroxypropyl cellulose.

Step (c-4): a step of reacting the hydroxypropyl cellulose obtained in the step (c-3) with a cationizing agent to give a cationized hydroxypropyl cellulose (A).

(Oil (B) of which the Amount of Dissolution in 100 g of Water at 20° C. is from 0 to 1 g>

The component (B) for use in the present invention, oil (B) of which the amount of dissolution in 100 g of water at 20° C. is from 0 to 1 g may be any hardly water-soluble or water-insoluble oily component which is generally used in medicines, quasi-drugs, cosmetics, toiletries, sundries and the like and of which the amount of dissolution in 100 g of water at 20° C. is from 0 to 1 g. The oil (B) can impart extremely excellent manageability to the hair treated with the hair cosmetic of the present invention and dried.

Specific examples of the oil (B) include (i) ester oils, (ii) silicone oils, (iii) ether oils, (iv) hydrocarbon oils, (v) higher alcohols, (vi) carboxylic acids with a hydrocarbon group having from 17 to 23 carbon atoms and optionally substituted with a hydroxyl group and the like, of which the amount of dissolution in 100 g of water at 20° C. is from 0 to 1 g.

As the ester oils (i), preferred are ester oils represented by the following general formula (11) or (12), and hydrophobic carboxylate esters of dipentaerythritol, from the viewpoint that the hair cosmetic of the present invention can impart good finger combability and manageability to the hair treated therewith and dried.

$$R^{21}-COO-R^{22} \qquad (11)$$

(In the formula, $R^{21}$ represents a linear or branched alkyl group having from 8 to 22 carbon atoms. $R^{22}$ represents a linear or branched alkyl or alkenyl group having from 1 to 22 carbon atoms).

In the general formula (11), the carbon number of $R^{21}$ is preferably from 10 to 20, more preferably from 12 to 18, from the viewpoint of the manageability of hair. From the same viewpoint, the carbon number of $R^{22}$ is preferably from 1 to 20, more preferably from 1 to 18. $R^{22}$ is more preferably a linear or branched alkyl or alkenyl group having from 1 to 18 carbon atoms and optionally interrupted by a propyleneoxy group or a phenyl group.

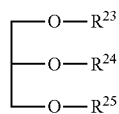
(12)

(In the formula, $R^{23}$, $R^{24}$ and $R^{25}$ each independently represent a hydrogen atom or a group represented by the following general formula (13), but all of these are not hydrogen atoms at the same time).

(13)

(In the formula, $R^{26}$ represents a linear or branched alkyl or alkenyl group having from 8 to 22 carbon atoms, which may be interrupted by a carboxylate ester group and which may be substituted with a hydroxyl group.)

In the general formula (13), the carbon number of $R^{26}$ is preferably from 8 to 20, more preferably from 8 to 18 from the viewpoint of the manageability of hair.

Specific examples of the ester oils (i) represented by the general formula (11) or (12) include castor oil, cacao oil, mink oil, avocado oil, olive oil, sunflower oil, camellia oil, apricot oil, almond oil, wheat germ oil, theobroma grandiflorum seed oil, grape seed oil, babassu oil, jojoba oil, macadamia nut oil, tea seed oil, shea butter oil, camellia reticulata oil, meadowfoam oil, bees wax, lanolin, reduced lanolin, lanolin fatty acid octyldodecyl, caprylyl eicosenoate, dimer acid diisopropyl, myristyl 2-ethylhexanoate, cetyl 2-ethylhexanoate, stearyl 2-ethylhexanoate, octyl octanoate, lauryl octanoate, myristyl octanoate, isocetyl octanoate, octyl propylheptanoate, cetostearyl isononanoate, isononyl isononanoate, isotridecyl isononanoate, methyl laurate, hexyl laurate, octyl laurate, isopropyl myristate, octyl myristate, myristyl myristate, octyldodecyl myristate, isopropyl palmitate, 2-ethyllhexyl palmitate, octyl palmitate, cetyl palmitate, methyl oleate, oleyl oleate, decyl oleate, isobutyl oleate, methyl stearate, 2-ethylhexyl stearate, octyl stearate, isocetyl stearate, stearyl stearate, butyl stearate, isotridecyl stearate, isopropyl isostearate, isocetyl isostearate, isostearyl isostearate, propylene glycol isostearate, 2-ethylhexyl hydroxystearate, oleyl erucate, propane diol dicaprylate, diisopropyl adipate, dimethoxyethyl succinate, 2-ethylhexyl succinate, poly-soybean fatty acid sucrose, polysucrose behenate, sucrose tetraisostearate, glyceryl tribehanate, hydroxyalkyl (C16-18) hydroxydimer dilinoleyl ether, triisostearin, pentaerythrityl tetrastearate, etc.

Of those, preferred are sunflower oil, avocado oil, camellia oil, macadamia nut oil, Shea butter oil, octyl laurate, octyl myristate, octyldodecyl myristate, isopropyl myristate, myristyl myristate, isopropyl palmitate, 2-ethylhexyl palmitate, octyl palmitate, cetyl palmitate, methyl stearate, 2-ethylhexyl stearate, octyl stearate, isocetyl stearate, stearyl stearate, butyl stearate and isotridecyl stearate, from the viewpoint that the hair cosmetic of the present invention can impart good finger combability and manageability to the hair treated therewith and dried. More preferred is at least one selected from sunflower oil, avocado oil, camellia oil, macadamia nut oil, shea butter oil, octyl laurate, octyl myristate, myristyl myristate, isopropyl palmitate, octyl palmitate, cetyl palmitate, octyl stearate, isocetyl stearate, stearyl stearate, isostearyl stearate and isostearyl isostearate.

Hydrophobic carboxylate esters of dipentaerythritol are meant to indicate compounds to be obtained through dehydrating condensation of dipentaerythritol and at least one hydrophobic carboxylate. Here the hydrophobic carboxylic acid is a carboxylic acid with a hydrocarbon group having from 16 to 24 carbon atoms and optionally having a hydroxyl group. Specific examples of the hydrophobic carboxylic acid include palmitic acid, stearic acid, oleic acid, isostearic acid, hydroxystearic acid, rosin acid, etc.

From the viewpoint of availability, preferred is an ester of a mixed acid of hydroxystearic acid, stearic acid and rosin acid, with dipentaerythritol.

As the silicone oil (ii), preferred is at least one selected from dimethylpolysiloxane, dimethiconol (dimethylpolysiloxane having a hydroxyl group at the terminal thereof), and amino-modified silicone (dimethylpolysiloxane having an amino group in the molecule), polyether-modified silicone, glyceryl-modified silicone, amino derivative silicone, silicone wax and silicone elastomer, from the viewpoint that the hair cosmetic of the present invention can impart good finger combability and manageability to the hair treated therewith and dried.

The viscosity of the silicone oil (ii) is preferably from to 15,000,000 mm²/sec from the viewpoint of the finger combability and the manageability of hair and from the viewpoint of the dispersibility of the hair cosmetic during preparation.

As the ether oil (iii), preferred are those represented by the following general formula (14) from the viewpoint of good finger combability and manageability of the hair treated with the hair cosmetic of the present invention and dried.

$$R^{27}\text{—}O\text{—}(PO)_t(EO)_u\text{—}H \quad (14)$$

(In the formula, $R^{27}$ represents a linear or branched alkyl or alkenyl group having from 6 to 22 carbon atoms. PO represents a propyleneoxy group, EO represents an ethyleneoxy group. The mean addition molar number t of PO indicates a number of from 0.1 to 15, and the mean addition molar number u of EO indicates a number of from 0 to 10. In case where u is not 0, then the addition configuration with PO and EO may be any or random addition or block addition, and the addition sequence of PO and EO is not defined.)

In the general formula (14), the carbon number of $R^{27}$ is preferably from 6 to 20, more preferably from 6 to 18, even more preferably from 8 to 18 from the viewpoint of hair manageability.

The mean addition molar number t is preferably from 1 to 15, more preferably from 2 to 13.

Specific examples of the ether oils (iii) include polyoxypropylene hexyl ether, polyoxypropylene octyl ether, polyoxypropylene 2-ethylhexyl ether, polyoxypropylene decyl ether, polyoxypropylene isodecyl ether, polyoxypropylene lauryl ether, polyoxypropylene myristyl ether, polyoxypropylene palmityl ether, polyoxypropylene cetyl ether, polyoxypropylene stearyl ether, polyoxypropylene isostearyl ether, polyoxypropylene octyldecyl ether, polyoxypropylene eicosyl ether, polyoxypropylene behenyl ether and the like, in which the mean addition molar number of the propyleneoxy groups is from 3 to 15.

Of those, more preferred is at least one selected from polyoxypropylene octyl ether, polyoxypropylene decyl ether and polyoxypropylene lauryl ether, in which the mean addition molar number of the propyleneoxy groups is from 3 to 10, from the viewpoint of good finger combability and manageability of the hair treated with the hair cosmetic of the present invention and dried.

As the hydrocarbon oil (iv), preferred are saturated or unsaturated hydrocarbons having at least 20 carbon atoms from the viewpoint of good manageability of the hair treated with the hair cosmetic of the present invention and dried.

Specific examples of the hydrocarbon oil (iv) include squalene, squalane, liquid paraffin, liquid isoparaffin, heavy liquid isoparaffin, α-olefin oligomer, cycloparaffin, polybutene, vaseline, paraffin wax, microcrystalline wax, polyethylene wax, ceresin. From the viewpoint of manageability of hair, preferred are squalane, squalene, liquid paraffin and paraffin wax; and more preferred is at least one selected from squalane, liquid paraffin and paraffin wax.

As the higher alcohol (v), preferred are alcohols having a linear or branched alkyl or alkenyl group with from 6 to 22 carbon atoms from the viewpoint of the manageability of the hair treated with the hair cosmetic of the present invention and dried, in which the carbon number of the alkyl or alkenyl group is more preferably from 8 to 20, even more preferably from 12 to 18.

Specific examples of the higher alcohols (v) include hexyl alcohol, 2-ethylhexyl alcohol, octyl alcohol, decyl alcohol, isodecyl alcohol, lauryl alcohol, myristyl alcohol, palmityl alcohol, cetyl alcohol, stearyl alcohol, isostearyl alcohol, 2-octyldodecanol, eicosyl alcohol, behenyl alcohol.

Of those, preferred are lauryl alcohol, myristyl alcohol, cetyl alcohol, stearyl alcohol, behenyl alcohol and 2-octyldodecanol from the viewpoint of the finger combability and the manageability of hair; more preferred are lauryl alcohol, myristyl alcohol, cetyl alcohol, stearyl alcohol and 2-octyldodecanol; and even more preferred is at least one selected from cetyl alcohol, stearyl alcohol and 2-octyldodecanol.

The hydrocarbon group in the carboxylic acid (vi) with a hydrocarbon group having from 17 to 23 carbon atoms and optionally substituted with a hydroxyl group is preferably a linear or branched alkyl or alkenyl group.

Specific examples of the carboxylic acid with a hydrocarbon group having from 17 to 23 carbon atoms and optionally substituted with a hydroxyl group include stearic acid, oleic acid, isostearic acid, hydroxystearic acid, behenic acid, rosin acid, etc. Of those, preferred are stearic acid, oleic acid, isostearic acid, hydroxystearic acid and behenic acid from the viewpoint of finger combability and manageability of hair; and more preferred are oleic acid and isostearic acid.

From the viewpoint of preventing the hair treated with the hair cosmetic of the present invention and dried from having an oily feeling and of improving the finger combability and manageability to the hair, preferably, the hair cosmetic contains, as the oil (B), at least one compound selected from ester compounds represented by the following general formula (4), dialkyl carbonate compounds represented by the following general formula (5) and dialkyl ether compounds represented by the following general formula (6).

(Ester Compounds Represented by General Formula (4))

Ester compounds represented by the following general formula (4) are ester compounds to be obtained through esterification of an aromatic alcohol alkylene oxide adduct and an aliphatic carboxylic acid.

$$R^7O\text{-}(AO)_m\text{—}COR^8 \quad (4)$$

(In the formula, $R^7$ represents a hydrocarbon group having from 6 to 20 carbon atoms and containing at least one substituted or unsubstituted aromatic ring; $R^8$ represents a linear or branched alkyl or alkenyl group having from 1 to 25 carbon atoms. AO represents an alkyleneoxy group having from 2 to 4 carbon atoms; m indicates a number of from 1 to 50. In case where m is 2 or more, m's AO groups may be the same or different.)

$R^7$ in the general formula (4) is preferably an aromatic hydrocarbon group having from 6 to 12 carbon atoms, more preferably an aromatic hydrocarbon group having from 6 to 10 carbon atoms, even more preferably a benzyl group, from the viewpoint of preventing the hair treated with the hair cosmetic of the present invention and dried from having an oily feeling and of imparting good finger combability and manageability to the hair.

From the same viewpoint as above, $R^8$ is preferably an alkyl group having from 7 to 21 carbon atoms, more preferably an alkyl group having from 11 to 15 carbon atoms.

Also from the same viewpoint as above, the AO group is preferably a propyleneoxy group, and m is preferably from 1 to 10, more preferably from 1 to 5.

Preferred examples of the ester compound represented by the general formula (4) include an ester of myristic acid with benzyl alcohol propylene oxide (3 mols) adduct (Croda's trade name, Crodamol STS), an ester of 2-ethylhexyl acid with benzyl alcohol propylene oxide (3 mols) adduct (Croda's trade name, Crodamol SFX), etc.

(Dialkyl Carbonate Compound Represented by General Formula (5))

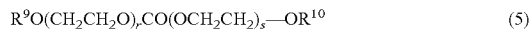

$$R^9O(CH_2CH_2O)_rCO(OCH_2CH_2)_s-OR^{10} \qquad (5)$$

(In the formula, $R^9$ and $R^{10}$ each represent a linear or branched alkyl and/or alkenyl group each having from 6 to 22 carbon atoms; r and s each indicate 0 or a number of from 1 to 50).

$R^9$ and $R^{10}$ in the compound represented by the general formula (5) each are preferably an alkyl group having from 6 to 18 carbon atoms, more preferably an alkyl group having from 8 to 12 carbon atoms, from the viewpoint of preventing the hair treated with the hair cosmetic of the present invention and dried from having an oily feeling and of improving finger combability and manageability of the hair.

From the same viewpoint as above, r and s each are preferably 0 or a number of from 1 to 5, more preferably 0.

Preferred examples of the dialkyl carbonate compound represented by the general formula (5) include dioctyl carbonate (Cognis' trade name, CETIOL CC), etc.

(Dialkyl Ether Compound Represented by General Formula (6))

$$R^{11}-O-R^{12} \qquad (6)$$

(In the formula, $R^{11}$ and $R^{12}$ each represent a linear or branched alkyl and/or alkenyl group each having from 6 to 22 carbon atoms).

$R^{11}$ and $R^{12}$ in the dialkyl ether compound represented by the general formula (6) each are preferably an alkyl group having from 6 to 18 carbon atoms, more preferably an alkyl group having from 8 to 12 carbon atoms, from the viewpoint of preventing the hair treated with the hair cosmetic of the present invention and dried from having an oily feeling and of improving finger combability and manageability of the hair.

Preferred examples of the dialkyl ether compound represented by the general formula (6) include dioctyl ether (Cognis' CETIOL OE), etc.

One alone or two or more compounds represented by the general formulae (4) to (6) may be used here either singly or as combined.

Of the oil (B) for use in the present invention, the amount of dissolution in 100 g of water at 20° C. is from 0 to 1 g, but is preferably from 0 to 0.5 g, more preferably from 0 to 0.1 g from the viewpoint of the manageability of the hair treated with the hair cosmetic of the present invention and dried.

The content of the oil (B) in the hair cosmetic of the present invention is preferably at least 0.01% by mass, more preferably at least 0.03% by mass, even more preferably at least 0.05% by mass, further more preferably at least 0.1% by mass from the viewpoint that the hair cosmetic of the present invention can impart good finger combability and manageability to the hair treated therewith and dried. On the other hand, from the viewpoint of preventing the hair treated with the hair cosmetic of the present invention and dried from having an oily feeling, the content of the oil is preferably at most 30% by mass, more preferably at most 20% by mass, even more preferably at most 15% by mass, further more preferably at most 10% by mass. Summing up these viewpoints, the content is preferably from 0.01 to 30% by mass, more preferably from 0.03 to 20% by mass, even more preferably from 0.05 to 15% by mass, further more preferably from 0.1 to 10% by mass.

In case where the hair cosmetic is shampoo, the content of the oil (B) is more preferably from 0.1 to 10% by mass, even more preferably from 0.5 to 8% by mass, further preferably from 3 to 6% by mass, from the same viewpoint as above.

The hair cosmetic of the present invention can be emulsified even though a large amount of oil is incorporated therein. In case where a large amount of oil is incorporated, the content of the oil (B) in the hair cosmetic is preferably from 5 to 50% by mass, more preferably from 10 to 40% by mass, even more preferably from 15 to 30% by mass.

In case where the hair cosmetic contains, as the oil (B), a combination of the above-mentioned oil of which the amount of dissolution in 100 g of water at 20° C. is from 0 to 1 g (hereinafter this may be referred to as "oil (B1)") and at least one compound selected from an ester compound represented by the general formula (4), a dialkyl carbonate compound represented by the general formula (5) and a dialkyl ether compound represented by the general formula (6) (hereinafter this may be referred to as "oil (B2)"), the content of the oil (B1) is preferably at least 0.1% by mass, more preferably at least 0.3% by mass, even more preferably at least 0.5% by mass, from the viewpoint of improving the finger combability and the manageability of the hair treated with the hair cosmetic of the present invention and dried. Also from the viewpoint of preventing the hair treated with the hair cosmetic of the present invention and dried from having an oily feeling and of improving the finger combability of the hair, the content of the oil (B1) in the hair cosmetic is preferably at most 10% by mass, more preferably at most 8% by mass, even more preferably at most 5% by mass. Summing up these viewpoints, the content of the oil (B1) in the hair cosmetic is preferably from 0.1 to 10% by mass, more preferably from 0.3 to 8% by mass, even more preferably from 0.5 to 5% by mass.

Further, the hair cosmetic of the present invention preferably contains, as the other oil component, a silicone oil in an amount of from 0.5 to 5% by mass.

In case where the hair cosmetic of the present invention is used in shampoo, the total content of the oil (B1) and the oil (B2) is preferably at least 0.2% by mass, more preferably at least 0.5% by mass, even more preferably at least 1% by mass, from the viewpoint of improving the finger combability and the manageability of the hair treated with the hair cosmetic of the present invention and dried. Also from the viewpoint of preventing the hair treated with the hair cosmetic of the present invention and dried from having an oily feeling and of improving the finger combability of the hair, the total content is preferably at most 10% by mass in the hair cosmetic, more preferably at most 8% by mass, even more preferably at most 6% by mass. Summing up these viewpoints, the total content of the oil (B1) and the oil (B2) in the hair cosmetic is preferably from 0.2 to 10% by mass, more preferably from 0.5 to 8% by mass, even more preferably from 1 to 6% by mass.

In case where the oil (B2) is used as the oil (B) in shampoo or the like, the ratio by mass of the oil (B2) to C—HPC (A) [oil (B2)/C—HPC (A)] is preferably form 0.05 to 150, more preferably from 0.1 to 50, even more preferably from 0.5 to 25, furthermore preferably from 1.5 to 12, from the viewpoint of preventing the hair treated with the hair cosmetic of the present invention and dried from having an oily feeling and of improving the finger combability of the hair.

In case where the hair cosmetic is a conditioner, the content of the component (B) therein is preferably from 1 to 15% by mass, more preferably from 3 to 12% by mass from the same viewpoint as above. In case where the hair cosmetic is an out-bath treatment, the content is more preferably from 0.1 to 5% by mass, even more preferably from 0.3 to 1% by mass from the same viewpoint as above.

In case where the oil (B2) is used as the oil (B) in conditioner, hair rinse, treatment or the like, the content thereof in the hair cosmetic is preferably at least 0.1% by mass, more preferably at least 0.5% by mass, even more preferably at least 0.8% by mass, from the viewpoint of preventing the hair treated with the hair cosmetic of the present invention and dried from having an oily feeling and of improving the finger combability and the manageability of the hair. Also from the viewpoint of preventing the hair treated with the hair cosmetic of the present invention and dried from having an oily feeling, the content in the hair cosmetic is preferably at most 10% by mass, more preferably at most 8% by mass, even more preferably at most 2% by mass. Summing up these viewpoints, the content of the oil (B2) in the hair cosmetic is preferably from 0.1 to 10% by mass, more preferably from 0.5 to 8% by mass, even more preferably from 0.8 to 2% by mass.

In case where the oil (B2) is combined with the oil (B1) for use herein, the content of the oil (B1) is preferably at least 1% by mass, more preferably at least 2% by mass, even more preferably at least 3% by mass, from the viewpoint of improving the finger combability and the manageability of the hair treated with the hair cosmetic of the present invention and dried. Also from the viewpoint of preventing the hair treated with the hair cosmetic of the present invention and dried from having an oily feeling and of improving the finger combability of the hair, the content in the hair cosmetic is preferably at most 10% by mass, more preferably at most 8% by mass, even more preferably at most 5% by mass. Summing up these viewpoints, the content of the other oil in the hair cosmetic is preferably from 1 to 10% by mass, more preferably from 2 to 8% by mass, even more preferably from 3 to 5% by mass.

Further, the hair cosmetic of the present invention preferably contains, as the other oil, a higher alcohol in an amount of from 3 to 5% by mass.

In case where the hair cosmetic of the present invention is used in conditioner, hair rinse, treatment or the like, the total content of the oil (B1) and the oil (B2) as the oil (B) is preferably at least 1% by mass in the hair cosmetic, more preferably at least 2% by mass, even more preferably at least 4% by mass, from the viewpoint of improving the finger combability and the manageability of the hair treated with the hair cosmetic of the present invention and dried. Also from the viewpoint of preventing the hair treated with the hair cosmetic of the present invention and dried from having an oily feeling, the total content in the hair cosmetic is preferably at most 20% by mass, more preferably at most 10% by mass, even more preferably at most 6% by mass. Summing up these viewpoints, the total content of the oil (B1) and the oil (B2) in the hair cosmetic is preferably from 1 to 20% by mass, more preferably from 2 to 10% by mass, even more preferably from 4 to 6% by mass.

In case where the oil (B2) is used as the oil (B) in conditioner, hair rinse, treatment or the like, the ratio by mass of the oil (B2) to C—HPC (A) [oil (B2)/C—HPC (A)] is preferably from 0.1 to 150, more preferably from 0.5 to 50, even more preferably from 1.5 to 25, further more preferably from 3 to 12, from the viewpoint of preventing the hair treated with the hair cosmetic of the present invention and dried from having an oily feeling and of improving the finger combability and the manageability of the hair.

<Surfactant (C)>

The hair cosmetic of the present invention contains a surfactant (C).

The surfactant (C) for use in the present invention may be any and every surfactant generally used in medicines, quasi drugs, cosmetics, toiletries, sundries and the like, except the compounds represented by the above-mentioned general formula (14) and salts of carboxylic acids with a hydrocarbon group having at least 17 carbon atoms and optionally substituted with a hydroxyl group. Concretely, there are mentioned anionic surfactants (C'), nonionic surfactants, ampholytic surfactants and cationic surfactants. From the viewpoint of the manageability of the hair treated with the hair cosmetic and dried, preferred is use of ionic surfactants such as anionic surfactants (C'), ampholytic surfactants and cationic surfactants.

In case where the hair cosmetic of the present invention is used as shampoo or the like, preferred is use of an anionic surfactant (C') and/or an ampholytic surfactant as the surfactant, from the viewpoint of the washing performance, the foamability and the foam quality of the hair cosmetic.

In case where the hair cosmetic of the present invention is used as hair treatment, hair rinse, hair conditioner, hair cream or the like, preferred is use of a cationic surfactant and/or a nonionic surfactant from the viewpoint of the feeling, such as the finger combability of the hair treated with the hair cosmetic of the present invention and dried, and more preferred is use of a cationic surfactant.

As the anionic surfactant (C'), preferred are sulfate ester salts, sulfonate salts, carboxylate salts, phosphate ester salts and amino acid salts.

Concretely, there are mentioned sulfate ester salts such as alkyl sulfate salts, alkenyl sulfate salts, polyoxyalkylene alkyl ether sulfate salts, polyoxyalkylene alkenyl ether sulfate salts, polyoxyalkylene alkylphenyl ether sulfate salts, etc.; sulfonate salts such as alkyl sulfosuccinates salts, polyoxyalkylene alkyl sulfosuccinate salts, alkanesulfonate salts, acylisethionates, acylmethyltaurates, etc.; carboxylic acid salts such as higher fatty acid salts having from 8 to 16 carbon atoms, polyoxyalkylene alkylether acetate salts, etc.; phosphate ester salts such as alkyl phosphate salts, polyoxyalkylene alkylether phosphate salts, etc.; amino acid salts such as acylglutamic acid salts, alanine derivatives, glycine derivatives, arginine derivatives, etc.

From the viewpoint of the washing performance, the foamability and the foam quality of the hair cosmetic of the present invention and of the finger combability and the manageability of the hair treated with the hair cosmetic and dried, the anionic surfactant (C') preferably has, as the hydrophobic moiety therein, an alkyl or alkenyl group having from 8 to 20 carbon atoms, more preferably an alkyl or alkenyl group having from 10 to 16 carbon atoms.

Of the above, preferred are alkyl sulfate salts such as sodium lauryl sulfate, etc.; polyoxyethylene alkylether sulfate salts such as sodium polyoxyethylene lauryl ether sulfate, etc.; higher fatty acid salts such as potassium laurate, etc.; polyoxyethylene alkyl ether acetate salts such as sodium polyoxyethylene lauryl ether acetate, etc.; alkyl sulfosuccinate salts such as sodium polyoxyethylene lauryl ether sulfosuccinate, etc.; acylglutamic acid salts such as sodium N-acryl-L-glutamate, etc.; acylsarcosine salts, acylglycine salts, acylisethionic acid salts, acylmethyl taurate and alkylphosphate salts. More preferred are sodium lauryl sulfate, ammonium polyoxyethylene (1) lauryl ether sulfate (ammonium laureth-1 sulfate), sodium polyoxyethylene (2) lauryl ether sulfate (sodium laureth-2 sulfate), potassium laurate, sodium polyoxyethylene (4.5) lauryl ether acetate (sodium laureth-4.5 acetate), sodium polyoxyethylene lauryl ether (2) sulfosuccinates (sodium laureth-2 sulfosuccinate), and sodium cocoyl glutamate.

The nonionic surfactant includes polyethylene glycol-type surfactants such as polyoxyethylene sorbitan fatty acid esters, polyoxyethylene sorbitol fatty acid esters, polyoxyethylene glycerin fatty acid esters, polyoxyethylene fatty acid esters, polyoxyethylene alkyl ethers, polyoxyethylene alkyl phenyl ethers, polyoxyalkylene (hardened) castor oil, etc.; polyalcohol-type surfactants such as sucrose fatty acid esters, polyglycerin alkyl ethers, polyglycerin fatty acid esters, alkyl glycosides, etc.; and fatty acid alkanolamides.

From the viewpoint of the washing performance, the amount of foams in washing, and the foam quality of the hair cosmetic of the present invention and of the finger combability and the manageability of the hair treated with the hair cosmetic and dried, the nonionic surfactant preferably has, as the hydrophobic moiety therein, an alkyl or alkenyl group having from 8 to 20 carbon atoms.

Of the above, preferred are alkyl glucosides having from 8 to 18 carbon atoms, more preferably from 8 to 12 carbon atoms such as decyl glucoside, etc.; polyoxyethylene alkyl ethers such as polyoxyethylene lauryl ether, etc.; and fatty acid monoalkanolamides such as cocoyl fatty acid monoethanolamide, etc. More preferred are decyl glucoside, polyoxyethylene (3) lauryl ether (laureth-3), polyoxyethylene (16) myristyl ether (ceteareth-16), cocoyl fatty acid monoethanolamide, and cocoyl fatty acid N-methylmonoethanolamide.

The ampholytic surfactant includes betaine-type surfactants such as imidazoline betaines, alkyldimethylaminoacetate betaines, fatty acid amide propylbetaines, sulfobetaines, etc.; and amine oxide-type surfactants such as alkyldimethylamine oxides, etc. Of those, preferred are imidazoline betaines, sulfobetaines, fatty acid amide propylbetaines, etc., from the viewpoint of the washing performance, the amount of foams in washing, and the foam quality of the hair cosmetic of the present invention and of the improved finger combability and manageability of the hair treated with the hair cosmetic and dried. Concretely preferred are cocoyl fatty acid amide propylbetaines, laurylcarbomethoxymethylhydroxyimidazolium betaine and laurylhydroxysulfobetaine.

The cationic surfactant includes salts of mineral acids or organic acids with tertiary amines represented by the following general formula (15), and quaternary ammonium-type surfactants represented by the following general formula (16).

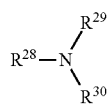

(15)

(In the formula, $R^{28}$ represents a linear or branched alkyl or alkenyl group having from 6 to 28 carbon atoms and optionally interrupted by an amide group, an ester group or an ether group; $R^{29}$ represents a linear or branched alkyl, alkenyl or alkanol group having from 1 to 28 carbon atoms and optionally interrupted by an amide group, an ester group or an ether group; $R^{30}$ represents a linear or branched alkyl or alkanol group having from 1 to 3 carbon atoms.)

In the general formula (15), the carbon number of $R^{28}$ is preferably from 12 to 28, more preferably from 14 to 25, even more preferably from 16 to 25 from the viewpoint that the hair treated with the hair cosmetic of the present invention and dried can have improved finger combability and manageability. From the same viewpoint, the carbon number of $R^{29}$ is preferably from 12 to 28, more preferably from 14 to 25, even more preferably from 16 to 25; and preferred is a methyl group, an ethyl group, or a hydroxyethyl group. Also from the same viewpoint, $R^{30}$ is preferably a methyl group, an ethyl group, or a hydroxyethyl group.

The mineral acid or the organic acid to form a salt with the tertiary amine represented by the general formula (15) is not specifically defined, but from the viewpoint of the dispersion stability of the surfactant, preferred are hydrogen halides, sulfuric acid, acetic acid, citric acid, lactic acid, glutamic acid, and alkylsulfuric acids having from 1 to 3 carbon atoms. From the viewpoint of chemical stability, the hydrogen halide is preferably hydrogen chloride.

(16)

(In the formula, $R^{31}$ represents a linear or branched alkyl or alkenyl group having from 6 to 28 carbon atoms and optionally interrupted by an amide group, an ester group or an ether group; $R^{32}$ represents a linear or branched alkyl, alkenyl or alkanol group having from 1 to 28 carbon atoms and optionally interrupted by an amide group, an ester group or an ether group; $R^{33}$ and $R^{34}$ each represent a linear or branched alkyl group having from 1 to 3 carbon atoms; $Z^-$ represents an anion group which is a counter ion to the ammonium salt).

In the general formula (16), preferred embodiments of $R^{31}$ are the same as the preferred embodiments of $R^{28}$ in the general formula (15) from the viewpoint of improving the finger combability and the manageability of the hair treated with hair cosmetic of the present invention and dried. From the same viewpoint, preferred embodiments of $R^{32}$ are the same as the preferred embodiments of $R^{29}$ in the general formula (15). Also from the same viewpoint, $R^{33}$ and $R^{34}$ each are preferably a methyl group or an ethyl group.

Not specifically defined, $Z^-$ may be any anionic group. Specific examples of the group include an alkylsulfate ion, a sulfate ion, a phosphate ion, an alkylcarboxylate ion, a halide ion, etc. Of those, preferred is a halide ion from the viewpoint of easiness in production and availability. The halide ion includes a fluoride ion, a chloride ion, a bromide ion and an iodide ion. From the viewpoint of chemical stability, preferred is a chloride ion or a bromide ion, and more preferred is a chloride ion.

Salts of mineral acids or organic acids with the tertiary amines represented by the general formula (15), and the quaternary ammonium salt-type surfactants represented by the general formula (16) include mono-long-chain alkyltrimethylammonium chlorides, di-long-chain alkyldimethylammonium chloride and long-chain tertiary amine salts. Concretely, there are mentioned mono-long-chain alkyltrimethylammonium chlorides such as stearyltrimethylammonium chloride, behenyltrimethylammonium chloride, cetyltrimethylammonium chloride, stearoxypropyltrimethylammonium chloride, etc.; di-long-chain alkyldimethylammonium chloride such as distearyldimethylammonium chloride, diisostearyldimethylammonium chloride, etc.; glutamates, hydrochlorides, citrates or lactates of mono-long chain dimethylamines or mono-long chain dimethylamines such as stearyldimethylamine, behenyldimethylamine, octadecyloxypropyldimethylamine, stearamidoethyldimethylamine, stearamidopropyldimethylamine, behenamidopropyldimethylamine, etc. From the viewpoint of improving the finger combability and the manageability of the hair treated with the hair cosmetic of the present invention and dried, preferred are behenyltrimethylammonium chloride, cetyltrimethylammonium chloride, stearoxypropyltrimethylammonium chloride, stearyldimethylamine, stearamidopropyldimethylamine, behenamidopropyldimethylamine.

The content of the surfactant (C) for use in the present invention is preferably at most 50% by mass in the hair cosmetic, more preferably at most 40% by mass, even more preferably at most 30%, further more preferably at most 25%, from the viewpoint of preventing the hair treated with the hair cosmetic of the present invention and dried from having an oily feeling and of improving the finger combability and the manageability of the hair. From the viewpoint of preventing the hair treated with the hair cosmetic and dried from having an oily feeling, the content is preferably at least 0.01% by mass, more preferably at least 0.05% by mass, even more preferably at least 0.08% by mass, further more preferably at least 0.1% by mass. Summing up the viewpoints, the content is preferably from 0.01 to 50% by mass, more preferably from 0.05 to 40% by mass, even more preferably from 0.08 to 30% by mass, further more preferably from 0.1 to 25% by mass.

In case where the hair cosmetic is shampoo, the content of the surfactant (C) is, from the same viewpoint as above, preferably from 3 to 22% by mass, more preferably from 8 to 20% by mass.

In case where the hair cosmetic is conditioner, the content of the surfactant (C) is, from the same viewpoint as above, preferably from 0.3 to 10% by mass, more preferably from 0.5 to 5% by mass, even more preferably from 0.7 to 3% by mass.

In case where the hair cosmetic is out-bath treatment, the content of the surfactant (C) is, from the same viewpoint as above, preferably from 0.1 to 5% by mass, more preferably from 0.1 to 1% by mass.

In the hair cosmetic of the present invention, the proportion by mass of C—HPC (A), the oil (B) and the surfactant (C) is as follows, from the viewpoint of preventing the hair treated with the hair cosmetic and dried from having an oily feeling and of improving the manageability of the hair.

The ratio by mass of the oil (B) to C—HPC (A) [oil (B)/C—HPC (A)] is preferably from 0.1 to 5000.

In case where the hair cosmetic is shampoo, the ratio by mass of [oil (B)/C—HPC (A)] is preferably from 0.1 to 200, more preferably from 0.5 to 20, even more preferably from 1 to 15, from the viewpoint of preventing the hair treated with the hair cosmetic of the present invention and dried from having an oily feeling and of improving the finger combability and the manageability of the hair.

In case where the hair cosmetic is conditioner, the ratio by mass of [oil (B)/C—HPC (A)] is, from the same viewpoint, preferably from 1 to 4000, more preferably from 3 to 500, even more preferably from 5 to 100, further more preferably from 6 to 50.

In case where the hair cosmetic is out-bath treatment, the ratio by mass of [oil (B)/C—HPC (A)] is, from the same viewpoint, preferably from 1 to 100, more preferably from 5 to 50, even more preferably from 7 to 20.

The ratio by mass of the surfactant (C) to C—HPC [surfactant (C)/C—HPC (A)] is preferably from 0.1 to 2000.

In case where the hair cosmetic is shampoo, the ratio by mass of [surfactant (C)/C—HPC (A)] is preferably from 1 to 1500, more preferably from 10 to 150, even more preferably from 20 to 150 from the viewpoint of preventing the hair treated with the hair cosmetic of the present invention and dried from having an oily feeling and of improving the finger combability and the manageability of the hair.

In case where the hair cosmetic is conditioner, the ratio by mass of [surfactant (C)/C—HPC (A)] is, from the same viewpoint as above, preferably from 0.1 to 2000, more preferably from 1 to 200, even more preferably from 2 to 20.

In case where the hair cosmetic is out-bath treatment, the ratio by mass of [surfactant (C)/C—HPC (A)] is, from the same viewpoint as above, preferably from 0.1 to 100, more preferably from 0.5 to 50, even more preferably from 2 to 20.

<Other Components>

The hair cosmetic of the present invention may contain any other components generally used as cosmetic materials than the above-mentioned C—HPC (A), oil (B) and surfactant (C). The optional components include feeling improver, thickener, surfactant, oil, fragrance, UV absorbent, visible light absorbent, chelating agent, antioxidant, colorant, preservative, pH regulator, viscosity regulator, pearly gloss agent, moisturizer, etc.

[Method for Producing Hair Cosmetic]

The method for producing the hair cosmetic of the present invention is a method for producing a hair cosmetic containing a cationized hydroxypropyl cellulose (A), an oil (B) of which the amount of dissolution in 100 g of water at 20° C. is from 0 to 1 g, and a surfactant (C), wherein the cationized hydroxypropyl cellulose (A) has an anhydroglucose-derived main chain represented by the above-mentioned general formula (1), and has a degree of substitution with cationized ethyleneoxy group of from 0.01 to 2.9 and a degree of substitution with propyleneoxy group of from 0.1 to 4.0; and the method includes the above-mentioned steps (a-1) to (a-3), the above-mentioned steps (a-4) and (a-5), the above-mentioned steps (b-1) to (b-4) or the above-mentioned steps (c-1) to (c-4).

From the viewpoint of improving the finger combability and the manageability of the hair treated with the hair cosmetic and dried, the production method of the present invention preferably includes the above-mentioned steps (a-1) to (a-3), the above-mentioned steps (b-1) to (b-4) or the above-mentioned steps (c-1) to (c-4); and from the viewpoint of preventing the molecular weight of C—HPC from lowering, the production method includes more preferably the above-mentioned steps (b-1) to (b-4) or the above-mentioned steps (c-1) to (c-4).

From the viewpoint of preventing the hair treated with the hair cosmetic of the present invention and dried from having an oily feeling and of improving the finger combability and the manageability of the hair and further improving the moist feeling of the dried hair, the hair cosmetic of the present invention is preferably produced according to a process of the following steps (I) to (III). Consequently, the present invention also provides a method for producing the hair cosmetic that contains the following steps (I) to (III).

Step (I): a step of mixing a cationized hydroxypropyl cellulose (A) and an anionic surfactant (C') to prepare a mixture, Step (II): a step of mixing the mixture obtained in the step (I) and an oil (B) to prepare an emulsion, Step (III): a step of mixing the emulsion obtained in the step (II) with a surfactant and water to give a hair cosmetic.

(Step (I))

The step (I) is a step of mixing a cationized hydroxypropyl cellulose (A) and an anionic surfactant (C'). According to the step (I), it is considered that a complex of the cationized hydroxypropyl cellulose (A) and the anionic surfactant (C') can be formed efficiently.

As the anionic surfactant (C') for use in the step (I), preferred is the anionic surfactant (C') exemplified for the above-mentioned surfactant (C), from the viewpoint of efficiently forming the complex of the cationized hydroxypropyl cellulose (A) and the anionic surfactant (C'), and from the viewpoint of preventing the oily feeling after drying and improving the finger combability, the manageability and the moist feeling. More preferred are sulfate ester salts, sulfonate salts, carboxylate salts, phosphate ester salts and amino acid salts; and even more preferred are sodium lauryl sulfate, ammonium polyoxyethylene (1) lauryl ether sulfate (ammonium laureth-1 sulfate), sodium polyoxyethylene (2) lauryl ether sulfate (sodium laureth-2 sulfate), potassium laurate, sodium polyoxyethylene (4.5) lauryl ether acetate (sodium laureth-4.5 acetate), sodium polyoxyethylene lauryl ether (2) sulfosuccinates (sodium laureth-2 sulfosuccinate), and sodium cocoyl glutamate.

In the step (I), preferably, the cationized hydroxypropyl cellulose (A) is, after formed into an aqueous solution thereof, mixed with the anionic surfactant (C'). From the viewpoint of efficiently forming the complex of the cationized hydroxypropyl cellulose (A) and the anionic surfactant (C'), preferably, the concentration of the aqueous cationized hydroxypropyl cellulose solution is from 1.0 to 10.0% by mass.

From the same viewpoint as above, the ratio by mass of the anionic surfactant (C') to C—HPC (A) [anionic surfactant (C')/C—HPC (A)] in the step (I) is preferably from 0.01 to 1.0, more preferably from 0.02 to 0.7, even more preferably from 0.03 to 0.5.

The mixing time in the step (I) is preferably from 1 to 60 minutes.

(Step (II))

The step (II) is a step of mixing the mixture obtained in the step (I) and an oil (B) to obtain an emulsion. It is considered that an emulsion can be formed efficiently in the step (II).

The content of the oil (B) in the emulsion is preferably from 10 to 80% by mass, more preferably from 20 to 70% by mass, even more preferably from 30 to 60% by mass, from the viewpoint of preventing the oily feeling after drying and improving the finger combability, the manageability and the moist feeling.

Also from the viewpoint of preventing the oily feeling after drying and improving the finger combability, the manageability and the moist feeling, the mean particle size of the oil drops to be formed in the emulsion is preferably from 0.1 to 35 μm, more preferably from 0.5 to 30 μm, even more preferably from 1 to 20 μm. Here the mean particle size of the oil drops is the value measured according to the method described in the section of Examples.

The mixture and the oil (B) may be mixed little by little, but may also be mixed all at a time. The stirring speed in mixing is preferably from 50 to 3000 rpm, more preferably from 100 to 1000 rpm, even more preferably from 150 to 600 rpm, further more preferably from 200 to 400 rpm, from the viewpoint of preparing a stable emulsion. The peripheral speed in mixing is, also from the same viewpoint, preferably from 0.1 to 8 m/sec, more preferably from 0.3 to 3 m/sec, even more preferably from 0.4 to 2 m/sec.

The mixing time in the step (II) is preferably from 1 to 60 minutes.

(Step (III))

The step (III) is a step of mixing the emulsion obtained in the step (II) with a surfactant (C) and water to give a hair cosmetic. It is considered that, according to the step (III), there can be produced a hair cosmetic having the ability to efficiently leave the oil (B) on the hair and capable of giving moist feeling to the hair after drying.

In the step (III), the above-mentioned emulsion is mixed with a surfactant (C) and water. Further, the above-mentioned conventional known additives may be added thereto. The sequence of mixing the emulsion with the surfactant (C), water and the additives is not specifically defined.

The production method containing the above-mentioned steps (I) to (III) efficiently produces the hair cosmetic that prevents an oily feeling after drying and improves the finger combability, the manageability and the moist feeling.

Relative to the above-mentioned embodiments, the present invention discloses the following hair cosmetic and the following production method for the composition.

[1] A hair cosmetic containing a cationized hydroxypropyl cellulose (A), an oil (B) of which the amount of dissolution in 100 g of water at 20° C. is from 0 to 1 g, preferably from 0 to 0.5 g, more preferably from 0 to 0.1 g, and a surfactant (C), wherein the cationized hydroxypropyl cellulose (A) has an anhydroglucose-derived main chain represented by the following general formula (1), and has a degree of substitution with cationized ethyleneoxy group of from 0.01 to 2.9, preferably from 0.1 to 2.5, more preferably from 0.2 to 2.0, even more preferably from 0.3 to 1.5, further more preferably 0.8 to 1.2, and a degree of substitution with propyleneoxy group of from 0.1 to 4.0, preferably from 0.2 to 3.0, more preferably from 0.3 to 2.8, even more preferably from 0.6 to 2.5, further more preferably from 1.0 to 2.0.

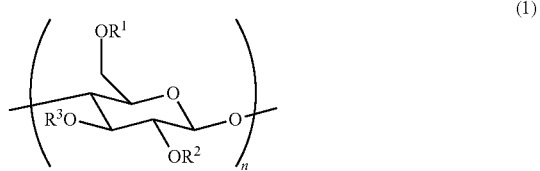

(In the formula, $R^1$, $R^2$ and $R^3$ each independently represent a substituent having a cationized ethyleneoxy group and a propyleneoxy group represented by the following general formula (2); n indicates a mean degree of polymerization of anhydroglucose and is a number of from 50 to 5000, preferably from 100 to 3000, more preferably from 200 to 2000, even more preferably from 300 to 1500).

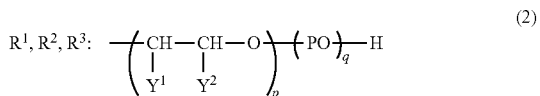

(In the formula, one of $Y^1$ and $Y^2$ is a hydrogen atom and the other is a cationic group represented by the following general formula (3); PO represents a propyleneoxy group. p indicates the number of cationized ethyleneoxy groups ((—CH($Y^1$)—CH($Y^2$)—O—) in the general formula (2) and q indicates the number of propyleneoxy groups (—PO—) therein, each representing 0 or a positive integer, preferably an integer of from 0 to 2, more preferably 0 or 1. In case where both of p and q are not 0, the addition sequence of the cationized ethyleneoxy group and the propyleneoxy group is not defined, and in case where p and/or q are/is 2 or more, a binding form may be any of like a block co-polymer or like a random co-polymer).

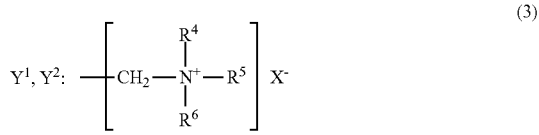

(3)

(In the formula, $R^4$, $R^5$ and $R^6$ each independently represent a linear or branched alkyl group having from 1 to 3 carbon atoms, preferably a methyl group or an ethyl group, more preferably a methyl group; and $X^-$ represents an anionic group, preferably a halide ion.)

[2] The hair cosmetic according to the above [1], wherein the content of the cationized hydroxypropyl cellulose (A) is from 0.001 to 10% by mass, preferably from 0.005 to 5% by mass, more preferably from 0.01 to 2% by mass, even more preferably from 0.05 to 1% by mass, further more preferably from 0.07 to 0.7% by mass.

[3] The hair cosmetic according to the above [1] or [2], wherein the mean degree of polymerization, n, of the anhydroglucose in the general formula (1) is from 300 to 1500.

[4] The hair cosmetic according to any of the above [1] to [3], wherein the ratio by mass of the oil (B) to the cationized hydroxypropyl cellulose (C—HPC) (A) [oil (B)/C—HPC (A)] is from 0.1 to 5000.

[5] The hair cosmetic according to any of the above [1] to [4], wherein the ratio by mass of the surfactant (C) to C—HPC [surfactant (C)/C—HPC (A)] is from 0.1 to 2000.

[6] The hair cosmetic according to any of the above [1] to [5], wherein the oil (B) is at least one compound selected from ester compounds represented by the following general formula (4), dialkyl carbonate compounds represented by the following general formula (5), and dialkyl ether compounds represented by the following general formula (6):

$R^7O\text{-}(AO)_m\text{—}COR^8$ (4)

(In the formula, $R^7$ represents a hydrocarbon group having from 6 to 20 carbon atoms and containing at least one substituted or unsubstituted aromatic ring, preferably an aromatic hydrocarbon group having from 6 to 12 carbon atoms, more preferably an aromatic hydrocarbon group having from 6 to 10 carbon atoms, even more preferably a benzyl group; $R^8$ represents a linear or branched alkyl or alkenyl group having from 1 to 25 carbon atoms, preferably an alkyl group having from 7 to 21 carbon atoms, more preferably an alkyl group having from 11 to 15 carbon atoms; AO represents an alkyleneoxy group having from 2 to 4 carbon atoms; m indicates a number of from 1 to 50, preferably a number of from 1 to 10, more preferably a number of from 1 to 5. In case where m is 2 or more, m's AO groups may be the same or different).

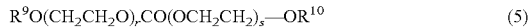

$R^9O(CH_2CH_2O)_rCO(OCH_2CH_2)_s\text{—}OR^{10}$ (5)

(In the formula, $R^9$ and $R^{10}$ each represent a linear or branched alkyl and/or alkenyl group each having from 6 to 22 carbon atoms, preferably an alkyl group having from 6 to 18 carbon atoms, more preferably an alkyl group having from 8 to 12 carbon atoms; r and s each indicate 0 or a number of from 1 to 50, preferably 0 or a number of from 1 to 5, more preferably 0).

$R^{11}\text{—}O\text{—}R^{12}$ (6)

(In the formula, $R^{11}$ and $R^{12}$ each represent a linear or branched alkyl and/or alkenyl group each having from 6 to 22 carbon atoms, preferably an alkyl group having from 6 to 18 carbon atoms, more preferably an alkyl group having from 8 to 12 carbon atoms).

[7] The hair cosmetic according to any of the above [1] to [6], wherein the cationized hydroxypropyl cellulose (A) is obtained by the following steps (a-1) to (a-3):

Step (a-1): a step of adding a cationizing agent to a cellulose-containing raw material and processing it with a grinder, Step (a-2): a step of adding a base to the grinder-processed product obtained in the step (a-1), and while processing it with a grinder, reacting the cellulose-containing raw material and the cationizing agent to give a cationized cellulose, Step (a-3): a step of reacting the cationized cellulose obtained in the step (a-2) with propylene oxide to give the cationized hydroxypropyl cellulose (A).

[8] The hair cosmetic according to any of the above [1] to [6], wherein the cationized hydroxypropyl cellulose (A) is obtained by the following steps (b-1) to (b-4):

Step (b-1): a step of processing a cellulose-containing raw material with a grinder to give a cellulose-containing raw material that contains a cellulose having a degree of crystallinity of from 10 to 50%, Step (b-2): a step of adding to the cellulose-containing raw material obtained in the step (b-1), a base in an amount of from 0.6 to 1.5 molar times per mol of the anhydroglucose unit that constitutes the cellulose in the cellulose-containing raw material, and water in an amount of from 20 to 100% by mass relative to the cellulose in the cellulose-containing raw material, thereby giving an alkali cellulose, Step (b-3): a step of reacting the alkali cellulose obtained in the step (b-2) with propylene oxide to give a hydroxypropyl cellulose, Step (b-4): a step of reacting the hydroxypropyl cellulose obtained in the step (b-3) with a cationizing agent to give the cationized hydroxypropyl cellulose (A).

[9] The hair cosmetic according to any of the above [1] to [6], wherein the cationized hydroxypropyl cellulose (A) is obtained by the following steps (c-1) to (c-4):

Step (c-1): a step of processing a mixture of a cellulose-containing raw material and a base in an amount of from 0.6 to 1.5 molar times per mol of the anhydroglucose unit that constitutes the cellulose in the cellulose-containing raw material, with a grinder under the condition where the water content in the cellulose-containing raw material is at most 10% by weight relative to the cellulose therein, thereby giving a ground cellulose/base mixture in which the mean particle size of the cellulose is from 10 to 150 μm, Step (c-2): a step of adding water to the ground cellulose/base mixture obtained in the step (c-1) to thereby control the water content in the ground cellulose/base mixture to be from 30 to 100% by mass relative to the cellulose in the cellulose-containing raw material used in the step (c-1), thereby giving an alkali cellulose, Step (c-3): a step of reacting the alkali cellulose obtained in the step (c-2) with propylene oxide to give a hydroxypropyl cellulose, Step (c-4): a step of reacting the hydroxypropyl cellulose obtained in the step (c-3) with a cationizing agent to give the cationized hydroxypropyl cellulose (A).

[10] A method for producing a hair cosmetic containing a cationized hydroxypropyl cellulose (A), an oil (B) of which the amount of dissolution in 100 g of water at 20° C. is from 0 to 1 g, and a surfactant (C), in which the cationized hydroxypropyl cellulose (A) has an anhydroglucose-derived main chain represented by the above-mentioned general formula (1), and has a degree of substitution with cationized ethyleneoxy group of from 0.01 to 2.9 and a degree of substitution with propyleneoxy group of from 0.1 to 4.0; the method including the steps (a-1) to (a-3) stated in the above [7], the steps (b-1) to (b-4) stated in the above [8], or the steps (c-1) to (c-4) stated in the above [9].

[11] A method for producing a hair cosmetic, containing the following steps (I) to (III):

Step (I): a step of mixing a cationized hydroxypropyl cellulose (A) and an anionic surfactant (C') to prepare a mixture, Step (II): a step of mixing the mixture obtained in the step (I) and an oil (B) to prepare an emulsion, Step (III): a step of mixing the emulsion obtained in the step (II) with a surfactant (C) and water to give a hair cosmetic.

[12] Use of the hair cosmetic stated in any of the above [1] to [6] as a hair cosmetic.

[13] Use according to the above [12], wherein the hair cosmetic is shampoo.

[14] Use according to the above [12], wherein the hair cosmetic is conditioner, hair rinse or treatment.

[15] Use according to the above [12], wherein the hair cosmetic is out-bath treatment.

EXAMPLES

Unless otherwise specifically indicated in the following Examples and Comparative Examples, "part" is "part by mass" and "%" is "% by mass". Measurement methods for the physical properties of the samples are as described below.

(1) Measurement of Water Content in Pulp and Powdery Cellulose

The water content in pulp or powdery cellulose was measured, using an IR moisture meter (Kett Electric Laboratory's "FD-610"). The measurement temperature was 120° C., and the point at which the weight change for 30 seconds reached at most 0.1% was referred to as the final point in the measurement.

(2) Calculation of Crystallinity of Pulp and Powdery Cellulose

Using Rigaku's "Rigaku RINT 2500VC X-RAY Diffractometer", the sample was analyzed under the condition mentioned below, and from the peak intensity on the diffraction spectrum, the degree of crystallinity of the sample was calculated according to the above-mentioned math formula (1).

X-ray source: Cu/Kα-radiation, bulb voltage: 40 kV, bulb current: 120 mA

Detection range: 2θ=5 to 45°.

Sample: prepared by compressing a pellet having an area of 320 mm$^2$ and a thickness of 1 mm.

X-ray scanning speed: 109 min.

In case where the degree of crystallinity thus measured was a negative value, all such samples were considered to have a crystallinity of 0%.

(3) Measurement of Mean Particle Size Powdery Cellulose and Cellulose in Ground Cellulose/Base Mixture The mean particle size of powdery cellulose was determined, using a laser diffraction/scattering particle sizer "LA-920" (by Horiba). The test sample was prepared by adding 0.1 g of a powdery cellulose to 5 mL of water and ultrasonicated for 1 minute to prepare a sample dispersion. The volume-based median diameter was measured at a temperature of 25° C., and was referred to as the mean particle size.

The mean particle size of the cellulose in a ground cellulose/base mixture was determined using the same apparatus. Ethanol was added to a ground cellulose/base mixture and the concentration of the resulting mixture was so controlled that the transmittance thereof could fall within a range of from 70 to 95%. The mixture was ultrasonicated for 1 minute, and NaOH was added thereto to prepare a sample dispersion.

(4) Calculation of Substitution Degree in C—HPC

C—HPC produced in Production Example was purified through a dialytic membrane (molecular weight cut off, 1000), and then the aqueous solution was freeze-dried to give a purified C—HPC. The chlorine content in the thus-obtained pure C—HPC was measured through elementary analysis. The number of the cationic groups contained in C—HPC and the number of the chloride ions that are counter ions were approximated to be the same number, and the amount of the cationized ethyleneoxy groups (—CH($Y^1$)—CH($Y^2$)O—) contained in the unit mass of C—HPC (a (mol/g)) was calculated according to the following math formula (2).

$$a(mol/g)=\text{chlorine content (\%) obtained through elementary analysis}/(35.5\times100) \quad (2)$$

The hydroxypropoxy group content (%) was determined according to the "Method for Analysis of Hydroxypropyl Cellulose" described in Japanese Pharmacopoeia, except that the object to be analyzed here was pure C—HPC but not hydroxypropyl cellulose. According to the math formula (3) mentioned below, the hydroxypropoxy group content [formula weight ($OC_3H_6OH$=75.09)] (b mol/g) was obtained.

$$b(mol/g)=\text{hydroxypropoxy group content (\%) obtained through gas chromatography}/(75.09\times100) \quad (3)$$

From the thus-obtained a and b and according to the following math formulae (4) and (5), the degree of substitution with cationized ethyleneoxy group (k) and the degree of substitution with propyleneoxy group (m) were calculated.

$$a=k/(162+k\times K+m\times 58) \quad (4)$$

$$b=m/(162+k\times K+m\times 58) \quad (5)$$

[In the formulae, k and K each indicate the degree of substitution with cationized ethyleneoxy group and the formula weight; and m indicates the degree of substitution with propyleneoxy group.]

(5) Measurement of Mean Degree of Polymerization (Copper Ammonia Method)

(5-1) Measurement of Viscosity-Average Degree of Polymerization of Pulp and Powdery Cellulose (i) Preparation of Solution for Measurement 0.5 g of cuprous chloride and 20 to 30 mL of aqueous 25% ammonia were put into a measuring flask (100 mL) and completely dissolved, and then 1.0 g of cupric hydroxide and aqueous 25% ammonia were added thereto to be an amount just before the gauge line. This was stirred for 30 to 40 minutes and completely dissolved. Subsequently, cellulose as accurately weighed was added thereto, and the above-mentioned aqueous ammonia was added thereto up to the gauge line. This was airtightly sealed up, and stirred with a magnetic stirrer for 12 hours for dissolution to thereby prepare a solution for measurement. The amount of the cellulose to be added was varied within a range of from 20 to 500 mg, and solutions for measurement each having a different concentration were prepared.

(ii) Measurement of Viscosity-Average Degree of Polymerization

The solution for measurement (copper ammonia solution) obtained in the above (i) was put into an Ubbelohde viscometer and statically left in a thermostat chamber (20±0.1° C.) for 1 hour, and thereafter the flowing-down speed of the liquid was measured. From the flowing-down time (t (sec)) of the copper ammonia solution having a different cellulose concentration (g/dL) and the flowing-down time ($t_0$ (sec)) of a cellulose-free aqueous copper ammonia solution, the reduced viscosity ($\eta_{sp}/c$) at each concentration of the sample was determined according to the following formula:

$$\eta_{sp}/c = \{(t-t_0)/t_0\}/c$$

(c: cellulose concentration (g/dL))

Further, the reduced viscosity was extrapolated into c=0 to determine the intrinsic viscosity [η] (dL/g), and according to the following formula, the viscosity-average degree of polymerization (DP) was obtained.

$$DP = 2000 \times [\eta]$$

(5-2) Measurement of Viscosity-Average Degree of Polymerization of C—HPC
(iii) Preparation of Solution for Measurement The solution for measurement was prepared in the same manner as that for the solution for measurement in the above (i), except that a pure C—HPC was used in place of the pure cellulose.

(iv) Measurement of Viscosity-Average Degree of Polymerization

The viscosity-average degree of polymerization was measured in the same manner as that for the solution for the viscosity-average degree of polymerization of the above (ii), except that a cellulose-equivalent concentration (g/dL) was used in place of the concentration of the measurement solution.

The cellulose-equivalent concentration ($c_{cell}$) means the mass (g) of the cellulose skeleton part contained in 1 dL of the measurement solution, and is defined by the following math formula (6).

$$c_{cell} = u \times 162/(162 + k \times K + m \times 58) \tag{6}$$

[In the formula, u indicates the mass (g) of C—HPC that had been accurately weighed in preparation of the measurement solution; and k, K and m have the same meanings as in the above-mentioned math formulae (4) and (5).]

(6) Measurement of 2% Viscosity

With stirring, C—HPC was added to water at 25° C. to prepare an aqueous 2 mass % C—HPC solution. This was put into a viscometer tube with careful attention thereto so that no bubble could come therein, and sealed up with a parafilm, and statically left in a water bath at 30° C. for about 1 hour. Next, a rotor (No. M1 to M4) and a rotation number (6 to 60 rpm) were selected in accordance with the viscosity of the sample, and using a B-type viscometer (Toki Sangyo's Model TVB-10), the value indicated by the viscometer when the rotor was rotated for 1 minute was read out, and the viscosity was thereby calculated.

Production Example I-1

Production of C—HPC (I-1)

(1) Chipping Step

A sheet-like wood pulp (Tembec's Biofloc HV+, having a mean degree of polymerization of 1770, a degree of crystallinity of 74% and a water content of 7.0%) was pelletized with a sheet pelletizer (Horai's "SGG-220")) into chips of from 3 to 5 mm square.

(2) Cationization Step (1)

23.4 g of an aqueous solution of glycidyltrimethylammonium chloride (by Sakamoto Chemical Industry, water content 20%, purity 90% or more) (hereinafter referred to as "GMAC") (the amount corresponds to 0.2 mols per mol of AGU of cellulose) was added to 100 g of the chip-like pulp obtained in the above (1), and mixed in a mortar, and then put into a batch-type vibrational mill (Chuo Kakohki's "MB-1": chamber total volume 3.5 L; 13 rods of SUS304 each having a diameter of 30 mm and a length of 218 mm and having a circular cross section; filling rate 57%). This was ground for 30 minutes (frequency 20 Hz, vibrational amplitude 8 mm, temperature 30 to 70° C.) thereby giving a powdery mixture of cellulose and GMAC.

20 g (corresponding to 0.2 mols per mol of AGU) of an aqueous 24.7% sodium hydroxide solution was added to the obtained powdery mixture, mixed in a mortar and put into the above-mentioned batch-type vibrational mill. Under the same condition as above, this was ground for 60 minutes to give 151 g of a cationized cellulose (i).

(3) Cationization Step (2)

128 g of the cationized cellulose (i) obtained in the above (2) was mixed with 31.3 g of GMAC (corresponding to 0.32 mols per mol of AGU) in a mortar, and then the resulting mixture was put into a 1-L kneader equipped with a reflux tube (Irie Shokai's PNV-1 Model), and with stirring at 50° C. in a nitrogen atmosphere at 50 rpm, this was ripened for 5 hours to give a cationized cellulose (ii).

(4) Hydroxypropylation Step

The kneader containing 152.6 g of the cationized cellulose (ii) obtained after ripening (unneutralized unpurified product) was heated up to 70° C., and with stirring, 72.5 g propylene oxide (corresponding to 2.5 mols per mol of AGU, Kanto Chemical's special grade reagent) was dropwise added thereto and reacted for 20 hours until the propylene oxide was consumed and the reflux flow stopped.

After the reaction, the reaction mixture was taken out of the kneader to give 210.6 g of a pale brown crude C—HPC powder. 10.0 g of the crude C—HPC powder was sampled and neutralized with acetic acid. For the purpose of determining the degree of substitution with propyleneoxy group and with cationized ethyleneoxy group, the neutralized product was purified through a dialytic membrane (molecular weight cut off, 1000), and then the aqueous solution was freeze-dried to give a pure C—HPC (I-1).

Through elementary analysis thereof, the chlorine content of the obtained pure C—HPC (I-1) was 3.4%. The hydroxypropoxy group content according to the above-mentioned "Method for Analysis of Hydroxypropyl Cellulose" was 43.3%. The degree of substitution with cationized ethyleneoxy group and the degree of substitution with propyleneoxy group were 0.30 and 1.8, respectively. The mean degree of polymerization of the pure C—HPC (I-1) was 739. The results are shown in Table 1.

Production Example I-2

Production of C—HPC (I-2)

This is the same as in Production Example I-1 except that the condition of the cationization step (1) was changed as in Table 1, that the cationization step (2) was omitted, and that the condition of the hydroxypropylation step was changed as in Table 1. The results of the obtained pure C—HPC (I-2) are shown in Table 1.

Production Example I-3

Production of C—HPC (I-3)

This is the same as in Production Example I-1 except that the condition of the cationization step (1), that of the cationization step (2) and that of the hydroxypropylation step were changed as in Table 1. The results of the obtained pure C—HPC (I-3) are shown in Table 1.

Production Example I-4

Production of C—HPC (I-4)

This is the same as in Production Example I-1 except that the condition of the cationization step (1) was changed as in Table 1, that the cationization step (2) was omitted, and that the condition of the hydroxypropylation step was changed as in Table 1. The results of the obtained pure C—HPC (I-4) are shown in Table 1.

Production Example I-5

Production of C—HPC (I-5)

This is the same as in Production Example I-1 except that the condition of the cationization step (1), that of the cationization step (2) and that of the hydroxypropylation step were changed as in Table 1. The results of the obtained pure C—HPC (I-5) are shown in Table 1.

TABLE 1

| | Starting Pulp | | | | Cationization Step (1) | | | | | | Cationization Step (2) | |
|---|---|---|---|---|---|---|---|---|---|---|---|---|
| | Degree of Crystallinity (%) | Mean Degree of Polymerization | Water Content (%) | Amount of Pulp Used (g) | Vibrational Mill | Amount of GMAC Added (g) | Grinding Time (min) | Amount of 24.7% NaOH Added (g) | Amount of 48% NaOH Added (g) | Grinding Time (min) | Amount of Cationized Cellulose (i) Used (g) | Amount of GMAC Added (g) |
| Production Example I-1 | 74 | 1770 | 7.0 | 100 | MB-1 | 23.4 | 30 | 20 | — | 60 | 128 | 31.3 |
| Production Example I-2 | 74 | 1770 | 7.0 | 100 | MB-1 | 60.8 | 12 | — | 14.8 | 120 | — | — |
| Production Example I-3 | 74 | 1770 | 7.0 | 100 | MB-1 | 23.4 | 12 | — | 6.2 | 60 | 175 | — |
| Production Example I-4 | 74 | 1770 | 7.0 | 100 | MB-1 | 109 | 12 | — | 47.9 | 120 | — | — |
| Production Example I-5 | 74 | 1770 | 7.0 | 86 | MB-1 | 20 | 12 | — | 8.8 | 60 | 110 | 132 |

| | Cationization Step (2) | | Hydroxypropylation Step | | | Physical Properties of C-HPC | | |
|---|---|---|---|---|---|---|---|---|
| | Ripening Temperature (°C.) | Ripening Time (hr) | Amount of Cationized Cellulose (ii) Added (g) | Amount of Propylene Oxide Added (g) | Reaction Time (hr) | Mean Degree of Polymerization | Chlorine Content (%) | Content of Hydroxypropoxy Group (%) |
| Production Example I-1 | 50 | 5 | 152.6 | 72.5 | 20 | 739 | 3.4 | 43.3 |
| Production Example I-2 | — | — | 100 *1 | 40.8 | 8 | 539 | 3.0 | 32.5 |
| Production Example I-3 | 50 | 5 | 100 | 150 | 18 | 1230 | 1.1 | 62.7 |
| Production Example I-4 | — | — | 220 *1 | 153 | 5 | 964 | 3.3 | 54.4 |
| Production Example I-5 | 50 | 5 | 140 | 20 | 9 | 1326 | 9.3 | 5.2 |

*1: Cationized cellulose (i) was used in place of cationized cellulose (ii).

Production Example I-6

Production of C—HPC (I-6)

(1) Chipping Step

As cellulose, a sheet-like wood pulp (Tembec's Biofloc HV10, having a mean degree of polymerization of 1508, a degree of crystallinity of 74% and a water content of 7.0%) was pelletized with a sheet pelletizer (Horai's "SGG-220") into chips of from 3 to 5 mm square.

(2) Cationization Step (1)

559 g of GMAC (corresponding to 0.52 mols per mol of AGU) and 24 g of ion-exchanged water were added to 989 g (water content 7.0%) of the chip-like pulp obtained in the above (1), and mixed in a plastic bag, and then put into a batch-type vibrational mill (Chuo Kakohki's "FV-10": chamber total volume 35 L; 63 rods of SUS304 each having a diameter of 30 mm and a length of 510 mm and having a circular cross section; filling rate 64%). This was ground for 12 minutes (frequency 20 Hz, vibrational amplitude 8 mm, temperature 10 to 40° C.) thereby giving a powdery mixture of cellulose and GMAC.

136.2 g (corresponding to 0.60 mols per mol of AGU) of granular sodium hydroxide (effective content 100%) was put into the vibrational mill. Again this was ground for 112 minutes to give a cationized cellulose.

(3) Hydroxypropylation Step 95.0 g of the cationized cellulose obtained in the above (2) was put into the kneader equipped with a reflux tube used in Production Example I-1, the kneader was heated up to 70° C., and with stirring, 35.4 g (corresponding to 2.0 mols per mol of AGU) of propylene oxide was dropwise added thereto, and the reaction was continued for 7 hours until the propylene oxide was consumed and the reflux flow stopped. After the reaction, the reaction mixture was taken out of the kneader to give 120.6 g of a pale brown crude C—HPC powder.

(4) Cationization Step (2)

16.2 g (corresponding to 3.5 mols per mol of AGU) of GMAC was added to 10.6 g of the crude C—HPC powder obtained in the above (3), mixed in a mortar, and then ripened in a thermostat chamber at 50° C. for 24 hours. The obtained crude C—HPC was dispersed in 100 g of a mixed solvent of water/ethanol/isopropyl alcohol=5/45/50 (by weight), then neutralized with acetic acid added thereto, and purified through precipitation. The precipitate was collected through filtration, and dried under reduced pressure overnight in a drier at 60° C. thereby giving a pale brown bulky crude C—HPC (I-6).

For the purpose of determining the degree of substitution with propyleneoxy group and with cationized ethyleneoxy group, the product was purified through a dialytic membrane (molecular weight cut off, 1000), and then the aqueous solution was freeze-dried to give a pure C—HPC (I-6).

Through elementary analysis thereof, the chlorine content of the obtained pure C—HPC (I-6) was 9.1%. The hydroxypropoxy group content was 25.1%. The degree of substitution with cationized ethyleneoxy group and the degree of substitution with propyleneoxy group were calculated to be 1.00 and 1.3, respectively. The mean degree of polymerization of the pure C—HPC (I-6) was 464. The results are shown in Table 2.

Production Example I-7

Production of C—HPC (I-7)

This is the same as in Production Example I-6 except that the starting pulp was changed as in Table 2, and that the conditions of the cationization step (1), the hydroxypropylation step and the cationization step (2) were changed as in Table 2. The results of the obtained pure C—HPC (I-7) are shown in Table 2.

TABLE 2

| | Starting Pulp | | | | Cationization Step (1) | | | | | Hydroxypropylation Step |
|---|---|---|---|---|---|---|---|---|---|---|
| | Degree of Crystallinity (%) | Mean Degree of Polymerization | Water Content (%) | Amount of Pulp Used (g) | Vibrational Mill | Amount of GMAC Added (g) | Grinding Time (min) | Amount of 48% NaOH Added (g) | Amount of Granular NaOH Added (g) | Grinding Time (min) | Amount of Cationized Cellulose Used (g) |
| Production Example I-6 | 74 | 1508 | 7.0 | 989 | FV-10 | 559 | 12 | — | 136.2 | 112 | 95 |
| Production Example I-7 | 77 | 191 | 7.0 | 100 | MB-1 | 60.8 | 12 | 29.8 | — | 140 | 190 |

| | Hydroxypropylation Step | | Cationization Step (2) | | | | Physical Properties of C-HPC | | |
|---|---|---|---|---|---|---|---|---|---|
| | Amount of Propylene Oxide Added (g) | Reaction Time (hr) | Amount of Crude C-HPC Powder Used (g) | Amount of GMAC Added (g) | Ripening Temperature (° C.) | Ripening Time (hr) | Mean Degree of Polymerization | Chlorine Content (%) | Content of Hydroxypropoxy Group (%) |
| Production Example I-6 | 35.4 | 7 | 10.6 | 16.2 | 50 | 24 | 464 | 9.1 | 25.1 |
| Production Example I-7 | 18 | 2 | 45 | 152 | 50 | 24 | 214 | 15.7 | 3.3 |

Production Example I-8

Production of C—HPC (I-8)

(1) Low-Crystalline Powdery Cellulose Production Step

A sheet-like wood pulp (Tembec's Biofloc HV+, having a mean degree of polymerization of 1770, a degree of crystallinity of 74% and a water content of 7.0%) was shredded with a shredder (Meiko Shokai's "MSX2000-IVP440F") into chips of from 3 to 5 mm square. Subsequently, this was dried under reduced pressure at 50° C. for 12 hours to give a chip-like dry pulp (water content 0.4%).

Next, 100 g of the obtained chip-like dry pulp was put into the batch-type vibrational mill used in Production Example I-1. This was ground for 35 minutes at a frequency 20 Hz, a vibrational amplitude of 8 mm, and a temperature falling within a range of from 30 to 70° C. to give a powdery cellulose (having a degree of crystallinity of 0%, a mean degree of polymerization of 836, a mean particle size of 52 μm and a water content of 1.0%).

(2) Cationization Step 46.9 g (corresponding to 0.4 mols per mol of AGU) of GMAC was added to 100 g of the powdery cellulose obtained in the above (1), and mixed in a mortar. Subsequently, 5.14 g (corresponding to 0.1 mols per mol of AGU) of an aqueous 48% sodium hydroxide solution and 18 g of ion-exchanged water were added thereto and mixed. The resulting mixture was put into the kneader used in Production Example I-1, and stirred at 50° C. for 4 hours to give 170 g of a cationized cellulose.

(3) Hydroxypropylation Step 170 g of the cationized cellulose obtained in the above (2) was heated at 70° C., and with stirring, 4.7 g (corresponding to 0.1 mols per mol of AGU) of an aqueous 48% sodium hydroxide solution and 16.4 g of ion-exchanged water were added thereto. Further, 101 g (corresponding to 3.0 mols per mol of AGU) of propylene oxide was dropwise added thereto and reacted for 24 hours until the propylene oxide was consumed and the reflux flow stopped. After the reaction, the cellulose kept a flowable powdery state. 10.0 g of the reaction product was sampled and neutralized with acetic acid to give a pale brown solid. The neutralized product was purified through a dialytic membrane (molecular weight cut off, 1000), and then the aqueous solution was freeze-dried to give a pure C—HPC (I-8).

Through elementary analysis thereof, the chlorine content of the obtained pure C—HPC (I-8) was 2.1%. The hydroxypropoxy group content was 49.2%. The degree of substitution with cationized ethyleneoxy group and the degree of substitution with propyleneoxy group were calculated to be 0.18 and 2.0, respectively. The mean degree of polymerization of the pure C—HPC (I-8) was 832. The results are shown in Table 3.

Production Example I-9

Production of C—HPC (I-9)

This is the same as in Production Example I-8 except that the starting pulp was changed as in Table 3, and that the conditions of the low-crystalline powdery cellulose production step, the cationization step and the hydroxypropylation step were changed as in Table 3. The results of the obtained pure C—HPC (I-9) are shown in Table 3.

Production Example I-10

Production of C—HPC (I-10)

This is the same as in Production Example I-8 except that the condition of the hydroxypropylation step was changed as in Table 3. The results of the obtained pure C—HPC (I-10) are shown in Table 3.

TABLE 3

| | Staring Pulp | | | Low-Crystalline Powdery Cellulose Production Step | | | Physical Properties of Powdery Cellulose | | | |
| | | | | | Chip-like | Grinding | | | | |
| | Degree of Crystallinity (%) | Mean Degree of Polymerization | Water Content (%) | Shredding Step Drying Step | Dry Pulp Water Content (%) | Step Grinding Time (min) | Degree of Crystallinity (%) | Mean Degree of Polymerization | Mean Particle Size (μm) | Water Content (%) |
|---|---|---|---|---|---|---|---|---|---|---|
| Production Example I-8 | 76 | 1770 | 7.0 | at 50° C. under reduced pressure, for 12 hours | 0.4 | 35 | 0 | 836 | 52 | 1.0 |
| Production Example I-9 | 76 | 1420 | 7.0 | at 50° C. under reduced pressure, for 12 hours | 0.4 | 20 | 0 | 574 | 52 | 1.0 |
| Production Example I-10 | 76 | 1770 | 7.0 | at 50° C. under reduced pressure, for 12 hours | 0.4 | 35 | 0 | 836 | 52 | 1.0 |

TABLE 3-continued

|  |  | Cationization Step | | | Hydroxypropylation Step | | Physical Properties of C-HPC | | |
|---|---|---|---|---|---|---|---|---|---|
|  |  | Amount of Powdery Cellulose Used (g) | Amount of 48% NaOH Added (g) | Amount of GMAC Added (g) | Amount of 48% NaOH Added (g) | Amount of Propylene Oxide Added (g) | Mean Degree of Polymerization | Chlorine Content (%) | Content of Hydroxypropoxy Group (%) |
|  | Production Example I-8 | 100 | 5.1 | 46.9 | 4.7 | 101 | 832 | 2.1 | 49.2 |
|  | Production Example I-9 | 100 | 10.2 | 33.6 | — | 53.2 | 646 | 2.3 | 37.1 |
|  | Production Example I-10 | 100 | 5.1 | 46.9 | 4.7 | 89 | 779 | 2.2 | 45.7 |

Production Example I-11

Production of Cationized Cellulose (I-1)

A cationized cellulose (I-1) was produced in the same manner as in Production Example I-5 except that the propylene oxide addition was omitted.

Production Example I-12

Production of C—HPC (I-11)

(1) Chipping Step

A sheet-like wood pulp (Tembec's Biofloc HV+, having a mean degree of polymerization of 1481, a degree of crystallinity of 74% and a water content of 4.6%) was pelletized with a sheet pelletizer (Horai's "SGG-220") into chips of from 3 to 5 mm square.

(2) Alkali Cellulose Production Step 100 g of the chip-like pulp obtained in the above step (1) and 23.6 g of 0.7-mm granular NaOH (corresponding to 1.0 mol per mol of AGU) were put into a batch-type vibrational mill (Chuo Kakohki's "MB-1": chamber total volume 3.5 L; 13 rods of SUS304 each having a diameter of 30 mm and a length of 218 mm and having a circular cross section; filling rate 57%), and ground therein for 15 minutes (frequency 20 Hz, vibrational amplitude 8 mm, temperature 30 to 70° C.). Thus obtained, the ground cellulose/NaOH mixture (mean particle size of cellulose: 65 μm) was transferred into a mortar, and sprayed with 50 g of water. The water content of the ground cellulose/NaOH mixture was 57% relative to the cellulose therein. This was ground with a pestle at 20° C. for 5 minutes to give an alkali cellulose (mean degree of polymerization: 1175).

(3) Hydroxypropylation Step

The alkali cellulose obtained in the above step (2) was put into a kneader equipped with a reflux tube and a dropping funnel (Irie Shokai's PNV-1 Model, capacity 1.0 L), and 85.7 g of propylene oxide (corresponding to 2.5 mols per mol of AGU) was put thereinto and reacted at 50° C. for 6 hours with stirring. For the reaction, propylene oxide was dropwise added taking 5 hours, and the system was then ripened for 1 hour.

(4) Cationization Step 5.8 g of the reaction mixture obtained in the above step (3) was taken into a mortar, and 2.10 g of aqueous 65% 3-chloro-2-hydroxypropyltrimethylammonium chloride solution (by Yokkaichi Gosei) (corresponding to 0.50 mols per mol of AGU) was added thereto and mixed for 5 minutes, and thereafter this was transferred into a 50-ml glass bottle and reacted therein at 50° C. for 7 hours to give a crude C—HPC.

5.0 g of the crude C—HPC powder was sampled and neutralized with lactic acid. For the purpose of determining the degree of substitution with propyleneoxy group and with cationized ethyleneoxy group, the neutralized product was purified through a dialytic membrane (molecular weight cut off, 1000), and then the aqueous solution was freeze-dried to give a pure C—HPC (I-11).

Through elementary analysis thereof, the chlorine content of the obtained pure C—HPC (I-11) was 3.3% and the hydroxypropoxy group content was 38.8%. The degree of substitution with cationized ethyleneoxy group and the degree of substitution with propyleneoxy group were calculated to be 0.27 and 1.5, respectively. The mean degree of polymerization was 643. The results are shown in Table 4.

TABLE 4

|  | Starting Pulp | | | | Alkali Cellulose Production Step | | | | | Physical Properties of Alkali Cellulose | |
|---|---|---|---|---|---|---|---|---|---|---|---|
|  | Degree of Crystallinity (%) | Mean Degree of Polymerization | Water Content (%) | Vibrational Mill | Amount of Pulp Used (g) | Grinding Time (min) | Amount of Granular NaOH Used (g) | Amount of Water Added (g) | Particle Size (μm) | Mean Degree of Polymerization |
| Production Example I-12 | 74 | 1481 | 4.6 | MB-1 | 100 | 15 | 23.6 | 50 | 65 | 1175 |

TABLE 4-continued

| | Hydroxypropylation Step | | | Cationization Step | | | | Physical Properties of C-HPC | | |
|---|---|---|---|---|---|---|---|---|---|---|
| | Amount of Propylene Oxide added (g) | Reaction Temperature (° C.) | Reaction Time (hr) | Amount of Reaction Mixture Used (g) | Amount of Aqueous Ammonium Chloride Solution Used (g)*1 | Reaction Temperature (° C.) | Reaction Time (hr) | Mean Degree of Polymerization | Chlorine Content (%) | Content of Hydroxy-propoxy Group (%) |
| Production Example I-12 | 85.7 | 50 | 6 | 5.8 | 2.10 | 50 | 7 | 643 | 3.3 | 38.8 |

*1Amount of aqueous 3-chloro-2-hydroxypropyltrimethylammonium chloride solution used (g).

Production Example I-13

Production of C—HPC (I-12)

(1) Low-Crystalline Powdery Cellulose Production Step

A chip-like pulp of from 3 to 5 mm square was obtained in the same manner as in Production Example I-12(1). One kg of the obtained chip-like pulp was put into a drier (Advantec Toyo's trade name, VO-402) and dried therein at 105° C. for 2 hours to give a dry chip-like pulp (water content 0.8%).

920 g of the obtained dry chip-like pulp was put into a batch-type vibrational mill (Chuo Kakohki's "FV-10": chamber total volume 35 L; 63 rods of SUS304 each having a diameter of 30 mm and a length of 510 mm and having a circular cross section; filling rate 65%). This was ground for 10 minutes (frequency 20 Hz, vibrational amplitude 8 mm, temperature 10 to 40° C.) to give a powdery cellulose (having a degree of crystallinity of 14%, a mean degree of polymerization of 1198, and a water content of 1.0%).

(2) Alkali Cellulose Production Step 369 g of the powdery cellulose obtained in the above step (1) was put into a mixer (Matsubo's "Ledige Mixer", capacity 5 L), and with stirring at 250 rpm for the main blade and at 2500 rpm for the chopper blade, this was sprayed with 212 g of an aqueous 42.5% sodium hydroxide solution (corresponding to 1.0 mol of NaOH per mol of AGU, and 33% of water relative to cellulose) taking 1.5 minutes. After the spraying, the inner temperature was elevated up to 50° C., and the system was ripened for 3 hours to give an alkali cellulose.

(3) Hydroxypropylation Step 607 g of the alkali cellulose obtained in the above step (2) was heated up to 50° C. in the Ledige mixer with stirring at 50 rpm for the main blade and at 400 rpm for the chopper blade, and thereafter 187 g of propylene oxide (corresponding to 1.6 mols per mol of AGU) was dropwise added thereto taking 3.5 hours. After the addition, this was ripened at 50° C. for 2 hours.

(4) Cationization Step 11.4 g of the reaction mixture obtained in the above step (3) was taken into a mortar, and 4.31 g of an aqueous 65% 3-chloro-2-hydroxypropyltrimethylammonium chloride solution (corresponding to 0.5 mols per mol of AGU) and 0.84 g of ion-exchanged water were added thereto and mixed for 5 minutes, and thereafter this was transferred into a 50-ml glass bottle and reacted therein at 50° C. for 5 hours to give a crude C—HPC. The crude C—HPC powder was neutralized, purified and freeze-dried in the same manner as in Production Example I-12(4) to give a pure C—HPC (I-12).

Through elementary analysis thereof, the chlorine content of the obtained pure C—HPC (I-12) was 4.3%. The hydroxypropoxy group content was 24.3%. The degree of substitution with cationized ethyleneoxy group and the degree of substitution with propyleneoxy group were calculated to be 0.25 and 0.8, respectively. The mean degree of polymerization was 659. The results are shown in Table 5.

Production Example I-14

Production of C—HPC (I-13)

(1) Low-Crystalline Powdery Cellulose Production Step

A powdery cellulose (having a degree of crystallinity of 14%, a mean degree of polymerization of 1198 and a water content of 1.0%) was obtained in the same manner as in Production Example I-13(1).

(2) Alkali Cellulose Production Step

An alkali cellulose was obtained in the same manner as in Production Example I-13(2), except that 530.5 g of the powdery cellulose obtained in the above step (1) and 307 g of an aqueous 42.5% sodium hydroxide solution (corresponding to 1.0 mol of NaOH per mol of AGU and 34% of water relative to cellulose) were used.

(3) Hydroxypropylation Step 825 g of the alkali cellulose obtained in the above step (2) was heated up to 50° C. with stirring in the above-mentioned Ledige mixer at 50 rpm for the main blade and at 400 rpm for the chopper blade, and thereafter 467 g of propylene oxide (corresponding to 2.6 mols per mol of AGU) was dropwise added thereto taking 6 hours. After the addition, this was ripened at 50° C. for 2 hours.

(4) Cationization Step 12.3 g of the reaction mixture obtained in the above step (3) was taken into a mortar, and 4.31 g of aqueous 65% 3-chloro-2-hydroxypropyltrimethylammonium chloride solution (corresponding to 0.5 mols per mol of AGU) and 0.84 g of ion-exchanged water were added thereto and mixed for 5 minutes, and thereafter this was transferred into a 50-ml glass bottle and reacted therein at 50° C. for 5 hours to give a crude C—HPC. The crude C—HPC powder was neutralized, purified and freeze-dried in the same manner as in Production Example I-12(4) to give a pure C—HPC (I-13).

Through elementary analysis thereof, the chlorine content of the obtained pure C—HPC (I-13) was 2.5%. The hydroxypropoxy group content was 38.5%. The degree of substitution with cationized ethyleneoxy group and the degree of substitution with propyleneoxy group were calculated to be 0.19 and 1.4, respectively. The mean degree of polymerization was 1186. The results are shown in Table 5.

TABLE 5

| | Starting Pulp | | | Low-Crystalline Powdery Cellulose Production Step | | | | | Physical Properties of Powdery Cellulose | | | Alkali Cellulose Production Step | | | |
|---|---|---|---|---|---|---|---|---|---|---|---|---|---|---|---|
| | Mean Degree of Crystallinity (%) | Degree of Polymerization | Water Content (%) | Vibrational Mill | Drying Time (hr) | Drying Temperature (° C.) | Grinding Time (min) | | Degree of Crystallinity (%) | Mean Degree of Polymerization | Water Content (%) | Amount of Powdery Cellulose Used (g) | Amount 42.5% NaOH Solution Used (g) | Ripening Temperature (° C.) | Ripening Time (min) |
| Production Example I-13 | 74 | 1481 | 4.6 | FV-10 | 2 | 105 | 10 | | 14 | 1198 | 1 | 369 | 212 | 50 | 3 |
| Production Example I-14 | 74 | 1481 | 4.6 | FV-10 | 2 | 105 | 10 | | 14 | 1198 | 1 | 530.5 | 307 | 50 | 3 |

| | Hydroxypropylation Step | | | | Cationization Step | | | | Physical Properties of C-HPC | | |
|---|---|---|---|---|---|---|---|---|---|---|---|
| | Amount of Alkali Cellulose Used (g) | Amount of Propylene Oxide Used (g) | Reaction Temperature (° C.) | Reaction Time (hr) | Amount of Reaction Mixture Used (g) | Amount of Aqueous Ammonium Chloride Solution Used (g)*1 | Reaction Temperature (° C.) | Reaction Time (hr) | Mean Degree of Polymerization | Chlorine Content (%) | Content of Hydroxypropoxy Group (%) |
| Production Example I-13 | 607 | 187 | 50 | 5.5 | 11.4 | 4.31 | 50 | 5 | 659 | 4.3 | 24.3 |
| Production Example I-14 | 825 | 467 | 50 | 8 | 12.3 | 4.31 | 50 | 5 | 1186 | 2.5 | 38.5 |

*1 Amount of aqueous 3-chloro-2-hydroxypropyltrimethylammonium chloride solution used (g).

The mean degree of polymerization, the degree of substitution with cationized ethyleneoxy group and the degree of substitution with propyleneoxy group of C—HPC obtained in Production Examples I-1 to 10, and 12 to 14, and the mean degree of polymerization and the degree of substitution with cationized ethyleneoxy group of the cationized cellulose (I-1) are summarized in Table 6.

TABLE 6

| | | Mean Degree of Polymerization | Degree of Substitution with Cationized EO *1 | Degree of Substitution with PO *2 | 2% Viscosity *3 |
|---|---|---|---|---|---|
| Production Example I-1 | C-HPC (I-1) | 739 | 0.30 | 1.8 | — |
| Production Example I-2 | C-HPC (I-2) | 539 | 0.22 | 1.1 | 171 |
| Production Example I-3 | C-HPC (I-3) | 1230 | 0.11 | 2.9 | — |
| Production Example I-4 | C-HPC (I-4) | 964 | 0.35 | 2.7 | 23 |
| Production Example I-5 | C-HPC (I-5) | 1326 | 0.75 | 0.2 | 13600 |
| Production Example I-6 | C-HPC (I-6) | 464 | 1.00 | 1.3 | 32 |
| Production Example I-7 | C-HPC (I-7) | 214 | 2.36 | 0.2 | 9 |
| Production Example I-8 | C-HPC (I-8) | 832 | 0.18 | 2.0 | — |
| Production Example I-9 | C-HPC (I-9) | 646 | 0.17 | 1.3 | — |
| Production Example I-10 | C-HPC (I-10) | 779 | 0.18 | 1.8 | — |
| Production Example I-11 | Cationized Cellulose (I-1) | 1288 | 0.77 | 0.0 | 1049 |

TABLE 6-continued

| | | Mean Degree of Polymerization | Degree of Substitution with Cationized EO *1 | Degree of Substitution with PO *2 | 2% Viscosity *3 |
|---|---|---|---|---|---|
| Production Example I-12 | C-HPC (I-11) | 643 | 0.27 | 1.5 | — |
| Production Example I-13 | C-HPC (I-12) | 659 | 0.25 | 0.8 | — |
| Production Example I-14 | C-HPC (I-13) | 1186 | 0.25 | 1.5 | — |

*1: Degree of substitution with cationized ethyleneoxy group.
*2: Degree of substitution with propyleneoxy group.
*3: Viscosity of 2% C-HPC (mPa · s)

Examples I-1 to 38, and 77 to 79

Production and Evaluation of Conditioner

Any of C—HPC (I-1) to (I-13) was used as the component (A), and conditioners each having the composition shown in Tables 7 to 11 were produced according to an ordinary method.

Concretely, in Examples I-1 to 25, 34, 35 and 77 to 79, the component (A) was dissolved or uniformly dispersed in water to prepare an aqueous 2% polymer solution. A moderate amount of water and the surfactant (C) were taken in a beaker, heated at 80° C. and mixed to prepare an aqueous solution, and this was added to the above-mentioned, aqueous polymer solution and uniformly mixed. The oil (B), after melted, was added thereto, stirred and emulsified for 30 minutes, and cooled. Finally, water that had evaporated away by heating was replenished and the pH of the mixture was measured. The pH was controlled to be 5 with a pH regulator (aqueous 50% citric acid solution).

In Examples 1-26 to 33, the component (A) was dissolved or uniformly dispersed in water to prepare an aqueous 2% polymer solution. Water and the surfactant (C) were taken in a beaker, heated at 80° C. and mixed to prepare an aqueous solution, and this was added to the above-mentioned, aqueous polymer solution and uniformly mixed. Cetyl alcohol and stearyl alcohol, after melted, were added thereto, stirred and emulsified for 30 minutes, and cooled down to 50 to 60° C. Next, a silicone emulsion was added thereto and uniformly mixed, and cooled. Finally, water that had evaporated away by heating was replenished and the pH of the mixture was measured. The pH was controlled to be 5 with a pH regulator (aqueous 50% citric acid solution).

In Examples I-36 to 38, the component (A) was dissolved or uniformly dispersed in water to prepare an aqueous 2% polymer solution. A moderate amount of water, the surfactant (C) and an equimolar amount of a pH regulator (aqueous 50% citric acid solution) were added thereto, then uniformly mixed, and heated at 80° C. The oil (B) and the component (C), after melted, were added thereto, stirred and emulsified for 30 minutes, and cooled. Finally, water that had evaporated away by heating was replenished and the pH of the mixture was measured. The pH was controlled to be 5 with a pH regulator (aqueous 50% citric acid solution).

Hair tresses were washed with plain shampoo mentioned below, fully wetted with warm water at 35 to 40° C., and thereafter 1 g of the conditioner of Examples I-1 to 38, and 77 to 79 was applied thereto and spread evenly thereover. Subsequently, the hair tresses were rinsed with warm water for 30 seconds, wiped with a towel to remove water, combed, and dried with warm air from a drier, and again combed for final dressing to give a sample of tresses for evaluation.

Five panelists tested and evaluated the tresses for the finger combability, oily feeling and manageability thereof according to the following evaluation criteria and evaluation methods. The results are shown in Tables 7 to 11.
(Composition of Plain Shampoo)

| (Component) | (%) |
|---|---|
| Na polyoxyethylene lauryl ether sulfate(42.0% as EMAL E-27C (by Kao, effective content, 27% by weight)) | 11.3 |
| Cocoyl fatty acid N-methylethanolamide(AMINONE C-11S (by Kao) | 3.0 |
| Citric acid | 0.2 |
| Methylparaben | 0.3 |
| Pure water | balance |
| Total | 100.0 |

(Production of Plain Shampoo)
The components were taken in a beaker, heated at 80° C. and mixed, and after their uniform dissolution was confirmed, the mixture was cooled to give plain shampoo.
(Evaluation Criteria, Evaluation Methods)
Finger Combability
  5: Excellent finger combability.
  4: Good finger combability.
  3: Average (standard: finger combability in Comparative Examples 1 to 7).
  2: Bad finger combability.
  1: Extremely bad finger combability.
Oily Feeling
  5: Not oily.
  4: Not so much oily.
  3: Average (standard: oily feeling in Comparative Examples 1 to 7).
  2: Somewhat oily.
  1: Oily.
Manageability
  5: The hair was very well manageable.
  4: The hair was well manageable.
  3: Average (standard: manageability in Comparative Examples 1 to 7).
  2: The hair was poorly manageable.
  1: The hair was not manageable at all.

The finger combability, the oily feeling and the manageability of the sample of Comparative Examples I-7 was given a standard score 3; and the scores given by 5 panelists to each sample were averaged to give the mean score of each sample.

The samples having a mean score of 3.4 or more can be said to be obviously excellent in the evaluation test.

Comparative Examples I-1 to 12

Conditioners each having the composition as in Tables 7 to 9 were produced in the same manner as in Example I-1, except that the component (A) in Example I-1 was not added (Comparative Examples I-10 to 12), or a different polymer as in Table 7 was used in place of the component (A) (Comparative Examples I-1 to 9). The pH of the conditioners of Comparative Examples I-1 to 12 was controlled to be 5. The conditioners of Comparative Examples I-1 to 12 were tested and evaluated in the same manner as in Examples I-1 to 38 and 77 to 79. The results are shown in Tables 7 to 9.

TABLE 7

| Hair Cosmetic (Conditioner) | | | Example I-1 | I-2 | I-3 | I-4 | I-5 | I-6 | I-7 | I-8 | I-9 | I-10 | I-77 | I-78 | I-79 | Comparative Example I-1 | I-2 | I-3 | I-4 | I-5 | I-6 | I-7 | I-8 | I-9 |
|---|---|---|---|---|---|---|---|---|---|---|---|---|---|---|---|---|---|---|---|---|---|---|---|---|
| Constitutive Components (part by mass) | Component (A) | C-HPC (I-1) | 0.5 | | | | | | | | | | | | | | | | | | | | | |
| | | C-HPC (I-2) | | 0.5 | | | | | | | | | | | | | | | | | | | | | |
| | | C-HPC (I-3) | | | 0.5 | | | | | | | | | | | | | | | | | | | | |
| | | C-HPC (I-4) | | | | 0.5 | | | | | | | | | | | | | | | | | | | |
| | | C-HPC (I-5) | | | | | 0.5 | | | | | | | | | | | | | | | | | | |
| | | C-HPC (I-6) | | | | | | 0.5 | | | | | | | | | | | | | | | | | |
| | | C-HPC (I-7) | | | | | | | 0.5 | | | | | | | | | | | | | | | | |
| | | C-HPC (I-8) | | | | | | | | 0.5 | | | | | | | | | | | | | | | |
| | | C-HPC (I-9) | | | | | | | | | 0.5 | | | | | | | | | | | | | | |
| | | C-HPC (I-10) | | | | | | | | | | 0.5 | | | | | | | | | | | | | |
| | | C-HPC (I-11) | | | | | | | | | | | 0.5 | | | | | | | | | | | | |
| | | C-HPC (I-12) | | | | | | | | | | | | 0.5 | | | | | | | | | | | |
| | | C-HPC (I-13) | | | | | | | | | | | | | 0.5 | | | | | | | | | | |
| | | Cationized Cellulose (I-1) | | | | | | | | | | | | | | 0.5 | | | | | | | | | |
| | | Cationized Hydroxyethyl Cellulose *1 | | | | | | | | | | | | | | | 0.5 | | | | | | | | |
| | | Hydroxyethyl Cellulose *2 | | | | | | | | | | | | | | | | 0.5 | | | | | | | |
| | | Hydroxypropyl Cellulose *3 | | | | | | | | | | | | | | | | | 0.5 | | | | | | |
| | | Dimethyldiallylammonium Chloride/Acrylamide Copolymer *4 | | | | | | | | | | | | | | | | | | 0.5 | | | | | |
| | | Dimethyldiallylammonium Chloride/Vinylpyrrolidone/Vinylimidazole Copolymer *5 | | | | | | | | | | | | | | | | | | | 0.5 | | | | |
| | | Cationized Starch *6 | | | | | | | | | | | | | | | | | | | | 0.5 | | | |
| | | Cationized Guar Gum *7 | | | | | | | | | | | | | | | | | | | | | 0.5 | | |
| | | Cationized Hydroxypropyl Guar Gum *8 | | | | | | | | | | | | | | | | | | | | | | 0.5 | |
| | Component (B) | Cetyl Alcohol | 1.3 | 1.3 | 1.3 | 1.3 | 1.3 | 1.3 | 1.3 | 1.3 | 1.3 | 1.3 | 1.3 | 1.3 | 1.3 | 1.3 | 1.3 | 1.3 | 1.3 | 1.3 | 1.3 | 1.3 | 1.3 | 1.3 |
| | | Stearyl Alcohol | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 |
| | Component (C) | Behenyltrimethylammonium Chloride | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 |
| | | pH Regulator | | | | | | | | | | | adequate dose | | | | | | | | | | | | |
| | | Pure Water | | | | | | | | | | | balance | | | | | | | | | | | | |
| Evaluation Results (after dried) | | Finger combability | 5.0 | 5.0 | 3.6 | 4.0 | 4.0 | 5.0 | 3.6 | 3.6 | 3.4 | 3.6 | 5 | 4.6 | 5 | 2.0 | 3.6 | 2.6 | 2.6 | 3.0 | 3.6 | 3.0 | 3.0 | 3.0 |
| | | Oily feeling | 5.0 | 5.0 | 5.0 | 4.6 | 5.0 | 5.0 | 4.4 | 4.4 | 3.4 | 3.4 | 4.6 | 4.6 | 5 | 4.0 | 2.0 | 3.0 | 3.0 | 3.0 | 3.0 | 3.0 | 2.4 | 2.0 |
| | | Manageability | 4.0 | 4.0 | 3.6 | 4.0 | 4.0 | 5.0 | 3.6 | 3.6 | 3.4 | 3.6 | 3.6 | 3.6 | 4 | 2.0 | 3.6 | 3.0 | 3.0 | 2.0 | 2.0 | 3.0 | 2.4 | 2.6 |

*1: Nalco's trade name, Merquat 10
*2: Daicel's trade name, HEC-SE850K
*3: Nippon Soda's trade name, CELNY M
*4: Nalco's trade name, MERQUAT 550
*5: BASF's trade name, LUVIQUAT SENSATION
*6: Nalco's trade name, SENSOMER CI50
*7: Sansho's trade name, JAGUAR C13S
*8: Sansho's trade name, JAGUAR C162

TABLE 8

| | | Hair Cosmetic (Conditioner) | Example I-11 | I-12 | I-13 | I-14 | I-15 | I-16 | Comparative Example I-10 |
|---|---|---|---|---|---|---|---|---|---|
| Constitutive Components (part by mass) | Component (A) | C-HPC (I-2) | 0.001 | 0.01 | 0.1 | 0.3 | 1 | 3 | |
| | Component (B) | Cetyl Alcohol | 1.3 | 1.3 | 1.3 | 1.3 | 1.3 | 1.3 | 1.3 |
| | | Stearyl Alcohol | 2.6 | 2.6 | 2.6 | 2.6 | 2.6 | 2.6 | 2.6 |
| | Component (C) | Behenyltrimethylammonium Chloride | 1.5 | 1.5 | 1.5 | 1.5 | 1.5 | 1.5 | 1.5 |
| | | pH Regulator | adequate dose | | | | | | |
| | | Pure Water | balance | | | | | | |
| Evaluation Results (after dried) | | Finger combability | 3.6 | 4.0 | 5.0 | 5.0 | 5.0 | 4.0 | 2.4 |
| | | Oily feeling | 4.0 | 5.0 | 5.0 | 5.0 | 3.6 | 3.6 | 3.0 |
| | | Manageability | 4.0 | 4.0 | 4.0 | 4.0 | 4.0 | 3.6 | 3.0 |

TABLE 9

| | | Hair Cosmetic (Conditioner) | Example I-17 | I-18 | I-19 | I-20 | I-21 | I-22 | I-23 | I-24 |
|---|---|---|---|---|---|---|---|---|---|---|
| Constitutive Components (part by mass) | Component (A) | C-HPC (I-1) | 0.5 | 0.5 | 0.5 | 0.5 | 0.5 | 0.5 | 0.5 | 0.5 |
| | | C-HPC (I-2) | | | | | | | | |
| | Component (B) | Cetyl Alcohol | | | | | | | | |
| | | Stearyl Alcohol | 4.0 | 4.0 | 4.0 | 4.0 | 4.0 | 4.0 | 4.0 | 4.0 |
| | | Isopropyl Palmitate | 1.0 | | | | | | | |
| | | Sunflower Oil *1 | | 1.0 | | | | | | |
| | | Squalane *2 | | | 1.0 | | | | | |
| | | Polyoxypropylene (Pop = 3) N-octyl Ether | | | | 1.0 | | | | |
| | | Polyoxypropylene (Pop = 10) Lauryl Ether | | | | | 1.0 | | | |
| | | Paraffin Wax *3 | | | | | | 1.0 | | |
| | | Myristyl Myristate | | | | | | | 1.0 | |
| | | Cetyl Palmitate | | | | | | | | 1.0 |
| | | Stearyl Stearate | | | | | | | | |
| | | High-Polymerization Dimethylsiloxane *4 | | | | | | | | |
| | | High-Polymerization Dimethylsiloxane *5 | | | | | | | | |
| | | High-Polymerization Dimethylsiloxane *6 | | | | | | | | |
| | | Amino-Modified High-Polymerization Dimethyl Polysiloxane *7 | | | | | | | | |
| | Component (C) | Behenyltrimethylammonium Chloride | 1.5 | 1.5 | 1.5 | 1.5 | 1.5 | 1.5 | 1.5 | 1.5 |
| | | pH Regulator | adequate dose | | | | | | | |
| | | Pure Water | balance | | | | | | | |
| Evaluation Results (after dried) | | Finger combability | 4.6 | 4.0 | 4.6 | 5.0 | 4.6 | 5.0 | 5.0 | 5.0 |
| | | Oily feeling | 4.4 | 4.0 | 4.0 | 5.0 | 5.0 | 4.0 | 5.0 | 5.0 |
| | | Manageability | 4.6 | 5.0 | 5.0 | 5.0 | 5.0 | 5.0 | 5.0 | 4.0 |

| | | Hair Cosmetic (Conditioner) | Example I-25 | I-26 | I-27 | I-28 | I-29 | I-30 | Comparative Example I-11 | I-12 |
|---|---|---|---|---|---|---|---|---|---|---|
| Constitutive Components (part by mass) | Component (A) | C-HPC (I-1) | 0.5 | 0.5 | | | | | | |
| | | C-HPC (I-2) | | | 0.5 | 0.5 | 0.5 | 0.5 | | |
| | Component (B) | Cetyl Alcohol | | | 1.3 | 1.3 | 1.3 | 1.3 | 1.3 | |
| | | Stearyl Alcohol | 4.0 | 4.0 | 2.6 | 2.6 | 2.6 | 2.6 | 2.6 | 4.0 |
| | | Isopropyl Palmitate | | | | | | | | |
| | | Sunflower Oil *1 | | | | | | | | |
| | | Squalane *2 | | | | | | | | |
| | | Polyoxypropylene (Pop = 3) N-octyl Ether | | | | | | | | |
| | | Polyoxypropylene (Pop = 10) Lauryl Ether | | | | | | | | |
| | | Paraffin Wax *3 | | | | | | | | |
| | | Myristyl Myristate | | | | | | | | |
| | | Cetyl Palmitate | | | | | | | | |
| | | Stearyl Stearate | 1.0 | | | | | | | |
| | | High-Polymerization Dimethylsiloxane *4 | | | 1.0 | | | | 1.0 | 1.0 |
| | | High-Polymerization Dimethylsiloxane *5 | | | | 1.0 | | | | |
| | | High-Polymerization Dimethylsiloxane *6 | | | | | 1.0 | | | |
| | | Amino-Modified High-Polymerization Dimethyl Polysiloxane *7 | | 1.0 | | | | 1.0 | | |

TABLE 9-continued

| | | | | | | | | | |
|---|---|---|---|---|---|---|---|---|---|
| Component (C) | Behenyltrimethylammonium Chloride | 1.5 | 1.5 | 1.5 | 1.5 | 1.5 | 1.5 | 1.5 | 1.5 |
| | pH Regulator | adequate dose | | | | | | | |
| | Pure Water | balance | | | | | | | |
| Evaluation Results (after dried) | Finger combability | 4.0 | 5.0 | 4.6 | 5.0 | 5.0 | 5.0 | 4.0 | 4.0 |
| | Oily feeling | 5.0 | 4.0 | 4.6 | 4.0 | 4.0 | 4.0 | 1.4 | 1.4 |
| | Manageability | 4.0 | 5.0 | 5.0 | 5.0 | 5.0 | 5.0 | 3.6 | 3.6 |

*1: Nihon Ryutsu Sangyo's edible sunflower oil
*2: Nikko Chemical's trade name, SQUALANE
*3: Nihon Rosoku's trade name, PARAFFIN WAX 125
*4: Toray Dow Corning's trade name, BY22-029 (effective ingredient 50%)
*5: Shin-etsu Chemical's trade name, KM-902 (effective ingredient 50%)
*6: Toray Dow Corning's trade name, BY22-060 (effective ingredient 60%)
*7: Toray Dow Corning's trade name, SM8904 (effective ingredient 40%)

TABLE 10

| | | | Example | | |
|---|---|---|---|---|---|
| Hair Cosmetic (Conditioner) | | | I-31 | I-32 | I-33 |
| Constitutive Ingredients (part by mass) | Component (A) | C-HPC (I-2) | 0.5 | 0.5 | 0.5 |
| | Component (B) | Cetyl Alcohol | 1.3 | 1.3 | 1.3 |
| | | Stearyl Alcohol | 2.6 | 2.6 | 2.6 |
| | | High-Polymerization Dimethylsiloxane *1 | 0.1 | 4.0 | 10.0 |
| | Component (C) | Behenyltrimethyl-ammonium Chloride | 1.5 | 1.5 | 1.5 |
| | | pH Regulator | adequate dose | | |
| | | Pure Water | balance | | |
| Evaluation Results (after dried) | | Finger combability | 4.6 | 5.0 | 5.0 |
| | | Oily feeling | 4.0 | 3.8 | 3.6 |
| | | Manageability | 4.0 | 4.0 | 5.0 |

*1: Shin-etsu Chemical's trade name, KM-902 (effective ingredient 50%)

TABLE 11

| | | | Example | | | | |
|---|---|---|---|---|---|---|---|
| Hair Cosmetic (Conditioner) | | | I-34 | I-35 | I-36 | I-37 | I-38 |
| Constitutive Ingredients (part by mass) | Component (A) | C-HPC (I-2) | 0.5 | 0.5 | 0.5 | 0.5 | 0.5 |
| | Component (B) | Cetyl Alcohol | 1.3 | 1.3 | 1.3 | 1.3 | 1.3 |
| | | Stearyl Alcohol | 2.6 | 2.6 | 2.6 | 2.6 | 2.6 |
| | Component (C) | Cetyltrimethylammonium Chloride | 1.5 | | | | |
| | | Behenyltrimethylammonium Chloride | | | | | |
| | | Stearoxypropyltrimethylammonium Chloride *9 | | 1.5 | | | |
| | | Stearamidopropyldimethylamine *10 | | | 1.5 | | |
| | | Behanamidopropyldimethylamine *11 | | | | 1.5 | |
| | | Stearyldimethylamine | | | | | 1.5 |
| | | pH Regulator | adequate dose | | | | |
| | | Pure Water | balance | | | | |
| Evaluation Results (after dried) | | Finger combability | 4.6 | 4.6 | 4.6 | 5.0 | 5.0 |
| | | Oily feeling | 5.0 | 5.0 | 5.0 | 5.0 | 5.0 |
| | | Manageability | 4.2 | 5.0 | 5.0 | 5.0 | 5.0 |

*9: Kao's trade name, COATAMINE E-80K (effective ingredient 45%)
*10: Toho Industry's trade name, CATINAL MPAS
*11: Kao's trade name, FARMIN DM-220A From Tables 7 to 11, it is known that the conditioners of Examples I-1 to 38, and 77 to 79 are excellent conditioners satisfying all the requirements of good finger combability and good manageability with no oily feeling after drying.

Examples I-39 to 70

Production and Evaluation of Shampoo

Using C—HPC (I-2) obtained in Production Example I-2, shampoos of Examples I-39 to 70 each having the composition as in Tables 12 to 16 were produced according to an ordinary method.

Concretely, the component (C) and a moderate amount of water were taken in a beaker, heated at 60° C. and dissolved. This was cooled to 50° C., and a polymer liquid prepared in the same manner as in Example I-1 was added thereto and uniformly mixed. The component (B) was added to it, stirred and emulsified for 30 minutes, and cooled. Finally, water that had evaporated away by heating was replenished and the pH was measured. If desired, the pH was controlled to be 7 with a pH regulator (aqueous 50% citric acid solution or aqueous 48% sodium hydroxide solution).

Hair tresses washed with the plain shampoo used in Example I-1 were fully wetted with warm water at 35 to 40° C., and then washed with the shampoo of Examples I-39 to 70, rinsed with warm water, wiped with a towel to remove water, and combed. Subsequently, the hair tresses were dried with warm air of a drier, and again combed for final dressing to give a sample of tresses for evaluation. Five panelists tested and evaluated the tresses for the finger combability, oily feeling and manageability thereof according to the same evaluation criteria and evaluation methods as in Examples I-1 to 38. The results are shown in Tables 12 to 16.

The finger combability, the oily feeling and the manageability of the sample of Comparative Examples I-16 was given a standard score 3; and the scores given by 5 panelists to each sample were averaged to give the mean score of each sample.

The samples having a mean score of 3.4 or more can be said to be obviously excellent in the evaluation test.

Comparative Examples I-13 to 18

Shampoos each having the composition as in Tables 12 to 14 were produced and evaluated in the same manner as in Example I-39, except that, in place of C—HPC (I-2) obtained in Production Example I-2, the component (A) was not added (Comparative Example I-17), or a different polymer as in Tables 12 to 14 was used. The pH of the shampoos of Comparative Examples I-13 to 18 was controlled to be 7. The results are shown in Tables 12 to 14.

TABLE 12

| Hair Cosmetic (Shampoo) | | | Example I-39 | Comparative Example | | | |
|---|---|---|---|---|---|---|---|
| | | | | I-13 | I-14 | I-15 | I-16 |
| Constitutive Ingredients (part by mass) | Component (A) | C-HPC (I-2) | 0.5 | | | | |
| | | Cationized Guar Gum *1 | | 0.5 | | | |
| | | Cationized Hydroxyethyl Cellulose *2 | | | 0.5 | | |
| | | Hydroxypropyl Cellulose *3 | | | | 0.5 | |
| | | Dimethyldiallylammonium Chloride/Acrylamide Copolymer *4 | | | | | 0.5 |
| | Component (B) | High-Polymerization Dimethylsiloxane *5 | 1.0 | 1.0 | 1.0 | 1.0 | 1.0 |
| | Component (C) | Sodium Laureth-2 Sulfate | 7.5 | 7.5 | 7.5 | 7.5 | 7.5 |
| | | Cocoyl Fatty Acid Amide Propylbetaine | 4.5 | 4.5 | 4.5 | 4.5 | 4.5 |
| | | pH Regulator | | adequate dose | | | |
| | | Pure Water | | balance | | | |
| Evaluation Results (after dried) | | Finger combability | 5.0 | 3.0 | 2.4 | 2.0 | 3.0 |
| | | Oily feeling | 4.6 | 2.0 | 2.0 | 4.0 | 3.0 |
| | | Manageability | 5.0 | 2.0 | 2.0 | 3.0 | 3.0 |

*1: Sansho's trade name, JAGUAR C13S
*2: Nalco's trade name, MERQUAT 10
*3: Nippon Soda's trade name, CELNY M
*4: Nalco's trade name, MERQUAT 550
*5: Shin-etsu Chemical's trade name, KM-902 (effective ingredient 50%)

TABLE 13

| Hair Cosmetic (Shampoo) | | | Example | | | | | Comparative Example |
|---|---|---|---|---|---|---|---|---|
| | | | I-40 | I-41 | I-42 | I-43 | I-44 | I-17 |
| Constitutive Ingredients (part by mass) | Component (A) | C-HPC (I-2) | 0.01 | 0.1 | 0.3 | 1 | 3 | |
| | Component (B) | High-Polymerization Dimethylsiloxane *1 | 1 | 1 | 1 | 1 | 1 | 1 |
| | Component (C) | Sodium Laureth-2 Sulfate | 7.5 | 7.5 | 7.5 | 7.5 | 7.5 | 7.5 |
| | | Cocoyl Fatty Acid Amide Propylbetaine | 4.5 | 4.5 | 4.5 | 4.5 | 4.5 | 4.5 |
| | | pH Regulator | | | adequate dose | | | |
| | | Pure Water | | | balance | | | |
| Evaluation Results (after dried) | | Finger combability | 4.0 | 5.0 | 5.0 | 4.6 | 3.6 | 3.0 |
| | | Oily feeling | 3.6 | 4.6 | 4.6 | 4.6 | 4.6 | 2.0 |
| | | Manageability | 4.0 | 5.0 | 5.0 | 4.6 | 4.0 | 2.0 |

*1: Shin-etsu Chemical's trade name, KM-902 (effective ingredient 50%)

TABLE 14

| Hair Cosmetic (Shampoo) | | | Example | | | | | | | | | | Comparative Example |
|---|---|---|---|---|---|---|---|---|---|---|---|---|---|
| | | | I-45 | I-46 | I-47 | I-48 | I-49 | I-50 | I-51 | I-52 | I-53 | I-54 | I-18 |
| Constitutive Ingredients (part by mass) | Component (A) | C-HPC (I-2) | 0.5 | 0.5 | 0.5 | 0.5 | 0.5 | 0.5 | 0.5 | 0.5 | 0.5 | 0.5 | 0.5 |
| | Component (B) | Oleic Acid | 1 | | | | | | | | | | |
| | | Isostearic Acid | | 1 | | | | | | | | | |
| | | Macadamia Nut Oil *1 | | | 1 | | | | | | | | |

TABLE 14-continued

|  |  | Example | | | | | | | | | | Comparative Example |
|---|---|---|---|---|---|---|---|---|---|---|---|---|
| Hair Cosmetic (Shampoo) | | I-45 | I-46 | I-47 | I-48 | I-49 | I-50 | I-51 | I-52 | I-53 | I-54 | I-18 |
| | Liquid Paraffin *2 | | | | 1 | | | | | | | |
| | Avocado Oil *3 | | | | | 1 | | | | | | |
| | Dipentaerythrityl (Hydroxystearate/Stearate/Rosinate) *4 | | | | | | 1 | | | | | |
| | 2-Octyldodecanol | | | | | | | 1 | | | | |
| | Dimethiconol *5 | | | | | | | | 1 | | | |
| | Polyether-Modified Silicone *6 | | | | | | | | | 1 | | |
| | Polyether-Modified Silicone *7 | | | | | | | | | | 1 | |
| Component (C) | Sodium Laureth-2 Sulfate | 7.5 | 7.5 | 7.5 | 7.5 | 7.5 | 7.5 | 7.5 | 7.5 | 7.5 | 7.5 | 7.5 |
| | Cocoyl Fatty Acid Amide Propylbetaine | 4.5 | 4.5 | 4.5 | 4.5 | 4.5 | 4.5 | 4.5 | 4.5 | 4.5 | 4.5 | 4.5 |
| | pH Regulator | adequate dose | | | | | | | | | | |
| | Pure Water | balance | | | | | | | | | | |
| Evaluation Results (after dried) | Finger combability | 3.6 | 4.0 | 4.6 | 4.6 | 4.0 | 4.0 | 4.6 | 4.0 | 3.6 | 4.0 | 3.0 |
| | Oily feeling | 4.0 | 4.0 | 4.0 | 4.6 | 4.0 | 3.6 | 4.6 | 4.0 | 4.6 | 5.0 | 5.0 |
| | Manageability | 4.6 | 4.6 | 4.6 | 4.0 | 4.6 | 4.6 | 3.6 | 4.0 | 4.0 | 4.0 | 2.4 |

*1: Nikko Chemical's trade name, Macadamia Nut Oil
*2: Kaneda's trade name, HICALL K-230
*3: Nikko Chemical's trade name, Pure Avocado Oil
*4: Nisshin Oillio's trade name, COSMOL 168ARV
*5: Toray Dow Corning's trade name, 1785 EMULSION (effective ingredient 60%)
*6: Shin-etsu Chemical's trade name, KF6011
*7: Kao's trade name, SOFCARE GS-G

TABLE 15

|  |  |  | Example | | |
|---|---|---|---|---|---|
| Hair Cosmetic (Shampoo) | | | I-55 | I-56 | I-57 |
| Constitutive Ingredients (part by mass) | Component (A) | C-HPC (I-2) | 0.5 | 0.5 | 0.5 |
| | Component (B) | High-Polymerization Dimethylsiloxane *1 | 0.1 | 5 | 10 |
| | Component (C) | Sodium Laureth-2 Sulfate | 7.5 | 7.5 | 7.5 |
| | | Cocoyl Fatty Acid Amide Propylbetaine | 4.5 | 4.5 | 4.5 |
| | | pH Regulator | adequate dose | | |
| | | Pure Water | balance | | |
| Evaluation Results (after dried) | | Finger combability | 4.0 | 5.0 | 4.6 |
| | | Oily feeling | 3.6 | 4.6 | 4.4 |
| | | Manageability | 4.0 | 5.0 | 4.6 |

*1: Shin-etsu Chemical's trade name, KM-902 (effective ingredient 50%)

TABLE 16

|  |  | Example | | | | | | | | | | | | |
|---|---|---|---|---|---|---|---|---|---|---|---|---|---|
| Hair Cosmetic (Shampoo) | | I-58 | I-59 | I-60 | I-61 | I-62 | I-63 | I-64 | I-65 | I-66 | I-67 | I-68 | I-69 | I-70 |
| Constitutive Ingredients (part by mass) | Component (A) C-HPC (I-2) | 0.5 | 0.5 | 0.5 | 0.5 | 0.5 | 0.5 | 0.5 | 0.5 | 0.5 | 0.5 | 0.5 | 0.5 | 0.5 |
| | Component (C) Sodium Lauryl Sulfate | 10 | | | | | | | | | | | | |
| | Ammonium Laureth-1 Sulfate | | 10 | | | | | | | | | | | |
| | Sodium Laureth-2 Sulfate | | | 10 | | | | | | 10 | 10 | 10 | 10 | 10 |
| | Sodium Laureth-4,5 Acetate | | | | 10 | | | | | | | | | |
| | Sodium Laureth-2 Sulfosuccinate | | | | | 10 | | | | | | | | |
| | Sodium Cocoylglutamate *1 | | | | | | 10 | | | | | | | |
| | Cocoyl Fatty Acid Monoethanolamide | | | | | | | | | 2 | | | | |
| | Cocoyl Fatty Acid Methylethanolamide *2 | | | | | | | | | | 2 | | | |
| | Laurylcarboxymethyl-hydroxyimidazolium betaine *3 | | | | | | | 10 | | | | | | |
| | Laurylhydroxy-sulfobetaine *4 | | | | | | | | | | | | 2 | |
| | Laureth-3 | | | | | | | | | | | | | 2 |

TABLE 16-continued

| | Hair Cosmetic (Shampoo) | | I-58 | I-59 | I-60 | I-61 | I-62 | I-63 | I-64 | I-65 | I-66 | I-67 | I-68 | I-69 | I-70 |
|---|---|---|---|---|---|---|---|---|---|---|---|---|---|---|---|
| | | Ceteareth-16 | | | | | | | | | | | | | 2 |
| | | Alkylglucoside *5 | | | | | | | | 10 | | | | | |
| | Component (B) | High-Polymerization Dimethylsiloxane *6 | 1 | 1 | 1 | 1 | 1 | 1 | 1 | 1 | 1 | 1 | 1 | 1 | 1 |
| | | pH Regulator | | | | | | adequate dose balance | | | | | | | |
| | | Pure Water | | | | | | | | | | | | | |
| Evaluation Results (after dried) | | Finger combability | 4.6 | 5.0 | 5.0 | 5.0 | 4.2 | 4.0 | 4.8 | 5.0 | 5.0 | 5.0 | 5.0 | 5.0 | 5.0 |
| | | Oily feeling | 4.0 | 4.6 | 4.6 | 3.4 | 4.2 | 4.6 | 4.6 | 4.6 | 4.6 | 4.6 | 4.6 | 4.6 | 4.6 |
| | | Manageability | 4.0 | 4.6 | 4.6 | 4.2 | 4.0 | 4.0 | 4.0 | 3.6 | 4.2 | 5.0 | 5.0 | 4.6 | 4.6 |

*1: Ajinomoto's trade name, AMISOFT CS-11
*2: Kao's trade name, AMINON C11S
*3: Kao's trade name, AMPHITOL 20YB (effective ingredient 40%)
*4: Kao's trade name, AMPHITOL 20HD (effective ingredient 30%)
*5: Kao's trade name, MYDOL 10 (effective ingredient 40%)
*6: Shin-etu Chemical's trade name KM-902 (effective ingredient 50%)

From Tables 12 to 16, it is known that the shampoos of Examples I-39 to 70 are excellent shampoos satisfying all the requirements of good finger combability and good manageability with no oily feeling after drying.

Examples I-71 to 75

Production and Evaluation of Out-Bath Treatment

Using C—HPC (I-1) obtained in Production Example I-1, out-bath treatments of Examples I-71 to 75 each having the composition as in Table 17 were produced according to the same production method for the condition of Example I-1.

Hair tresses washed with the plain shampoo used in Example I-1 were fully wetted with warm water at 35 to 40° C., and drained, and thereafter the out-bath treatment was applied and spread thereover, and combed. Subsequently, the tresses were dried with warm air of a drier, and again combed for final dressing to give a sample of tresses for evaluation. Five panelists tested and evaluated the tresses for the finger combability, oily feeling and manageability thereof according to the evaluation criteria and the evaluation methods mentioned below. The results are shown in Table 17.

The finger combability, the oily feeling and the manageability of the sample of Comparative Examples I-19 was given a standard score 3; and the scores given by 5 panelists to each sample were averaged to give the mean score of each sample.

The samples having a mean score of 3.4 or more can be said to be obviously excellent in the evaluation test.

Comparative Examples I-19 to 26

Out-bath treatments each having the composition as in Table 17 were produced in the same manner as above, except that the cationized hydroxypropyl cellulose (A) was not added (Comparative Examples I-19 to 23), or a different polymer as in Table 17 was used in place of C—HPC (I-1) obtained in Production Example I-1 (Comparative Examples I-24 to 26). The results are shown in Table 17.

From Table 17, it is known that the out-bath treatments of Examples I-71 to 75 are excellent out-bath treatments satisfying all the requirements of good finger combability and good manageability with no oily feeling after drying.

TABLE 17

| | | | Example | | | | | Comparative Example | | | | | | | |
|---|---|---|---|---|---|---|---|---|---|---|---|---|---|---|---|
| Hair Cosmetic (Out-Bath Treatment) | | | I-71 | I-72 | I-73 | I-74 | I-75 | I-19 | I-20 | I-21 | I-22 | I-23 | I-24 | I-25 | I-26 |
| Constitutive Ingredients (part by mass) | Component (A) | C-HPC (I-1) | 0.03 | 0.05 | 0.05 | 0.05 | 0.05 | | | | | | | | |
| | | Cationized Hydroxycellulose *1 | | | | | | | | | | | 0.05 | | |
| | | Hydroxyethyl Cellulose *2 | | | | | | | | | | | | 0.05 | |
| | | Hydroxypropyl Cellulose *3 | | | | | | | | | | | | | 0.05 |
| | Component (B) | Stearyl Alcohol | 0.4 | 0.4 | 0.4 | 0.5 | 0.5 | 0.4 | 0.4 | 0.4 | 0.5 | 0.5 | 0.4 | 0.4 | 0.4 |
| | | Polyoxypropylene (Pop = 3) N-octyl Ether | 0.1 | | | | | 0.1 | | | | | | | |
| | | Myristyl Myristate | | 0.1 | | 0.1 | | | 0.1 | | 0.1 | | 0.1 | 0.1 | 0.1 |
| | | High-Polymerization Dimethylsiloxane *4 | | | 0.1 | | 0.1 | | | 0.1 | | 0.1 | | | |
| | Component (C) | Behenyltrimethyl-ammonium Chloride | 0.15 | 0.15 | 0.15 | | | 0.15 | 0.15 | 0.15 | | | 0.15 | 0.15 | 0.15 |
| | | Cetyltrimethyl-ammonium Chloride | | | | 0.12 | 0.12 | | | | 1.20 | 1.20 | | | |
| | | pH Regulator | | | | | | adequate dose balance | | | | | | | |
| | | Pure Water | | | | | | | | | | | | | |

TABLE 17-continued

| Hair Cosmetic (Out-Bath Treatment) | | Example | | | | | Comparative Example | | | | | | | |
|---|---|---|---|---|---|---|---|---|---|---|---|---|---|---|
| | | I-71 | I-72 | I-73 | I-74 | I-75 | I-19 | I-20 | I-21 | I-22 | I-23 | I-24 | I-25 | I-26 |
| Evaluation Results (after dried) | Finger combability | 5.0 | 5.0 | 5.0 | 5.0 | 5.0 | 3.0 | 3.0 | 3.6 | 3.0 | 3.6 | 2.6 | 2.0 | 2.0 |
| | Oily feeling | 5.0 | 5.0 | 4.2 | 4.6 | 5.0 | 3.0 | 2.0 | 2.0 | 2.0 | 2.0 | 2.0 | 3.0 | 3.0 |
| | Manageability | 5.0 | 5.0 | 5.0 | 5.0 | 5.0 | 3.0 | 4.0 | 3.0 | 3.0 | 3.0 | 3.0 | 3.0 | 3.0 |

*1: Nalco's trade name, MERQUAT 10
*2: Daicel's trade name, HEC-SE850K
*3: Nippon Soda's trade name, CELNY M
*4: Toray Dow Corning's trade name, BY22-060 (effective ingredient 60%)

Example I-76

Like in Example I-75, out-bath treatment having the composition mentioned below was produced.

| Component | (%) |
|---|---|
| C-HPC (I-1) | 0.5 |
| Stearyl alcohol | 4.0 |
| High-polymerization dimethylsiloxane*1 | 4.0 |
| Cetyltrimethylammonium chloride | 5.0 |
| pH regulator | moderate amount |
| Pure water | balance |
| Total | 100.0 |

*1Toray Dow Corning's trade name, BY22-060 (effective content 60%) was added in an amount of 6.7%.

Hair tresses washed with the plain shampoo used in Example I-1 were fully wetted with warm water at 35 to 40° C., drained, dried with hot air from a drier, and combed. 0.1 g of the out-bath treatment of Example I-75 was applied to the hair tips of 1 cm length of the hair tresses, and spread thereover. After dried at room temperature, the hair tresses were organoleptically evaluated.

The out-bath treatment gave good finger combability and manageability with no oily feeling after drying.

Production Example II-1

Production of C—HPC (II-1)

(1) Chipping Step

A sheet-like wood pulp (Tembec's Biofloc HV+, having a mean degree of polymerization of 1770, a degree of crystallinity of 74% and a water content of 7.0%) was pelletized with a sheet pelletizer (Horai's "SGG-220")) into chips of from 3 to 5 mm square.

(2) Cationization Step (1)

23.4 g of an aqueous solution of glycidyltrimethylammonium chloride (by Sakamoto Chemical Industry, water content 20%, purity 90% or more) (hereinafter referred to as "GMAC") (the amount corresponds to 0.2 mols per mol of AGU of cellulose) was added to 100 g of the chip-like pulp obtained in the above (1), and mixed in a mortar, and then put into a batch-type vibrational mill (Chuo Kakohki's "MB-1": chamber total volume 3.5 L; 13 rods of SUS304 each having a diameter of 30 mm and a length of 218 mm and having a circular cross section; filling rate 57%). This was ground for 30 minutes (frequency 20 Hz, vibrational amplitude 8 mm, temperature 30 to 70° C.) thereby giving a powdery mixture of cellulose and GMAC.

20 g (corresponding to 0.2 mols per mol of AGU) of an aqueous 24.7% sodium hydroxide solution was added to the obtained powdery mixture, mixed in a mortar and put into the above-mentioned batch-type vibrational mill. Under the same condition as above, this was ground for 60 minutes to give 151 g of a cationized cellulose (i).

(3) Cationization Step (2)

128 g of the cationized cellulose (i) obtained in the above (2) was mixed with 31.3 g of GMAC (corresponding to 0.32 mols per mol of AGU) in a mortar, and then the resulting mixture was put into a 1-L kneader equipped with a reflux tube (Irie Shokai's PNV-1 Model), and with stirring at 50° C. in a nitrogen atmosphere at 50 rpm, this was ripened for 5 hours to give a cationized cellulose (ii).

(4) Hydroxypropylation Step

The kneader containing 152.6 g of the cationized cellulose (ii) obtained after ripening (unneutralized unpurified product) was heated up to 70° C., and with stirring, 72.5 g propylene oxide (corresponding to 2.5 mols per mol of AGU, Kanto Chemical's special grade reagent) was dropwise added thereto and reacted for 20 hours until the propylene oxide was consumed and the reflux flow stopped.

After the reaction, the reaction mixture was taken out of the kneader to give 210.6 g of a pale brown crude C—HPC powder. 10.0 g of the crude C—HPC powder was sampled and neutralized with acetic acid. For the purpose of determining the degree of substitution with propyleneoxy group and with cationized ethyleneoxy group, the neutralized product was purified through a dialytic membrane (molecular weight cut off, 1000), and then the aqueous solution was freeze-dried to give a pure C—HPC (II-1).

Through elementary analysis thereof, the chlorine content of the obtained pure C—HPC (II-1) was 3.4%. The hydroxypropoxy group content according to the above-mentioned "Method for Analysis of Hydroxypropyl Cellulose" was 43.3%. The degree of substitution with cationized ethyleneoxy group and the degree of substitution with propyleneoxy group were 0.30 and 1.8, respectively. The mean degree of polymerization of the pure C—HPC (II-1) was 739. The results are shown in Table 18.

Production Example II-2

Production of C—HPC (II-2)

This is the same as in Production Example II-1 except that the condition of the cationization step (1) was changed as in Table 18, that the cationization step (2) was omitted, and that the condition of the hydroxypropylation step was changed as in Table 18. The results of the obtained pure C—HPC (II-2) are shown in Table 18.

Production Example II-3

Production of C—HPC (II-3)

This is the same as in Production Example II-1 except that the condition of the cationization step (1), that of the cationization step (2) and that of the hydroxypropylation step were changed as in Table 18. The results of the obtained pure C—HPC (II-3) are shown in Table 18.

Production Example II-4

Production of C—HPC (II-4)

This is the same as in Production Example II-1 except that the condition of the cationization step (1) was changed as in Table 18, that the cationization step (2) was omitted, and that the condition of the hydroxypropylation step was changed as in Table 18. The results of the obtained pure C—HPC (II-4) are shown in Table 18.

Production Example II-5

Production of C—HPC (II-5)

This is the same as in Production Example II-1 except that the condition of the cationization step (1), that of the cationization step (2) and that of the hydroxypropylation step were changed as in Table 18. The results of the obtained pure C—HPC (II-5) are shown in Table 18.

TABLE 18

| | Starting Pulp | | | | Cationization Step (1) | | | | | |
|---|---|---|---|---|---|---|---|---|---|---|
| | Degree of Crystallinity (%) | Mean Degree of Polymerization | Water Content (%) | Amount of Pulp Used (g) | Vibrational Mill | Amount of GMAC Added (g) | Grinding Time (min) | Amount of 24.7% NaOH Added (g) | Amount of 48% NaOH Added (g) | Grinding Time (min) |
| Production Example II-1 | 74 | 1770 | 7.0 | 100 | MB-1 | 23.4 | 30 | 20 | — | 60 |
| Production Example II-2 | 74 | 1770 | 7.0 | 100 | MB-1 | 60.8 | 12 | — | 14.8 | 120 |
| Production Example II-3 | 74 | 1770 | 7.0 | 100 | MB-1 | 23.4 | 12 | — | 6.2 | 60 |
| Production Example II-4 | 74 | 1770 | 7.0 | 100 | MB-1 | 109 | 12 | — | 47.9 | 120 |
| Production Example II-5 | 74 | 1770 | 7.0 | 86 | MB-1 | 20 | 12 | — | 8.8 | 60 |

| | Cationization Step (2) | | | | Hydroxypropylation Step | | | Physical Properties of C-HPC | | |
|---|---|---|---|---|---|---|---|---|---|---|
| | Amount of Cationized Cellulose (i) Used (g) | Amount of GMAC Added (g) | Ripening Temperature (° C.) | Ripening Time (hr) | Amount of Cationized Cellulose (ii) Used (g) | Amount of Propylene Oxide Added (g) | Reaction Time (hr) | Mean Degree of Polymerization | Chlorine Content (%) | Content of Hydroxypropoxy Group (%) |
| Production Example II-1 | 128 | 31.3 | 50 | 5 | 152.6 | 72.5 | 20 | 739 | 3.4 | 43.3 |
| Production Example II-2 | — | — | — | — | 100 *1 | 40.8 | 8 | 539 | 3.0 | 32.5 |
| Production Example II-3 | 175 | — | 50 | 5 | 100 | 150 | 18 | 1230 | 1.1 | 62.7 |
| Production Example II-4 | — | — | — | — | 220 *1 | 153 | 5 | 964 | 3.3 | 54.4 |
| Production Example II-5 | 110 | 132 | 50 | 5 | 140 | 20 | 9 | 1326 | 9.3 | 5.2 |

*1: Cationized cellulose (ii) was used in place of cationized cellulose (i).

Production Example II-6

Production of C—HPC (II-6)

(1) Chipping Step

As cellulose, a sheet-like wood pulp (Tembec's Biofloc HV10, having a mean degree of polymerization of 1508, a degree of crystallinity of 74% and a water content of 7.0%) was pelletized with a sheet pelletizer (Horai's "SGG-220") into chips of from 3 to 5 mm square.

(2) Cationization Step (1)

559 g of GMAC (corresponding to 0.52 mols per mol of AGU) and 24 g of ion-exchanged water were added to 989 g (water content 7.0%) of the chip-like pulp obtained in the above (1), and mixed in a plastic bag, and then put into a batch-type vibrational mill (Chuo Kakohki's "FV-10": chamber total volume 35 L; 63 rods of SUS304 each having a diameter of 30 mm and a length of 510 mm and having a circular cross section; filling rate 64%). This was ground for 12 minutes (frequency 20 Hz, vibrational amplitude 8 mm, temperature 10 to 40° C.) thereby giving a powdery mixture of cellulose and GMAC.

136.2 g (corresponding to 0.60 mols per mol of AGU) of granular sodium hydroxide (effective content 100%) was put into the vibrational mill. Again this was ground for 112 minutes to give a cationized cellulose.

(3) Hydroxypropylation Step 95.0 g of the cationized cellulose obtained in the above (2) was put into the kneader equipped with a reflux tube used in Production Example II-1, the kneader was heated up to 70° C., and with stirring, 35.4 g (corresponding to 2.0 mols per mol of AGU) of propylene oxide was dropwise added thereto, and the reaction was continued for 7 hours until the propylene oxide was consumed and the reflux flow stopped. After the reaction, the reaction mixture was taken out of the kneader to give 120.6 g of a pale brown crude C—HPC powder.

(4) Cationization Step (2)

16.2 g (corresponding to 3.5 mols per mol of AGU) of GMAC was added to 10.6 g of the crude C—HPC powder obtained in the above (3), mixed in a mortar, and then ripened in a thermostat chamber at 50° C. for 24 hours. The obtained crude C—HPC was dispersed in 100 g of a mixed solvent of water/ethanol/isopropyl alcohol=5/45/50 (by weight), then neutralized with acetic acid added thereto, and purified through precipitation. The precipitate was collected through filtration, and dried under reduced pressure overnight in a drier at 60° C. thereby giving a pale brown bulky crude C—HPC (II-6).

For the purpose of determining the degree of substitution with propyleneoxy group and with cationized ethyleneoxy group, the product was purified through a dialytic membrane (molecular weight cut off, 1000), and then the aqueous solution was freeze-dried to give a pure C—HPC (II-6).

Through elementary analysis thereof, the chlorine content of the obtained pure C—HPC (II-6) was 9.1%. The hydroxypropoxy group content was 25.1%. The degree of substitution with cationized ethyleneoxy group and the degree of substitution with propyleneoxy group were calculated to be 1.00 and 1.3, respectively. The mean degree of polymerization of the pure C—HPC (II-6) was 464. The results are shown in Table 19.

Production Example II-7

Production of C—HPC (II-7)

This is the same as in Production Example II-6 except that the starting pulp was changed as in Table 19, and that the conditions of the cationization step (1), the hydroxypropylation step and the cationization step (2) were changed as in Table 19. The results of the obtained pure C—HPC (II-7) are shown in Table 19.

TABLE 19

| | Starting Pulp | | | | Cationization Step (1) | | | | | |
|---|---|---|---|---|---|---|---|---|---|---|
| | Degree of Crystallinity (%) | Mean Degree of Polymerization | Water Content (%) | Amount of Pulp Used (g) | Vibrational Mill | Amount of GMAC Added (g) | Grinding Time (min) | Amount of 48% NaOH Added (g) | Amount of Granular NaOH Added (g) | Grinding Time (min) |
| Production Example II-6 | 74 | 1508 | 7.0 | 989 | FV-10 | 559 | 12 | — | 136.2 | 112 |
| Production Example II-7 | 77 | 191 | 7.0 | 100 | MB-1 | 60.8 | 12 | 29.8 | — | 140 |

| | Hydroxypropylation Step | | | Cationization Step (2) | | | | Physical Properties of C-HPC | | |
|---|---|---|---|---|---|---|---|---|---|---|
| | Amount of Cationized Cellulose Used (g) | Amount of Propylene Oxide Added (g) | Reaction Time (hr) | Amount of Crude C-HPC Powder Used (g) | Amount of GMAC Added (g) | Ripening Temperature (° C.) | Ripening Time (hr) | Mean Degree of Polymerization | Chlorine Content (%) | Content of Hydroxypropoxy Group (%) |
| Production Example II-6 | 95 | 35.4 | 7 | 10.6 | 16.2 | 50 | 24 | 464 | 9.1 | 25.1 |
| Production Example II-7 | 190 | 18 | 2 | 45 | 152 | 50 | 24 | 214 | 15.7 | 3.3 |

Production Example II-8

Production of C—HPC (II-8)

(1) Low-Crystalline Powdery Cellulose Production Step

A sheet-like wood pulp (Tembec's Biofloc HV+, having a mean degree of polymerization of 1770, a degree of crystallinity of 74% and a water content of 7.0%) was shredded with a shredder (Meiko Shokai's "MSX2000-IVP440F") into chips of from 3 to 5 mm square. Subsequently, this was dried under reduced pressure at 50° C. for 12 hours to give a chip-like dry pulp (water content 0.4%).

Next, 100 g of the obtained chip-like dry pulp was put into the batch-type vibrational mill used in Production Example II-1. This was ground for 35 minutes at a frequency 20 Hz, a vibrational amplitude of 8 mm, and a temperature falling within a range of from 30 to 70° C. to give a powdery cellulose (having a degree of crystallinity of 0%, a mean degree of polymerization of 836, a mean particle size of 52 μm and a water content of 1.0%).

(2) Cationization Step 46.9 g (corresponding to 0.4 mols per mol of AGU) of GMAC was added to 100 g of the powdery cellulose obtained in the above (1), and mixed in a mortar. Subsequently, 5.14 g (corresponding to 0.1 mols per mol of AGU) of an aqueous 48% sodium hydroxide solution and 18 g of ion-exchanged water were added thereto and mixed. The resulting mixture was put into the kneader used in Production Example II-1, and stirred at 50° C. for 4 hours to give 170 g of a cationized cellulose.

(3) Hydroxypropylation Step 170 g of the cationized cellulose obtained in the above (2) was heated at 70° C., and with stirring, 4.7 g (corresponding to 0.1 mols per mol of AGU) of an aqueous 48% sodium hydroxide solution and 16.4 g of ion-exchanged water were added thereto. Further, 101 g (corresponding to 3.0 mols per mol of AGU) of propylene oxide was dropwise added thereto and reacted for 24 hours until the propylene oxide was consumed and the reflux flow stopped. After the reaction, the cellulose kept a flowable powdery state. 10.0 g of the reaction product was sampled and neutralized with acetic acid to give a pale brown solid. The neutralized product was purified through a dialytic membrane (molecular weight cut off, 1000), and then the aqueous solution was freeze-dried to give a pure C—HPC (II-8).

Through elementary analysis thereof, the chlorine content of the obtained pure C—HPC (II-8) was 2.1%. The hydroxypropoxy group content was 49.2%. The degree of substitution with cationized ethyleneoxy group and the degree of substitution with propyleneoxy group were calculated to be 0.18 and 2.0, respectively. The mean degree of polymerization of the pure C—HPC (II-8) was 832. The results are shown in Table 20.

Production Example II-9

Production of C—HPC (II-9)

This is the same as in Production Example II-8 except that the starting pulp was changed as in Table 20, and that the conditions of the low-crystalline powdery cellulose production step, the cationization step and the hydroxypropylation step were changed as in Table 20. The results of the obtained pure C—HPC (II-9) are shown in Table 20.

Production Example II-10

Production of C—HPC (II-10)

This is the same as in Production Example II-8 except that the condition of the hydroxypropylation step was changed as in Table 20. The results of the obtained pure C—HPC (II-10) are shown in Table 20.

TABLE 20

| | Starting Pulp | | | | Chip-like Dry Pulp Water Content (%) | Grinding Step Grinding Time (min) | Physical Properties of Powdery Cellulose | | | |
|---|---|---|---|---|---|---|---|---|---|---|
| | Degree of Crystallinity (%) | Mean Degree of Polymerization | Water Content (%) | Shredding Step Drying Step | | | Degree of Crystallinity (%) | Mean Degree of Polymerization | Mean Particle Size (μm) | Water Content (%) |
| Production Example II-8 | 74 | 1770 | 7.0 | at 50° C. under reduced pressure, for 12 hours | 0.4 | 35 | 0 | 836 | 52 | 1.0 |
| Production Example II-9 | 74 | 1420 | 7.0 | at 50° C. under reduced pressure, for 12 hours | 0.4 | 20 | 0 | 574 | 52 | 1.0 |
| Production Example II-10 | 74 | 1770 | 7.0 | at 50° C. under reduced pressure, for 12 hours | 0.4 | 35 | 0 | 836 | 52 | 1.0 |

| | Cationization Step | | | Hydroxypropylation Step | | Physical Properties of C-HPC | | |
|---|---|---|---|---|---|---|---|---|
| | Amount of Powdery Cellulose Used (g) | Amount of 48% NaOH Added (g) | Amount of GMAC Added (g) | Amount of 48% NaOH Added (g) | Amount of Propylene Oxide Added (g) | Mean Degree of Polymerization | Chlorine Content (%) | Content of Hydroxypropoxy Group (%) |
| Production Example II-8 | 100 | 5.1 | 46.9 | 4.7 | 101 | 832 | 2.1 | 49.2 |
| Production Example II-9 | 100 | 10.2 | 33.6 | — | 53.2 | 646 | 2.3 | 37.1 |

TABLE 20-continued

| | | | | | | | | |
|---|---|---|---|---|---|---|---|---|
| Production Example II-10 | 100 | 5.1 | 46.9 | 4.7 | 89 | 779 | 2.2 | 45.7 |

Production Example II-11

Production of Cationized Cellulose (II-1)

A cationized cellulose (II-1) was produced in the same manner as in Production Example II-5 except that the propylene oxide addition was omitted.

Production Example II-12

Production of C—HPC (II-11)

(1) Chipping Step

A sheet-like wood pulp (Tembec's Biofloc HV+, having a mean degree of polymerization of 1481, a degree of crystallinity of 74% and a water content of 4.6%) was pelletized with a sheet pelletizer (Horai's "SGG-220") into chips of from 3 to 5 mm square.

(2) Alkali Cellulose Production Step 100 g of the chip-like pulp obtained in the above step (1) and 23.6 g of 0.7-mm granular NaOH (corresponding to 1.0 mol per mol of AGU) were put into a batch-type vibrational mill (Chuo Kakohki's "MB-1": chamber total volume 3.5 L; 13 rods of SUS304 each having a diameter of 30 mm and a length of 218 mm and having a circular cross section; filling rate 57%), and ground therein for 15 minutes (frequency 20 Hz, vibrational amplitude 8 mm, temperature 30 to 70° C.). Thus obtained, the ground cellulose/NaOH mixture (mean particle size of cellulose: 65 µm) was transferred into a mortar, and Sprayed with 50 g of water. The water content of the ground cellulose/NaOH mixture was 57% relative to the cellulose therein. This was ground with a pestle at 20° C. for 5 minutes to give an alkali cellulose (mean degree of polymerization: 1175).

(3) Hydroxypropylation Step

The alkali cellulose obtained in the above step (2) was put into a kneader equipped with a reflux tube and a dropping funnel (Irie Shokai's PNV-1 Model, capacity 1.0 L), and 85.7 g of propylene oxide (corresponding to 2.5 mols per mol of AGU) was put thereinto and reacted at 50° C. for 6 hours with stirring. For the reaction, propylene oxide was dropwise added taking 5 hours, and the system was then ripened for 1 hour.

(4) Cationization Step 5.8 g of the reaction mixture obtained in the above step (3) was taken into a mortar, and 2.10 g of aqueous 65% 3-chloro-2-hydroxypropyltrimethylammonium chloride solution (by Yokkaichi Gosei) (corresponding to 0.50 mols per mol of AGU) was added thereto and mixed for 5 minutes, and thereafter this was transferred into a 50-ml glass bottle and reacted therein at 50° C. for 7 hours to give a crude C—HPC.

5.0 g of the crude C—HPC powder was sampled and neutralized with lactic acid. For the purpose of determining the degree of substitution with propyleneoxy group and with cationized ethyleneoxy group, the neutralized product was purified through a dialytic membrane (molecular weight cut off, 1000), and then the aqueous solution was freeze-dried to give a pure C—HPC (II-11).

Through elementary analysis thereof, the chlorine content of the obtained pure C—HPC (II-11) was 3.3%, and the hydroxypropoxy group content was 38.8%. The degree of substitution with cationized ethyleneoxy group and the degree of substitution with propyleneoxy group were calculated to be 0.27 and 1.5, respectively. The mean degree of polymerization was 643. The results are shown in Table 21.

TABLE 21

| | Starting Pulp | | | | Alkali Cellulose Production Step | | | | Physical Properties of Alkali Cellulose | |
|---|---|---|---|---|---|---|---|---|---|---|
| | Degree of Crystallinity (%) | Mean Degree of Polymerization | Water Content (%) | Vibration Mill | Amount of Pulp Used (g) | Grinding Time (min) | Amount of Granular NaOH Used (g) | Amount of Water Added (g) | Mean Particle Size (µm) | Mean Degree of Polymerization |
| Production Example II-12 | 74 | 1481 | 4.6 | MB-1 | 100 | 15 | 23.6 | 50 | 65 | 1175 |

| | Hydroxypropylation Step | | | Cationization Step | | | | Physical Properties of C-HPC | | |
|---|---|---|---|---|---|---|---|---|---|---|
| | Amount of Propylene Oxide added (g) | Reaction Temperature (° C.) | Reaction Time (hr) | Amount of Reaction Mixture Used (g) | Amount of Aqueous Ammonium Chloride Solution Used (g)*1 | Reaction Temperature (° C.) | Reaction Time (hr) | Mean Degree of Polymerization | Chlorine Content (%) | Content of Hydroxypropoxy Group (%) |
| Production Example II-12 | 85.7 | 50 | 6 | 5.8 | 2.10 | 50 | 7 | 643 | 3.3 | 38.8 |

*1Amount of aqueous 3-chloro-2-hydroxypropyltrimethylammonium chloride solution used (g).

Production Example II-13

Production of C—HPC (II-12)

(1) Low-Crystalline Powdery Cellulose Production Step

A chip-like pulp of from 3 to 5 mm square was obtained in the same manner as in Production Example II-12(1). One kg of the obtained chip-like pulp was put into a drier (Advantec Toyo's trade name, VO-402) and dried therein at 105° C. for 2 hours to give a dry chip-like pulp (water content 0.8%).

920 g of the obtained dry chip-like pulp was put into a batch-type vibrational mill (Chuo Kakohki's "FV-10": chamber total volume 35 L; 63 rods of SUS304 each having a diameter of 30 mm and a length of 510 mm and having a circular cross section; filling rate 65%). This was ground for 10 minutes (frequency 20 Hz, vibrational amplitude 8 mm, temperature 10 to 40° C.) to give a powdery cellulose (having a degree of crystallinity of 14%, a mean degree of polymerization of 1198, and a water content of 1.0%).

(2) Alkali Cellulose Production Step 369 g of the powdery cellulose obtained in the above step (1) was put into a mixer (Matsubo's "Ledige Mixer", capacity 5 L), and with stirring at 250 rpm for the main blade and at 2500 rpm for the chopper blade, this was sprayed with 212 g of an aqueous 42.5% sodium hydroxide solution (corresponding to 1.0 mol of NaOH per mol of AGU, and 33% of water relative to cellulose) taking 1.5 minutes. After the spraying, the inner temperature was elevated up to 50° C., and the system was ripened for 3 hours to give an alkali cellulose.

(3) Hydroxypropylation Step 607 g of the alkali cellulose obtained in the above step (2) was heated up to 50° C. in the Ledige mixer with stirring at 50 rpm for the main blade and at 400 rpm for the chopper blade, and thereafter 187 g of propylene oxide (corresponding to 1.6 mols per mol of AGU) was dropwise added thereto taking 3.5 hours. After the addition, this was ripened at 50° C. for 2 hours.

(4) Cationization Step 11.4 g of the reaction mixture obtained in the above step (3) was taken into a mortar, and 4.31 g of an aqueous 65% 3-chloro-2-hydroxypropyltrimethylammonium chloride solution (corresponding to 0.5 mols per mol of AGU) and 0.84 g of ion-exchanged water were added thereto and mixed for 5 minutes, and thereafter this was transferred into a 50-ml glass bottle and reacted therein at 50° C. for 5 hours to give a crude C—HPC. The crude C—HPC powder was neutralized, purified and freeze-dried in the same manner as in Production Example II-12(4) to give a pure C—HPC (II-12).

Through elementary analysis thereof, the chlorine content of the obtained pure C—HPC (II-12) was 4.3%. The hydroxypropoxy group content was 24.3%. The degree of substitution with cationized ethyleneoxy group and the degree of substitution with propyleneoxy group were calculated to be 0.25 and 0.8, respectively. The mean degree of polymerization was 659. The results are shown in Table 22.

Production Example II-14

Production of C—HPC (II-13)

(1) Low-Crystalline Powdery Cellulose Production Step

A powdery cellulose (having a degree of crystallinity of 14%, a mean degree of polymerization of 1198 and a water content of 1.0%) was obtained in the same manner as in Production Example II-13(1).

(2) Alkali Cellulose Production Step

An alkali cellulose was obtained in the same manner as in Production Example II-13(2), except that 530.5 g of the powdery cellulose obtained in the above step (1) and 307 g of an aqueous 42.5% sodium hydroxide solution (corresponding to 1.0 mol of NaOH per mol of AGU and 34% of water relative to cellulose) were used.

(3) Hydroxypropylation Step 825 g of the alkali cellulose obtained in the above step (2) was heated up to 50° C. with stirring in the above-mentioned Ledige mixer at 50 rpm for the main blade and at 400 rpm for the chopper blade, and thereafter 467 g of propylene oxide (corresponding to 2.6 mols per mol of AGU) was dropwise added thereto taking 6 hours. After the addition, this was ripened at 50° C. for 2 hours.

(4) Cationization Step 12.3 g of the reaction mixture obtained in the above step (3) was taken into a mortar, and 4.31 g of an aqueous 65% 3-chloro-2-hydroxypropyltrimethylammonium chloride solution (corresponding to 0.5 mols per mol of AGU) and 0.84 g of ion-exchanged water were added thereto and mixed for 5 minutes, and thereafter this was transferred into a 50-ml glass bottle and reacted therein at 50° C. for 5 hours to give a crude C—HPC. The crude C—HPC powder was neutralized, purified and freeze-dried in the same manner as in Production Example II-13 (4) to give a pure C—HPC (II-13).

Through elementary analysis thereof, the chlorine content of the obtained pure C—HPC (II-13) was 2.5%. The hydroxypropoxy group content was 38.5%. The degree of substitution with cationized ethyleneoxy group and the degree of substitution with propyleneoxy group were calculated to be 0.19 and 1.4, respectively. The mean degree of polymerization was 1186. The results are shown in Table 22.

TABLE 22

| | Starting Pulp | | | Low-Crystalline Powdery Cellulose Production Step | | | | Physical Properties of Powdery Cellulose | | |
|---|---|---|---|---|---|---|---|---|---|---|
| | Degree of Crystallinity (%) | Mean Degree of Polymerization | Water Content (%) | Vibrational Mill | Drying Time (hr) | Drying Temperature (° C.) | Grinding Time (min) | Degree of Crystallinity (%) | Mean Degree of Polymerization | Water Content (%) |
| Production Example II-13 | 74 | 1481 | 4.6 | FV-10 | 2 | 105 | 10 | 14 | 1198 | 1 |
| Production Example II-14 | 74 | 1481 | 4.6 | FV-10 | 2 | 105 | 10 | 14 | 1198 | 1 |

TABLE 22-continued

|  | Alkali Cellulose Production Step | | | | Hydroxypropylation Step | | | |
|---|---|---|---|---|---|---|---|---|
|  | Amount of Powdery Cellulose Used (g) | Amount of Aqueous 42.5% NaOH Solution Used (g) | Ripening Temperature (° C.) | Ripening Time (min) | Amount of Alkali Cellulose Used (g) | Amount of Propylene Oxide Used (g) | Reaction Temperature (° C.) | Reaction Time (hr) |
| Production Example II-13 | 369 | 212 | 50 | 3 | 607 | 187 | 50 | 5.5 |
| Production Example II-14 | 530.5 | 307 | 50 | 3 | 825 | 467 | 50 | 8 |

|  | | Cationization Step | | | | Physical Properties of C-HPC | | |
|---|---|---|---|---|---|---|---|---|
|  | | Amount of Reaction Mixture Used (g) | Amount of Aqueous Ammonium Chloride Solution Used (g) *1 | Reaction Temperature (° C.) | Reaction Time (hr) | Mean Degree of Polymerization | Chlorine Content (%) | Content of Hydroxypropoxy Group (%) |
|  | Production Example II-13 | 11.4 | 4.31 | 50 | 5 | 659 | 4.3 | 24.3 |
|  | Production Example II-14 | 12.3 | 4.31 | 50 | 5 | 1186 | 2.5 | 38.5 |

*1: Amount of aqueous 3-chloro-2-hydroxypropyltrimethylammonium chloride solution used (g).

The mean degree of polymerization, the degree of substitution with cationized ethyleneoxy group and the degree of substitution with propyleneoxy group of C—HPC obtained in Production Examples II-1 to 10, and 12 to 14, and the mean degree of polymerization and the degree of substitution with cationized ethyleneoxy group of the cationized cellulose (II-1) are summarized in Table 23.

TABLE 23

|  |  | Mean Degree of Polymerization | Degree of Substitution with Cationized EO *1 | Degree of Substitution with PO *2 | 2% Viscosity *3 |
|---|---|---|---|---|---|
| Production Example II-1 | C-HPC (1) | 739 | 0.30 | 1.8 | — |
| Production Example II-2 | C-HPC (2) | 539 | 0.22 | 1.1 | 171 |
| Production Example II-3 | C-HPC (3) | 1230 | 0.11 | 2.9 | — |
| Production Example II-4 | C-HPC (4) | 964 | 0.35 | 2.7 | 23 |
| Production Example II-5 | C-HPC (5) | 1326 | 0.75 | 0.2 | 13600 |
| Production Example II-6 | C-HPC (6) | 464 | 1.00 | 1.3 | 32 |
| Production Example II-7 | C-HPC (7) | 214 | 2.36 | 0.2 | 9 |
| Production Example II-8 | C-HPC (8) | 832 | 0.18 | 2.0 | — |
| Production Example II-9 | C-HPC (9) | 646 | 0.17 | 1.3 | — |
| Production Example II-10 | C-HPC (10) | 779 | 0.18 | 1.8 | — |
| Production Example II-11 | Cationized Cellulose (1) | 1288 | 0.77 | 0.0 | 1049 |
| Production Example II-12 | C-HPC (11) | 643 | 0.27 | 1.5 | — |
| Production Example II-13 | C-HPC (12) | 659 | 0.25 | 0.8 | — |
| Production Example II-14 | C-HPC (13) | 1186 | 0.19 | 1.4 | — |

*1: Degree of substitution with cationized ethyleneoxy group.
*2: Degree of substitution with propyleneoxy group.
*3: Viscosity of 2% C-HPC (mPa · s)

Examples II-1 to 23, and 50 to 52

Production and Evaluation of Conditioner

Any of C—HPC (II-1) to (II-13) was used as the component (A), and conditioners each having the composition shown in Tables 24 to 27 were produced according to an ordinary method.

Concretely, the component (A) was dissolved or uniformly dispersed in water to prepare an aqueous 2% polymer solution. A moderate amount of water and the surfactant (C) were taken in a beaker, heated at 80° C. and mixed to prepare an aqueous solution, and this was added to the above-mentioned, aqueous polymer solution and uniformly mixed. After melted, the oil (B), cetyl alcohol and stearyl alcohol were added thereto, stirred and emulsified for 30 minutes, and cooled. Finally, water that had evaporated away by heating was replenished and the pH of the mixture was measured. The pH was controlled to be 5 with a pH regulator (aqueous 50% citric acid solution).

Examples II-24 to 26

The component (A) was dissolved or uniformly dispersed in water to prepare an aqueous 2% polymer solution. A moderate amount of water, the surfactant (C) and an equimolar amount of a pH regulator (aqueous 50% citric acid solution) were added thereto and heated up to 80° C. After melted, the oil (B), cetyl alcohol, stearyl alcohol and the surfactant (C) were added thereto, stirred and emulsified for 30 minutes, and cooled. Finally, water that had evaporated away by heating was replenished and the pH of the mixture was measured. The pH was controlled to be 5 with a pH regulator (aqueous 50% citric acid solution).

Hair tresses were washed with plain shampoo mentioned below, fully wetted with warm water at 35 to 40° C., and thereafter 1 g of the conditioner of Examples II-1 to 26, and 50 to 52 was applied thereto and spread evenly thereover. Subsequently, the hair tresses were rinsed with warm water for 30 seconds, wiped with a towel to remove water, combed, and dried with warm air from a drier, and again combed for final dressing to give a sample of tresses for evaluation.

Five panelists tested and evaluated the tresses for the finger combability, oily feeling and manageability thereof according to the following evaluation criteria and evaluation methods. The results are shown in Tables 24 to 27.

(Composition of Plain Shampoo)

| Component | (%) |
|---|---|
| Na polyoxyethylene lauryl ether sulfate (42.0% as EMAL E-27C (by Kao, effective content, 27% by weight)) | 11.3 |
| Cocoyl fatty acid N-methylethanolamide (AMINONE C-11S (by Kao) | 3.0 |
| Citric acid | 0.2 |
| Methylparaben | 0.3 |
| Pure water | balance |
| Total | 100.0 |

(Production of Plain Shampoo)

The components were taken in a beaker, heated at 80° C. and mixed, and after their uniform dissolution was confirmed, the mixture was cooled to give plain shampoo.

(Evaluation Criteria, Evaluation Methods)

Finger Combability
- 5: Excellent finger combability.
- 4: Good finger combability.
- 3: Average.
- 2: Bad finger combability.
- 1: Extremely bad finger combability.

Oily Feeling
- 5: Not oily.
- 4: Not so much oily.
- 3: Average.
- 2: Somewhat oily.
- 1: Oily.

Manageability
- 5: The hair was very well manageable.
- 4: The hair was well manageable.
- 3: Average.
- 2: The hair was poorly manageable.
- 1: The hair was not manageable at all.

The finger combability, the oily feeling and the manageability of the sample of Comparative Examples II-6 was given a standard score 3; and the scores given by 5 panelists to each sample were averaged to give the mean score of each sample.

Comparative Examples II-1 to 8

Conditioners each having the composition as in Table 24 were produced in the same manner as in Example II-1, except that the component (A) in Example II-1 was not added (Comparative Examples II-1), or a different polymer as in Table 24 was used in place of the component (A) (Comparative Examples II-2 to 8). The pH of the conditioners of Comparative Examples II-1 to 8 was controlled to be 5 with a pH regulator (aqueous 50% citric acid solution) added thereto. The conditioners of Comparative Examples II-1 to 8 were tested and evaluated in the same manner as in Examples II-1 to 26. The results are shown in Table 24.

TABLE 24

| | Hair Cosmetic (Conditioner) | | Example | | | | | | | | | | | | | Comparative Example | | | | | | | |
|---|---|---|---|---|---|---|---|---|---|---|---|---|---|---|---|---|---|---|---|---|---|---|---|
| | | | II-1 | II-2 | II-3 | II-4 | II-5 | II-6 | II-7 | II-8 | II-9 | II-10 | II-50 | II-51 | II-52 | II-1 | II-2 | II-3 | II-4 | II-5 | II-6 | II-7 | II-8 |
| Constitutive Components (part by mass) | Component (A) | C-HPC (II-1) | 0.5 | | | | | | | | | | | | | | | | | | | | |
| | | C-HPC (II-2) | | 0.5 | | | | | | | | | | | | | | | | | | | |
| | | C-HPC (II-3) | | | 0.5 | | | | | | | | | | | | | | | | | | | |
| | | C-HPC (II-4) | | | | 0.5 | | | | | | | | | | | | | | | | | | |
| | | C-HPC (II-5) | | | | | 0.5 | | | | | | | | | | | | | | | | | |
| | | C-HPC (II-6) | | | | | | 0.5 | | | | | | | | | | | | | | | | |
| | | C-HPC (II-7) | | | | | | | 0.5 | | | | | | | | | | | | | | | |
| | | C-HPC (II-8) | | | | | | | | 0.5 | | | | | | | | | | | | | | |
| | | C-HPC (II-9) | | | | | | | | | 0.5 | | | | | | | | | | | | | |
| | | C-HPC (II-10) | | | | | | | | | | 0.5 | | | | | | | | | | | | |
| | | C-HPC (II-11) | | | | | | | | | | | 0.5 | | | | | | | | | | | |
| | | C-HPC (II-12) | | | | | | | | | | | | 0.5 | | | | | | | | | | |
| | | C-HPC (II-13) | | | | | | | | | | | | | 0.5 | | | | | | | | | |
| | | Cationized Cellulose (II-1) | | | | | | | | | | | | | | | 0.5 | | | | | | |
| | | Cationized Hydroxyethyl Cellulose *1 | | | | | | | | | | | | | | | | 0.5 | | | | | |
| | | Cationized Guar Gum *2 | | | | | | | | | | | | | | | | | 0.5 | | | | |
| | | Hydroxyethyl Cellulose *3 | | | | | | | | | | | | | | | | | | 0.5 | | | |
| | | Hydroxypropyl Cellulose *4 | | | | | | | | | | | | | | | | | | | 0.5 | | |
| | | Dimethyldiallylammonium Chloride/Acrylamide Copolymer *5 | | | | | | | | | | | | | | | | | | | | 0.5 | |
| | | Dimethyldiallylammonium Chloride/Vinylpyrrolidone/Vinylimidazole Copolymer *6 | | | | | | | | | | | | | | | | | | | | | 0.5 |
| | Component (B) | Dioctyl Ether *7 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| | | Cetyl Alcohol | 1.3 | 1.3 | 1.3 | 1.3 | 1.3 | 1.3 | 1.3 | 1.3 | 1.3 | 1.3 | 1.3 | 1.3 | 1.3 | 1.3 | 1.3 | 1.3 | 1.3 | 1.3 | 1.3 | 1.3 | 1.3 |
| | | Stearyl Alcohol | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 |
| | Component (C) | Behenyltrimethylammonium Chloride | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 |
| | | pH Regulator | adequate dose | | | | | | | | | | | | | | | | | | | | |
| | | Pure Water | balance | | | | | | | | | | | | | | | | | | | | |
| Evaluation Results (after dried) | | Finger combability | 5.0 | 5.0 | 3.8 | 5.0 | 4.6 | 5.0 | 4.0 | 3.4 | 3.8 | 3.4 | 5 | 4.6 | 5 | 2.4 | 1.8 | 2.2 | 2.0 | 2.4 | 3.0 | 3.0 | 3.6 |
| | | Oily feeling | 4.6 | 4.6 | 4.6 | 4.6 | 4.4 | 4.6 | 3.4 | 3.4 | 3.8 | 3.4 | 4.6 | 4.2 | 4.6 | 1.8 | 3.4 | 3.6 | 3.0 | 2.0 | 3.0 | 2.6 | 2.6 |
| | | Manageability | 4.6 | 4.6 | 3.8 | 4.6 | 4.4 | 4.6 | 4.0 | 3.6 | 3.4 | 3.6 | 4.6 | 4.6 | 4.6 | 1.8 | 2.2 | 2.8 | 2.6 | 2.0 | 2.0 | 1.5 | 1.5 |

*1: Nalco's MERQUAT 10
*2: Sansho's JAGUAR C13S
*3: Daicel's HEC-SE850K
*4: Nippon Soda's CELNY M
*5: Nalco's MERQUAT 550
*6: BASF's LUVIQUAT SENSATION
*7: Cognis' trade name, CETIOL OE
*8: To make 100 parts by mass in total.

TABLE 25

| Hair Cosmetic (Conditioner) | | | Example | | | | | | |
|---|---|---|---|---|---|---|---|---|---|
| | | | II-11 | II-12 | II-13 | II-14 | II-2 | II-15 | II-16 |
| Constitutive Components (part by mass) | Component (A) | C-HPC (II-2) | 0.001 | 0.01 | 0.1 | 0.3 | 0.5 | 1.0 | 3.0 |
| | Component (B) | Dioctyl Ether *1 | 1.0 | 1.0 | 1.0 | 1.0 | 1.0 | 1.0 | 1.0 |
| | | Cetyl Alcohol | 1.3 | 1.3 | 1.3 | 1.3 | 1.3 | 1.3 | 1.3 |
| | | Stearyl Alcohol | 2.6 | 2.6 | 2.6 | 2.6 | 2.6 | 2.6 | 2.6 |
| | Component (C) | Behenyltrimethylammonium Chloride | 1.5 | 1.5 | 1.5 | 1.5 | 1.5 | 1.5 | 1.5 |
| | | pH Regulator | adequate dose | | | | | | |
| | | Pure Water *2 | balance | | | | | | |
| | | Component (B)/Component (A) | 1000 | 100 | 10 | 3.3 | 2 | 1 | 0.33 |
| Evaluation Results (after dried) | | Finger combability | 3.2 | 4.2 | 5.0 | 5.0 | 5.0 | 5.0 | 4.0 |
| | | Oily feeling | 3.6 | 3.6 | 4.6 | 4.6 | 4.6 | 4.0 | 4.0 |
| | | Manageability | 3.2 | 3.8 | 5.0 | 5.0 | 4.6 | 4.0 | 3.4 |

*1: Cognis' CETIOL OE
*2: To make 100 parts by mass in total.

TABLE 26

| Hair Cosmetic (Conditioner) | | | Example | | | | | |
|---|---|---|---|---|---|---|---|---|
| | | | II-2 | II-17 | II-18 | II-19 | II-20 | II-21 |
| Constitutive Components (part by mass) | Component (A) | C-HPC (II-2) | 0.5 | 0.5 | 0.5 | 0.5 | 0.5 | 0.5 |
| | Component (B) | Dioctyl Ether *1 | 1.0 | | | 3.0 | 5.0 | 10.0 |
| | | Dioctyl Carbonate *2 | | 1.0 | | | | |
| | | PPG-3 Benzyl Ether Myristate *3 | | | 1.0 | | | |
| | | Cetyl Alcohol | 1.3 | 1.3 | 1.3 | 1.3 | 1.3 | 1.3 |
| | | Stearyl Alcohol | 2.6 | 2.6 | 2.6 | 2.6 | 2.6 | 2.6 |
| | Component (C) | Behenyltrimethylammonium Chloride | 1.5 | 1.5 | 1.5 | 1.5 | 1.5 | 1.5 |
| | | pH Regulator | adequate dose | | | | | |
| | | Pure Water *4 | balance | | | | | |
| | | Component (B)/Component (A) | 2.0 | 2.0 | 2.0 | 6.0 | 10 | 20 |
| Evaluation Results (after dried) | | Finger combability | 5.0 | 5.0 | 4.6 | 5.0 | 5.0 | 5.0 |
| | | Oily feeling | 4.6 | 5.0 | 4.0 | 3.6 | 3.6 | 3.0 |
| | | Manageability | 4.6 | 4.6 | 4.0 | 5.0 | 5.0 | 5.0 |

*1: Cognis' trade name, CETIOL OE
*2: Cognis' trade name, CETIOL CC
*3: Croda's trade name, CRODAMOL STS
*4: To make 100 parts by mass in total.

TABLE 27

| Hair Cosmetic (Conditioner) | | | Example | | | | | |
|---|---|---|---|---|---|---|---|---|
| | | | II-2 | II-22 | II-23 | II-24 | II-25 | II-26 |
| Constitutive Components (part by mass) | Component (A) | C-HPC (II-2) | 0.5 | 0.5 | 0.5 | 0.5 | 0.5 | 0.5 |
| | Component (B) | Dioctyl Ether *1 | 1.0 | 1.0 | 1.0 | 1.0 | 1.0 | 1.0 |
| | | Cetyl Alcohol | 1.3 | 1.3 | 1.3 | 1.3 | 1.3 | 1.3 |
| | | Stearyl Alcohol | 2.6 | 2.6 | 2.6 | 2.6 | 2.6 | 2.6 |
| | Component (C) | Behenyltrimethylammonium Chloride | 1.5 | | | | | |
| | | Cetyltrimethylammonium Chloride | | 1.5 | | | | |
| | | Stearoxypropyltrimethylammonium Chloride *2 | | | 1.5 | | | |
| | | Stearamidopropyldimethylamine *3 | | | | 1.5 | | |
| | | Behanamidopropyldimethylamine *4 | | | | | 1.5 | |
| | | Stearyldimethylamine | | | | | | 1.5 |
| | | pH Regulator | adequate dose | | | | | |
| | | Pure Water *5 | balance | | | | | |

TABLE 27-continued

| Hair Cosmetic (Conditioner) | | Example | | | | | |
|---|---|---|---|---|---|---|---|
| | | II-2 | II-22 | II-23 | II-24 | II-25 | II-26 |
| Evaluation Results (after dried) | Finger combability | 5.0 | 5.0 | 5.0 | 5.0 | 5.0 | 5.0 |
| | Oily feeling | 4.6 | 4.6 | 4.6 | 4.6 | 4.6 | 4.6 |
| | Manageability | 4.6 | 4.6 | 5.0 | 5.0 | 5.0 | 5.0 |

*1: Cognis' CETIOL OE
*2: Kao's COATAMINE E-80K (effective ingredient 45%) was added in an amount of 3.3 parts by mass.
*3: Toho Industry's CATINAL MPAS
*4: Kao's FARMIN DM-220A
*5: To make 100 parts by mass in total.

From Tables 24 to 27, it is known that the conditioners of Examples II-1 to 26, and 50 to 52 were given good finger combability and manageability with no oily feeling after drying, as compared with the conditioners of Comparative Examples II-1 to 8.

Examples II-27 to 49

Production and Evaluation of Shampoo

Using C—HPC (II-2) as the component (A), shampoos each having the composition as in Tables 28 to 30 were produced according to an ordinary method.

Concretely, the surfactant (C) and a moderate amount of water were taken in a beaker, heated at 60° C. and dissolved. This was cooled to 50° C., and a polymer liquid prepared in the same manner as in Example II-1 was added thereto and uniformly mixed. The oil (B) was added to it, stirred and emulsified for 30 minutes, and cooled. Finally, water that had evaporated away by heating was replenished and the pH was measured. If desired, the pH was controlled to be 7 with a pH regulator (aqueous 50% citric acid solution or aqueous 48% sodium hydroxide solution).

Hair tresses washed with the plain shampoo used in Example II-1 were fully wetted with warm water at 35 to 40° C., and then washed with the shampoo of Examples II-27 to 49, rinsed with warm water, wiped with a towel to remove water, and combed. Subsequently, the hair tresses were dried with warm air of a drier, and again combed for final dressing to give a sample of tresses for evaluation. Five panelists tested and evaluated the tresses thereof. The finger combability, the oily feeling and the manageability of the sample of Comparative Examples II-12 was given a standard score 3; and the scores given by 5 panelists to each sample were averaged to give the mean score of each sample. The results are shown in Tables 28 to 30.

Comparative Examples II-9 to 13

Shampoos each having the composition as in Table 26 was produced in the same manner as in Example II-27, except that a different polymer as in Table 26 was used in place of the component (A) in Example II-27. The pH of the shampoos of Comparative Examples II-9 to 13 was controlled to be 7 with a pH regulator (aqueous 50% citric acid solution or aqueous 48% sodium hydroxide solution) optionally added thereto. The shampoos of Comparative Examples II-9 to 13 were tested and evaluated in the same manner as in Example II-27. The results are shown in Table 28.

Comparative Example II-14

Shampoo of Comparative Example II-14 was produced in the same manner as that for Example II-27 except that the oil (B) was not added thereto. The produced shampoo of Comparative Example II-14 was tested and evaluated in the same manner as that for the shampoo of Example II-27. The results are shown in Table 29.

TABLE 28

| Hair Cosmetic (Shampoo) | | | Example | Comparative Example | | | | |
|---|---|---|---|---|---|---|---|---|
| | | | II-27 | II-9 | II-10 | II-11 | II-12 | II-13 |
| Constitutive Components (part by mass) | Component (A) | C-HPC (II-2) | 0.5 | | | | | |
| | | Cationized Guar Gum *1 | | 0.5 | | | | |
| | | Cationized Hydroxyethyl Cellulose *2 | | | 0.5 | | | |
| | | Dimethyldiallylammonium Chloride/Acrylamide Copolymer *3 | | | | 0.5 | | |
| | | Dimethyldiallylammonium Chloride/Vinylpyrrolidone/Vinylimidazole Copolymer *4 | | | | | 0.5 | |
| | | Cationized Starch *5 | | | | | | 0.5 |
| | Component (B) | Dioctyl Carbonate *6 | 1.0 | 1.0 | 1.0 | 1.0 | 1.0 | 1.0 |
| | Component (C) | Sodium Laureth-2 Sulfate | 7.5 | 7.5 | 7.5 | 7.5 | 7.5 | 7.5 |
| | | Cocoyl Fatty Acid Amide Propylbetaine | 4.5 | 4.5 | 4.5 | 4.5 | 4.5 | 4.5 |
| | | pH Regulator | | | adequate dose | | | |
| | | Pure Water *7 | | | balance | | | |

TABLE 28-continued

|  |  | Example | Comparative Example | | | | |
|---|---|---|---|---|---|---|---|
| Hair Cosmetic (Shampoo) | | II-27 | II-9 | II-10 | II-11 | II-12 | II-13 |
| Evaluation Results (after dried) | Finger combability | 4.6 | 2.6 | 2.0 | 2.0 | 3.0 | 3.0 |
|  | Oily feeling | 5.0 | 2.6 | 2.6 | 2.0 | 3.0 | 3.6 |
|  | Manageability | 4.0 | 3.0 | 3.6 | 3.6 | 3.0 | 2.6 |

*1: Sansho's JAGUAR C13S
*2: Nalco's MERQUAT 10
*3: Nalco's MERQUAT 550
*4: BASF's LUVIQUAT SENSATION
*5: Nalco's SENSOMER CI50
*6: Cognis' CETIOL CC
*7: To make 100 parts by mass in total.

TABLE 29

|  |  |  | Example | | | | | | | | | | Comparative Example |
|---|---|---|---|---|---|---|---|---|---|---|---|---|---|
| Hair Cosmetic (Shampoo) | | | II-28 | II-27 | II-29 | II-30 | II-31 | II-32 | II-33 | II-34 | II-35 | II-36 | II-14 |
| Constitutive Components (part by mass) | Component (A) | C-HPC (II-2) | 0.5 | 0.5 | 0.5 | 0.01 | 0.1 | 1.0 | 3 | 0.5 | 0.5 | 0.5 | 0.5 |
|  | Component (B) | Dioctyl Ether *1 | 1.0 |  |  | 1.0 | 1.0 | 1.0 | 1.0 | 0.1 | 5.0 | 10 |  |
|  |  | Dioctyl Carbonate *2 |  | 1.0 |  |  |  |  |  |  |  |  |  |
|  |  | PPG-3 Benzyl Ether Myristate *3 |  |  | 1.0 |  |  |  |  |  |  |  |  |
|  | Component (C) | Sodium Laureth-2 Sulfate | 7.5 | 7.5 | 7.5 | 7.5 | 7.5 | 7.5 | 7.5 | 7.5 | 7.5 | 7.5 | 7.5 |
|  |  | Cocoyl Fatty Acid Amide Propylbetaine | 4.5 | 4.5 | 4.5 | 4.5 | 4.5 | 4.5 | 4.5 | 4.5 | 4.5 | 4.5 | 4.5 |
|  |  | pH Regulator |  |  |  |  |  | adequate dose | | | | |  |
|  |  | Pure Water *4 |  |  |  |  |  | balance | | | | |  |
| Component (B)/Component (A) | | | 2.0 | 2.0 | 2.0 | 100 | 10 | 1.0 | 0.33 | 0.2 | 10 | 20 | — |
| Evaluation Results (after dried) | Finger combability | | 5.0 | 4.6 | 4.0 | 4.6 | 5.0 | 4.6 | 3.6 | 4.0 | 5.0 | 4.6 | 3.0 |
|  | Oily feeling | | 4.6 | 5.0 | 4.0 | 4.0 | 4.6 | 4.6 | 4.0 | 4.6 | 4.6 | 4.0 | 5.0 |
|  | Manageability | | 4.6 | 4.0 | 4.6 | 4.0 | 4.6 | 4.6 | 4.0 | 3.6 | 5.0 | 5.0 | 2.6 |

*1: Cognis' CETIOL OE
*2: Cognis' CETIOL CC
*3: Croda's CRODAMOL STS
*4: To make 100 parts by mass in total.

TABLE 30

|  |  |  | Example | | | | | | | | | | | | |
|---|---|---|---|---|---|---|---|---|---|---|---|---|---|---|
| Hair Cosmetic (Shampoo) | | | II-37 | II-38 | II-39 | II-40 | II-41 | II-42 | II-43 | II-44 | II-45 | II-46 | II-47 | II-48 | II-49 |
| Constitutive Components (part by mass) | Component (A) | C-HPC (II-2) | 0.5 | 0.5 | 0.5 | 0.5 | 0.5 | 0.5 | 0.5 | 0.5 | 0.5 | 0.5 | 0.5 | 0.5 | 0.5 |
|  | Component (B) | Dioctyl Ether *1 | 1.0 | 1.0 | 1.0 | 1.0 | 1.0 | 1.0 | 1.0 | 1.0 | 1.0 | 1.0 | 1.0 | 1.0 | 1.0 |
|  | Component (C) | Sodium Laureth-1 Sulfate | 10 |  |  |  |  |  |  |  |  |  |  |  |  |
|  |  | Sodium Laureth-2 Sulfate |  | 10 |  |  |  |  |  | 10 | 10 | 10 | 10 | 10 | 10 |
|  |  | Sodium Laureth-4,5 Acetate |  |  | 10 |  |  |  |  |  |  |  |  |  |  |
|  |  | Sodium Laureth-2 Sulfosuccinate |  |  |  | 10 |  |  |  |  |  |  |  |  |  |
|  |  | Sodium Alkylglutamate *2 |  |  |  |  | 10 |  |  |  |  |  |  |  |  |
|  |  | Cocoyl Fatty Acid Amide Propylbetaine |  |  |  |  |  |  |  |  | 2 |  |  |  |  |
|  |  | Laurylcarboxymethyl-hydroxyimidazolium betaine *3 |  |  |  |  |  | 10 |  |  |  |  |  |  |  |
|  |  | Laurylhydroxysulfobetaine *4 |  |  |  |  |  |  |  |  |  | 2 |  |  |  |
|  |  | Cocoyl Fatty Acid Monoethanolamide |  |  |  |  |  |  |  |  |  |  | 2 |  |  |
|  |  | Cocoyl Fatty Acid Methyl Ethanolamide |  |  |  |  |  |  |  |  |  |  |  | 2 |  |
|  |  | Laureth (3) |  |  |  |  |  |  |  |  |  |  |  |  | 2 |

TABLE 30-continued

| Hair Cosmetic (Shampoo) | | Example | | | | | | | | | | | | |
|---|---|---|---|---|---|---|---|---|---|---|---|---|---|---|
| | | II-37 | II-38 | II-39 | II-40 | II-41 | II-42 | II-43 | II-44 | II-45 | II-46 | II-47 | II-48 | II-49 |
| | Ceteareth (16) | | | | | | | | | | | | | 2 |
| | Alkylglucoside *6 | | | | | | | 10 | | | | | | |
| | pH Regulator | | | | | | | adequate dose | | | | | | |
| | Pure Water *7 | | | | | | | balance | | | | | | |
| Evaluation Results (after dried) | Finger combability | 4.0 | 4.6 | 4.6 | 4.6 | 4.6 | 4.0 | 4.6 | 4.4 | 4.6 | 4.6 | 4.6 | 4.6 | 4.6 |
| | Oily feeling | 4.0 | 4.4 | 4.4 | 3.4 | 4.6 | 4.6 | 4.4 | 4.4 | 4.6 | 4.6 | 4.6 | 4.6 | 4.6 |
| | Manageability | 4.0 | 4.6 | 4.6 | 4.6 | 4.0 | 4.0 | 4.0 | 3.6 | 4.0 | 5.0 | 5.0 | 4.4 | 4.4 |

*1: Cognis' CETIOL OE
*2: Ajinomoto's AMISOFT CS-11
*3: Kao's AMPHITOL 20YB (effective ingredient 40%) was added in an amount of 25 parts by mass.
*4: Kao's AMPHITOL 20HD (effective ingredient 30%) was added in an amount of 6.7 parts by mass.
*5: Kao's AMINON C11S
*6: Kao's MYDOL 10 (effective ingredient 40%) was added in an amount of 25 parts by mass.
*7: To make 100 parts by mass in total.

As obvious from Tables 28 to 30, the shampoos of Examples II-27 to 49 were given good finger combability and manageability with no oily feeling after drying, as compared with the shampoos of Comparative Examples II-9 to 14.

(1) Examples III-1 to 7, Comparative Examples III-1 and 2

Preparation of Emulsion

Using C—HPC (I-2) produced in Production Example I-2 as the component (A), emulsions each having the composition as in Table 31 were prepared.
(Step (I))
An aqueous solution of 10 mass % C—HPC (A) (the cationized hydroxyethyl cellulose and the cationized guar gum in Comparative Examples III-1 and 2 each were an aqueous 1 mass % solution) and the anionic surfactant (C') were taken in a beaker and mixed to be uniform, thereby preparing a mixture of C—HPC (A) and the anionic surfactant (C').
(Step (II))
The oil (B) was added to the above-mentioned mixture and, with stirring at 300 rpm (0.78 m/sec), emulsified for 60 minutes, and finally the remaining water was added to prepare an emulsion.

(2) Determination of Mean Particle Size of Oil Drops

The mean particle size of oil drops was determined, using a dynamic light scattering particle sizer LA-950 (by Horiba). For preventing the sample from being contaminated with bubbles during measurement, the emulsion was completely dispersed in the cell of LA-950 (measurement condition: stirring 7, circulation 7), and after the stirring and the circulation were stopped, the sample was tested. The volume-based median diameter was measured at a temperature of 25° C., and was referred to as the mean particle size.

A smaller mean particle size of oil drops means that the emulsion force of the oil (B) is large, while a larger mean particle size thereof means that the emulsion force is small.

(3) Evaluation of Emulsion Condition

The emulsion prepared in (1) was diluted with a moderate amount of water to be an aqueous 5 mass % solution. From the outward appearance of the emulsion, the emulsified condition thereof was evaluated according to the following evaluation criteria. The results are shown in Table 31.
(Evaluation Criteria)
Emulsion Condition
  A: Emulsifiable.
  B: Not emulsifiable (oily drops aggregated).

TABLE 31

| Emulsion Preparation | | | Example | | | | | | | Comparative Example | |
|---|---|---|---|---|---|---|---|---|---|---|---|
| | | | III-1 | III-2 | III-3 | III-4 | III-5 | III-6 | III-7 | III-1 | III-2 |
| Constitutive Components (part by mass) | Ingredient (A) | C-HPC (I-2) | 0.5 | 1.0 | 2.0 | 3.0 | 1.0 | 2.0 | 3.0 | | |
| | | Cationized Hydroxyethyl Cellulose *1 | | | | | | | | 1.0 | |
| | | Cationized Guar Gum *2 | | | | | | | | | 1.0 |
| | Ingredient (B) | Dimethicone *3 | 50.0 | 50.0 | 50.0 | 50.0 | 50.0 | 50.0 | 50.0 | 50.0 | 50.0 |
| | Ingredient (C') | Sodium Laureth-2 Sulfate | 0.05 | 0.10 | 0.20 | 0.30 | | | | 0.10 | 0.10 |
| | | Sodium Laureth-4,5 Acetate | | | | | 0.40 | 0.80 | 1.20 | | |
| | | Pure Water *4 | | | | | balance | | | | |
| Evaluation Results | | Mean Particle Size of Oil Drops (μm) | 7.5 | 5.7 | 8.6 | 11.6 | 5.9 | 8.6 | 10.1 | 39.7 | 86.4 |
| | | Emulsion Condition | A | A | A | A | A | A | A | B | B |

*1: Nalco's MERQUAT 10
*2: Sansho's JAGUAR C13S
*3: Shin-etsu Chemical's KF-96H-100,000 cs
*4: To make 100 parts by mass in total.

Examples III-8 to 16, Comparative Examples III-3 to 6

Production and Evaluation of Conditioner (Step (III))

A moderate amount of water and the surfactant (C) were taken in a beaker and mixed with heating at 80° C. to prepare an aqueous solution, which was then added to the above-mentioned aqueous polymer solution and uniformly mixed. After melted, the oil (B), cetyl alcohol and stearyl alcohol were added thereto, emulsified with stirring for 30 minutes, and cooled. Subsequently, the emulsion having the composition as in Table 31 was added thereto and uniformly mixed. Finally, water that had evaporated away by heating was replenished and the pH of the mixture was measured. The pH was controlled to be 5 with a pH regulator (aqueous 50% citric acid solution). In Comparative Example III-3, a commercial emulsion (Toray Dow Corning's BY22-029) was used in place of the emulsion shown in Table 31.

Hair tresses were washed with plain shampoo mentioned below, fully wetted with warm water at 35 to 40° C., and thereafter 1 g of the conditioner of Examples III-8 to 16 was applied thereto and spread evenly thereover. Subsequently, the hair tresses were rinsed with warm water for 30 seconds, wiped with a towel to remove water, combed, and dried with warm air from a drier, and again combed for final dressing to give a sample of tresses for evaluation.

Five panelists tested and evaluated the tresses for the finger combability, oily feeling, manageability and moist feeling thereof according to the following evaluation criteria and evaluation methods. The results are shown in Tables 32 and 33.

(Composition of Plain Shampoo)

| Component | (%) |
| --- | --- |
| Na polyoxyethylene lauryl ether sulfate (42.0% as EMAL E-27C (by Kao, effective content, 27% by weight)) | 11.3 |
| Cocoyl fatty acid N-methylethanolamide (AMINONE C-11S (by Kao) | 3.0 |
| Citric acid | 0.2 |
| Methylparaben | 0.3 |
| Pure water | balance |
| Total | 100.0 |

(Production of Plain Shampoo)

The components were taken in a beaker, heated at 80° C. and mixed, and after their uniform dissolution was confirmed, the mixture was cooled to give plain shampoo.

(Evaluation Criteria, Evaluation Methods)

Finger Combability
 5: Excellent finger combability.
 4: Good finger combability.
 3: Average.
 2: Bad finger combability.
 1: Extremely bad finger combability.

Oily Feeling
 5: Not oily.
 4: Not so much oily.
 3: Average.
 2: Somewhat oily.
 1: Oily.

Manageability
 5: The hair was very well manageable.
 4: The hair was well manageable.
 3: Average.
 2: The hair was poorly manageable.
 1: The hair was not manageable at all.

Moist Feeling
 5: The hair felt very moist.
 4: The hair felt moist.
 3: Average.
 2: The hair did not feel moist so much.
 1: The hair did not feel moist at all.

The finger combability, the oily feeling, the manageability and the moist feeling of the sample of Comparative Examples III-3 was given a standard score 3; and the scores given by 5 panelists to each sample were averaged to give the mean score of each sample.

TABLE 32

| | | | Example | | | | | | | Comparative Example | | |
| --- | --- | --- | --- | --- | --- | --- | --- | --- | --- | --- | --- | --- |
| Hair Cosmetic (Conditioner) | | | III-8 | III-9 | III-10 | III-11 | III-12 | III-13 | III-14 | III-3 | III-4 | III-5 |
| Constitutive Components (part by mass) | Component (A) | Emulsion Used | 80 | 81 | 82 | 83 | 84 | 85 | 86 | | 27 | 28 |
| | | C-HPC (I-2) | 0.02 | 0.04 | 0.08 | 0.12 | 0.04 | 0.08 | 0.12 | | | |
| | | Cationized Hydroxyethyl Cellulose *1 | | | | | | | | | 0.02 | |
| | | Cationized Guar Gum *2 | | | | | | | | | | 0.02 |
| | Component (B) | Cetyl Alcohol | 1.3 | 1.3 | 1.3 | 1.3 | 1.3 | 1.3 | 1.3 | 1.3 | 1.3 | 1.3 |
| | | Stearyl Alcohol | 2.6 | 2.6 | 2.6 | 2.6 | 2.6 | 2.6 | 2.6 | 2.6 | 2.6 | 2.6 |
| | | Dimethicone *3 | 2.0 | 2.0 | 2.0 | 2.0 | 2.0 | 2.0 | 2.0 | | 2.0 | 2.0 |
| | | Dimethicone *4 | | | | | | | | 2.0 | | |
| | Component (C) | Behenyltrimethyl-ammonium Chloride | 1.5 | 1.5 | 1.5 | 1.5 | 1.5 | 1.5 | 1.5 | 1.5 | 1.5 | 1.5 |
| | | Sodium Laureth-2 Sulfate | 0.002 | 0.004 | 0.008 | 0.012 | | | | | 0.002 | 0.002 |
| | | Sodium Laureth-4,5 Carboxylate | | | | | 0.016 | 0.032 | 0.048 | | | |
| | | pH Regulator | | | | | adequate dose | | | | | |
| | | Pure Water *5 | | | | | balance | | | | | |
| Evaluation Results (after dried) | | Finger combability | 4.0 | 4.0 | 4.0 | 4.0 | 4.0 | 4.6 | 4.6 | 3.0 | 2.4 | 2.4 |
| | | Oily feeling | 3.0 | 3.6 | 3.6 | 3.8 | 3.8 | 4.0 | 3.6 | 3.0 | 4.0 | 2.0 |

TABLE 32-continued

| Hair Cosmetic (Conditioner) | Example | | | | | | | Comparative Example | | |
|---|---|---|---|---|---|---|---|---|---|---|
| | III-8 | III-9 | III-10 | III-11 | III-12 | III-13 | III-14 | III-3 | III-4 | III-5 |
| Manageability | 3.6 | 3.6 | 3.6 | 4.0 | 3.6 | 3.6 | 3.6 | 3.0 | 3.0 | 3.0 |
| Moist Feeling | 3.6 | 3.6 | 4.0 | 3.6 | 3.6 | 4.0 | 4.0 | 3.0 | 3.0 | 3.0 |

*1: Nalco's MERQUAT 10
*2: Sansho's JAGUAR C13S
*3: Shin-etsu Chemical's KF-96H-100,000 cs
*4: Toray Dow Corning's BY22-029
*5: To make 100 parts by mass in total.

TABLE 33

| Hair Cosmetic (Conditioner) | | | Example | |
|---|---|---|---|---|
| | | | III-15 | III-16 |
| Constitutive Components (part by mass) | Emulsion Used | | 85 | 85 |
| | Component (A) | C-HPC(I-2) | 0.02 | 0.04 |
| | Component (B) | Cetyl Alcohol | 1.3 | 1.3 |
| | | Stearyl Alcohol | 2.6 | 2.6 |
| | | Dimethicone *1 | 0.5 | 1.0 |
| | Component (C) | Behenyltrimethyl-ammonium Chloride | 1.5 | 1.5 |
| | | Sodium Laureth-4,5 Carboxylate | 0.008 | 0.016 |
| | | pH Regulator | adequate dose | |
| | | Pure Water *2 | balance | |
| Evaluation Results (after dried) | | Finger combability | 4.0 | 3.6 |
| | | Oily feeling | 3.6 | 3.6 |
| | | Manageability | 4.0 | 4.0 |
| | | Moist Feeling | 3.6 | 3.2 |

*1: Shin-etsu Chemical's KF-96H-100,000 cs
*2: To make 100 parts by mass in total.

As obvious from Tables 32 and 33, the conditioners of Examples III-8 to 16 were given good finger combability, manageability and moist feeling with no oily feeling, as compared with the conditioners of Comparative Examples III-3 to 5.

Examples III-17 to 22

Production and Evaluation of Shampoo

Using C—HPC (I-2) as the component (A), shampoo having the composition as in Table 34 was prepared.

Concretely, cationized guar gum and a moderate amount of water were taken in a beaker and uniformly dissolved. The surfactant (C) was added thereto and dissolved by heating at 60° C. This was cooled down to 45° C., and ethylene glycol distearate (B) and the emulsion having the composition shown in Table 31 were added thereto, emulsified by stirring for 30 minutes, and cooled. Finally, water that had evaporated away by heating was replenished and the pH of the mixture was measured. If desired, the pH was controlled to be 7 with a pH regulator (aqueous 50% citric acid solution or aqueous 48% sodium hydroxide solution). According to the same evaluation method as in Example I-1, the finger combability, oily feeling, manageability and moist feeling of hair were evaluated. The results are shown in Table 34. The finger combability, the oily feeling, the manageability and the moist feeling of the sample of Comparative Examples III-6 was given a standard score 3; and the scores given by 5 panelists to each sample were averaged to give the mean score of each sample.

Comparative Example III-6

Shampoo was produced in the same manner as in Examples III-17 to 22 except that the emulsion to be incorporated therein was changed to a commercial emulsion (Toray Dow Corning's BY22-029). The pH of the shampoo was controlled to be 7 with a pH regulator (aqueous 50% citric acid solution or aqueous 48% sodium hydroxide solution).

TABLE 34

| Hair Cosmetic (Shampoo) | | | Example | | | | | | Comparative Example |
|---|---|---|---|---|---|---|---|---|---|
| | | | III-17 | III-18 | III-19 | III-20 | III-21 | III-22 | III-6 |
| Constitutive Components (part by mass) | | Emulsion Used | 81 | 82 | 83 | 84 | 85 | 86 | |
| | Component (A) | C-HPC (I-2) | 0.04 | 0.08 | 0.12 | 0.04 | 0.08 | 0.12 | |
| | | Cationized Guar Gum *1 | 0.25 | 0.25 | 0.25 | 0.25 | 0.25 | 0.25 | 0.25 |
| | Component (B) | Dimethicone *2 | 2.0 | 2.0 | 2.0 | 2.0 | 2.0 | 2.0 | |
| | | Dimethicone *3 | | | | | | | 2.0 |
| | | Ethylene Glycol Distearate *4 | 0.7 | 0.7 | 0.7 | 0.7 | 0.7 | 0.7 | 0.7 |
| | Component (C) | Sodium Laureth-1 Sulfate | 13.0 | 13.0 | 13.0 | 13.0 | 13.0 | 13.0 | 13.0 |
| | | Sodium Laureth-2 Sulfate | 0.004 | 0.008 | 0.012 | | | | |
| | | Sodium laureth-4,5 Acetate | | | | 0.016 | 0.032 | 0.048 | |
| | | Cocamide Propylbetaine | 1.5 | 1.5 | 1.5 | 1.5 | 1.5 | 1.5 | 1.5 |
| | | Cocoyl Fatty Acid Monoethanolamide | 0.3 | 0.3 | 0.3 | 0.3 | 0.3 | 0.3 | 0.3 |
| | | NaCl | 1.0 | 1.0 | 1.0 | 1.0 | 1.0 | 1.0 | 1.0 |
| | | pH Regulator | | | | adequate dose | | | |
| | | Pure Water *2 | | | | balance | | | |
| Evaluation Results (after dried) | | Finger combability | 3.6 | 3.6 | 3.6 | 3.6 | 3.6 | 3.6 | 3.0 |
| | | Oily feeling | 4.0 | 4.0 | 4.0 | 3.6 | 4.0 | 4.0 | 3.0 |

TABLE 34-continued

| Hair Cosmetic (Shampoo) | Example | | | | | | Comparative Example |
|---|---|---|---|---|---|---|---|
| | III-17 | III-18 | III-19 | III-20 | III-21 | III-22 | III-6 |
| Manageability | 3.6 | 3.6 | 3.6 | 3.6 | 3.6 | 3.6 | 3.0 |
| Moist Feeling | 3.6 | 3.2 | 3.2 | 3.6 | 3.6 | 4.0 | 3.0 |

*1: Sansho's JAGUAR C13S
*2: Shin-etsu Chemical's KF-96H-100,000 cs
*3: Toray Dow Corning's BY22-029
*4: Kao's SA-M2
*5: To make 100 parts by mass in total.

As obvious from Table 34, the shampoos of Examples III-17 to 22 were given good finger combability, manageability and moist feeling with no oily feeling, as compared with the shampoo of Comparative Example III-6.

INDUSTRIAL APPLICABILITY

The hair cosmetic of the present invention is favorably used in the field of hair shampoo, hair rinse, treatment, conditioner, out-bath hair conditioner, hair cream, blow lotion, hair pack, hair color, conditioning gel, conditioning foam, etc.

The invention claimed is:

1. A method of treating hair with a hair cosmetic, comprising:
   applying the hair cosmetic to hair;
   wherein the hair cosmetic comprises a cationized hydroxypropyl cellulose (A), an oil (B) of which the amount of dissolution in 100 g of water at 20° C. is from 0 to 1 g, and a surfactant (C), wherein
   the cationized hydroxypropyl cellulose (A) has an anhydroglucose-derived main chain represented by the following general formula (1), and has a degree of substitution with cationized ethyleneoxy group of from 0.22 to 1.00 and a degree of substitution with propyleneoxy group of from 0.2 to 2.7:

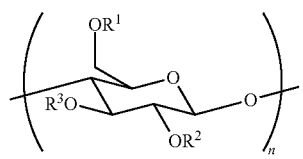
(1)

wherein $R^1$, $R^2$ and $R^3$ each independently represent a substituent having a cationized ethyleneoxy group and a propyleneoxy group represented by the following general formula (2),
n indicates a mean degree of polymerization of anhydroglucose and is a number of from 464 to 1326;

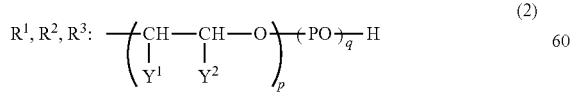
(2)

wherein one of $Y^1$ and $Y^2$ is a hydrogen atom and the other is a cationic group represented by the following general formula (3),
PO represents a propyleneoxy group,
p indicates the number of cationized ethyleneoxy groups ($(—CH(Y^1)—CH(Y^2)—O—$) in the general formula (2) and q indicates the number of propyleneoxy groups (—PO—) therein, each representing 0 or a positive integer; in case where both of p and q are not 0, the addition sequence of the cationized ethyleneoxy group and the propyleneoxy group is not defined, and in case where p and/or q are/is 2 or more, a binding form may be any of like a block co-polymer or like a random co-polymer;

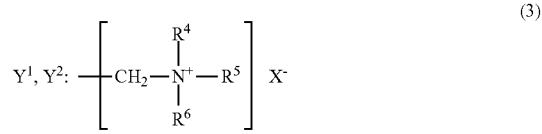
(3)

wherein $R^4$, $R^5$ and $R^6$ each independently represent a linear or branched alkyl group having from 1 to 3 carbon atoms, and
$X^-$ represents an anionic group,
an amount of the oil (B) is 0.1 to 10% by mass based on total amount of the hair cosmetic,
the oil (B) comprises a compound (B2) and a higher alcohol (B3),
the compound (B2) is at least one ester compound selected from compounds represented by the following general formula (4), dialkyl carbonate compounds represented by the following general formula (5), and dialkyl ether compounds represented by the following general formula (6):

$$R^7O\text{-}(AO)_m—COR^8 \tag{4}$$

wherein $R^7$ represents a hydrocarbon group having from 6 to 20 carbon atoms and containing at least one substituted or unsubstituted aromatic ring,
$R^8$ represents a linear or branched alkyl or alkenyl group having from 1 to 25 carbon atoms,
AO represents an alkyleneoxy group having from 2 to 4 carbon atoms,
m indicates a number of from 1 to 50, and in case where m is 2 or more, m's AO groups may be the same or different;

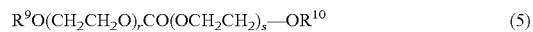
$$R^9O(CH_2CH_2O)_rCO(OCH_2CH_2)_s—OR^{10} \tag{5}$$

wherein $R^9$ and $R^{10}$ each represent a linear or branched alkyl and/or alkenyl group each having from 6 to 22 carbon atoms; r and s each indicate 0 or a number of from 1 to 50;

$$R^{11}—O—R^{12} \tag{6}$$

wherein $R^{11}$ and $R^{12}$ each represent a linear or branched alkyl and/or alkenyl group each having from 6 to 22 carbon atoms, and a ratio by mass of the compound (B2) to component (A) (B2/A) is 1 to 10, wherein the content of the cationized hydroxypropyl cellulose (A) is from 0.1 to 1.0% by mass, and wherein the higher alcohol (B3) is at least one higher alcohol selected from the group consisting of cetyl alcohol and stearyl alcohol.

2. The method according to claim 1, wherein the content of the cationized hydroxypropyl cellulose (A) is from 0.03 to 1.0% by mass.

3. The method according to claim 1, wherein the mean degree of polymerization, n, of the anhydroglucose in the general formula (1) is from 539 to 1186.

4. The method according to claim 1, wherein the ratio by mass of the oil (B) to the cationized hydroxypropyl cellulose (A) ((B)/(A)) is from 0.1 to 5000.

5. The method according to claim 1, wherein the ratio by mass of the surfactant (C) to the cationized hydroxypropyl cellulose (A) [surfactant (C)/cationized hydroxypropyl cellulose (A)] is from 0.1 to 2000.

6. The method according to claim 1, wherein the cationized hydroxypropyl cellulose (A) is obtained by the following steps (a-1) to (a-3):

Step (a-1): a step of adding a cationizing agent to a cellulose-containing raw material and processing it with a grinder, Step (a-2): a step of adding a base to the grinder-processed product obtained in the step (a–1), and while processing it with a grinder, reacting the cellulose-containing raw material and the cationizing agent to give a cationized cellulose, Step (a-3): a step of reacting the cationized cellulose obtained in the step (a-2) with propylene oxide to give the cationized hydroxypropyl cellulose (A).

7. The method according to claim 1, wherein the cationized hydroxypropyl cellulose (A) is obtained by the following steps (b-1) to (b-4):

Step (b-1): a step of processing a cellulose-containing raw material with a grinder to give a cellulose-containing raw material that comprises a cellulose having a degree of crystallinity of from 10 to 50%, Step (b-2): a step of adding to the cellulose-containing raw material obtained in the step (b-1), a base in an amount of from 0.6 to 1.5 molar times per mol of the anhydroglucose unit that constitutes the cellulose in the cellulose-containing raw material, and water in an amount of from 20 to 100% by mass relative to the cellulose in the cellulose-containing raw material, thereby giving an alkali cellulose, Step (b-3): a step of reacting the alkali cellulose obtained in the step (b-2) with propylene oxide to give a hydroxypropyl cellulose, Step (b-4): a step of reacting the hydroxypropyl cellulose obtained in the step (b-3) with a cationizing agent to give the cationized hydroxypropyl cellulose (A).

8. The method according to claim 1, wherein the cationized hydroxypropyl cellulose (A) is obtained by the following steps (c-1) to (c-4):

Step (c-1): a step of processing a mixture of a cellulose-containing raw material and a base in an amount of from 0.6 to 1.5 molar times per mol of the anhydroglucose unit that constitutes the cellulose in the cellulose-containing raw material, with a grinder under the condition where the water content in the cellulose-containing raw material is at most 10% by weight relative to the cellulose therein, thereby giving a ground cellulose/base mixture in which the mean particle size of the cellulose is from 10 to 150 μm, Step (c-2): a step of adding water to the ground cellulose/base mixture obtained in the step (c-1) to thereby control the water content in the ground cellulose/base mixture to be from 30 to 100% by mass relative to the cellulose in the cellulose-containing raw material used in the step (c-1), thereby giving an alkali cellulose, Step (c-3): a step of reacting the alkali cellulose obtained in the step (c-2) with propylene oxide to give a hydroxypropyl cellulose, Step (c-4): a step of reacting the hydroxypropyl cellulose obtained in the step (c-3) with a cationizing agent to give the cationized hydroxypropyl cellulose (A).

9. The method according to claim 1, wherein the hair cosmetic is a shampoo.

10. The method according to claim 1, wherein the hair cosmetic is a conditioner, hair rinse, or treatment.

11. The method according to claim 1, wherein the hair cosmetic is applied to hair in an out-bath treatment.

12. The method according to claim 1, wherein the degree of substitution with propyleneoxy group of the cationized hydroxypropyl cellulose (A) is from 0.2 to 1.8.

13. The method according to claim 1, wherein the degree of substitution with propyleneoxy group of the cationized hydroxypropyl cellulose (A) is from 0.3 to 2.7.

14. The method according to claim 1, wherein the degree of substitution with propyleneoxy group of the cationized hydroxypropyl cellulose (A) is from 0.6 to 2.5.

15. The method according to claim 1, wherein the degree of substitution with cationized ethyleneoxy group of the cationized hydroxypropyl cellulose (A) is from 0.25 to 0.75.

16. The method according to claim 1, wherein the degree of substitution with cationized ethyleneoxy group of the cationized hydroxypropyl cellulose (A) is from 0.3 to 0.35.

17. The method according to claim 1, wherein the mean degree of polymerization n of anhydroglucose in the general formula (1) is from 739 to 964.

18. The method according to claim 1, wherein the ratio by mass of the oil (B) to the cationized hydroxypropyl cellulose (A) ((B)/(A)) is from 6 to 50.

19. The method according to claim 1, wherein the ratio by mass of the oil (B) to the cationized hydroxypropyl cellulose (A) ((B)/(A)) is from 7 to 20.

* * * * *